United States Patent [19]
Vakharia et al.

[11] Patent Number: 5,788,970
[45] Date of Patent: Aug. 4, 1998

[54] CHIMERIC INFECTIOUS BURSAL DISEASE VIRUS CDNA CLONES, EXPRESSION PRODUCTS AND VACCINES BASED THEREON

[75] Inventors: Vikram Vakharia; David B. Snyder, both of Bowie; Stephanie A. Mengel-Whersat, Hyattsville, all of Md.

[73] Assignee: The University of Maryland College Park, College Park, Md.

[21] Appl. No.: 219,262

[22] Filed: Mar. 29, 1994

[51] Int. Cl.$^6$ .................. A61K 39/295; C12N 15/40; C07K 14/08
[52] U.S. Cl. ................. 424/192.1; 424/202.1; 435/235.1; 530/389.4
[58] Field of Search ............... 424/192.1, 202.1; 530/389.4; 435/235.1

[56] References Cited

FOREIGN PATENT DOCUMENTS

WO91/16925  11/1991  WIPO .............. A61K 39/15

OTHER PUBLICATIONS

Journal of General Virology, vol. 70, pp. 1473–1481, 1989, K.J. Fahey, et al., "A Conformation Immunogen on VP–2 of Infectious Bursal Disease Virus that Induces Virus–Neutralizing Antibodies that Passively Protect Chickens".

Archives of Virology, vol. 120, pp. 193–205, 1991, C.D. Bayless, et al., "A Recombinant Fowlpox Virus that Expresses the VP2 Antigen of Infectious Disease Virus Induces Protection Against Mortality Caused by the Virus".

Journal of General Virology, vol. 74, pp. 1201–1206, 1993, V.N. Vakharia, et al., "Infectious Bursal Disease Virus Structural Proteins Expressed in a Baculovirus Recombinant Confer Protection in Chickens".

Heine et al. "Infectious bursal disease virus structural protein VP2 . . . " Arch Virol (1993) 131:277–292.

Jagadish et al. "Expression and characterization of infections bursal disease virus . . . " Gene, 95 (1990) 179–186.

Heine et al. "Sequence analysis and expression of the host protective . . . " J Gen Virol (1991), 72, 1835–1843.

*Primary Examiner*—Ponnathapura Achutamurthy
*Assistant Examiner*—Phuong T. Bui
*Attorney, Agent, or Firm*—Oblon, Spivak, McClelland, Maier & Neustadt, P.C.

[57] ABSTRACT

Chimeric cDNA for the expression of immunogenic polypeptides include the genetic epitopic determinants for a base infectious bursal disease virus strain and at least one other infectious bursal disease virus strain. The genetic epitopic determinants encode amino acids or amino acid sequences which define epitopes bound to by previously established monoclonal antibodies. The immunogens expressed by the cDNA may be employed to provide a vaccine against a plurality of IBDV strains. The epitopic determinant of IBDV lethal strains has been detected, and an immunogen for conferring immunity is disclosed. Similarly, a monoclonal antibody specific for IBDV lethal strains is identified, and a vaccine for passive immunization is also disclosed. Immunogens exhibiting conformational epitopes, in the form of virus-like particles, are effective in the preparation of vaccines.

10 Claims, 38 Drawing Sheets

FIG. 1B

Fig. 3B

```
             10         20         30         40         50         60
             |          |          |          |          |          |
GLS     NGTINAVTFQ GSLSELTDVS YNGLMSATAN INDKIGNVLV GEGVTVLSLP TSYDLGYVRL
DS326   ---------- ---------- ---------- ---------- ---------- ----------
E/Del   ---------- ---------- ---------- ---------- ---------- ----------
D78     ---------- ---------- ---------- ---------- ---------- ----------
Cu-1    ---------- ---------- ---------- ---------- ---------- ----------
PBG98   ---------- ---------- ---------- ---------- ---------- ----------
52/70   ---------- ---------- ---------- ---------- ---------- ----------
STC     ---------- ---------- ---------- ---------- ---------- ----------
002-73  ---------- -------Y-- ---------- ---------- ---------- ----------
OH      ---------- ---------- ---------- ---------- ---------- ------S---

70         80         90        100        110
             |          |          |          |          |
GDPIPAIGLD PKMVATCDSS DRPRVYTITA ADDYQFSSQY QTGGVTITLF SANIDAITSL  - 240
---------- ---------- ---------- ---------- ---------- ----------
---------- ---------- ---------- ----N----- -S-------- ----------
---------- ---------- ---------- ---------- ---P------ ----------
---------- ---------- ---------- ---------- ---P------ ----------
---------- ---------- ---------- ---------- ---P------ ----------
---------- ---------- ---------- ---------- ---P------ ----------
---------- ---------- ---------- ---------- ---P------ -------N--
---------- ---------- ---------- ---------- ---P------ ----------
---A------ ---LM----- ------V--- ---E------ -L IPS--KT ---T---L--
```

FIG. 3C

```
                                    10         20         30         40         50         60
                                    |          |          |          |          |          |
GLS       SVGGELVF KTSVHSLVLGAT IYLIGFDGSA VITRAVAANN GLTTGTDNLM PFNLVIPTNE
DS326     -------- ---Q-------- ---------- ---------- ---A------ ----------
E/Del     -------- ---Q-------- ---------- ---------- ---A--I--- ----------
D78       -------- Q-----G----- ---------- -------TT- ---------- ----------
Cu-1      -------- Q-----G----- ---------- -------TT- ---------- -----S----
PBG98     -------- R-----G----- ---------- -------TT- ---------- ----------
52/70     -I------ Q----QG----- ---------- -T-----TA- ---A------ ----------
STC       -------- Q----QG----- ---------- -------TT- ---A------ ----------
002-73    -------- Q----QG--N-- -F------T- -V-----TT- ---A------ ---------S
OH        ------I- -SQVTI-SIEVDV -F-------- --TVK---TDF ----N--V-- ---GG---S 70         80         90        100        110
                                    |          |          |          |          |
          ITQPITSIKL EIVTSKSGGQ EGDQMSWSAS GSLAVTIHGG NYPGALRPVT LVAYERVATG  - 360
          ---K------ ---L------ ---------- ---------- ---------- ----------
          ---I------ ---------- -D-A-E---- ---------- ---------- ----------
          ---------- ---------- ---A------ ---------- ---------- ----------
          ---------- ---------- ---A----R- ---------- ---------- ----------
          ---------- ---------- ---A----K- ---------- ---------- ----------
          ---------- ---------- ---A--L-R- ---------- ---------- ----------
          ---------- ---------- ---A------ ---N------ ---------- ----------
          -V-------- ---------- ---A------ ---------- ---------- ----------
          ---V------ ---------- ---A---L-- ---T---V-- ---------- ---A------ - 361
          ---M------ -V--Y-R-T- A--PI--TV- ---T------ ---------- ----------
```

Labels (rows): GLS, DS326, E/Del, D78, Cu-1, PBG98, 52/70, STC, 002-73, OH

FIG. 3D

```
              10         20         30         40         50         60
              |          |          |          |          |          |
GLS      SVVTVAGVSN FELIPNPELA KNLVTEYGRF DPGAMNYTKL ILSERDRLGI KTVWPTREYT
DS326    ---------- ---------- ---------- ---------- ---------- ----------
E/Del    ---------- ---------- ---------- ---------- ----H----- ----------
D78      ---------- ---------- ---------- ---------- ---------- ----------
Cu-1     ---------- ---------- ---------- ---------- ---------- ----------
PBG98    ---------- ---------- ---------- ---------- ---------- ----------
52/70    ---------- ---------- ---------- ---------- ---------- ----------
STC      ---------- ---------- ---------- ---------- ---------- ----------
002-73   ---------- ---------- ---------- ---------- ---------- ----------
OH       ---------- ---------- ---------- ---------- ---------- ----------

70         80         90        100        110
              |          |          |          |          |
         DFREYFMEVA DLSSPLKIAG AFGFKDIIRA IRRIAVPVVS TLFPPAAPLA HAIGEGVDYL - 480
         ---------- --N------- ---------- ---------- ---------- ----------
         ---------- --N------- ---------- ---------- ---------- ----------
         ---------- --N------- ---------- ---------- ---------- ----------
         ---------- --N------- ---------- ---------- ---------- ----------
         ---------- --N------- ---------- ---------- ---------- ----------
         ---------- --N------- ---------- ---------- ---------- ----------
         ---------- --N------- ---------- ---------- ---------- ----------
         ---------- --N------- ----K----- ---------- ---------- ----------
         ---------- --N------- ---------- ---------- ---------- --NR------ - 481
```

```
                10          20          30          40          50          60
                 -           -           -           -           -           -
GLS      LGDEAQAASG TARAASGKAR AASGRIRQLT LAADKGYEVV ANLFQVPQNP VVDGILASPG
DS326    ---------- ---------- ---------- ---------- ---------- ----------
E/Del    ---------- ---------- ---------- ---------- ---------- ----------
D78      ---------- ---------- ---------- ---------- ---------- ----------
Cu-1     ---------- ---------- ---------- ---------- ---------- ----------
PBG98    ---------- ---------- ---------- ---------- ---------- ----------
52/70    ---------- ---------- ---------- ---------- ---------- ----------
STC      ---------- ---------- ---------G ---------- ----M----- ----------
002-73   ---------- ---------- ---------- ---------- ---------- ----------
OH       ---------- ---------- ---------- ---------- --------I- ----------

70          80          90         100         110
                 -           -           -           -           -
GLS      ILRGAHNLDC VLREGATLFP VVITTVEDAM TPKALNSKMF AVIEGVREDL QPPSQRGSFI . 600
DS326    ---------- ---------- ---------- ---------- -----A---- ---------- - 601
E/Del    V--------- ---------- ---------- ---------- ---------- ----------
D78      V--------- ---------- ---------- ---------- ---------- ----------
Cu-1     V--------- ---------- ---------- ---------- ---------- ----------
PBG98    V--------- ---------- ---------- ---------- ---------- ----------
52/70    V--------- ---------- ---------- ---------I ---------- ----------
STC      V--------- ---------- ---------- ---------- ---------- ----------
002-73   V--------- ---------- ---L--EL-- ---------- -----A---- ----------
OH       ---------- -SK------- ---------- ---------- ---------- ----------
```

```
                 10         20         30         40         50         60
                 |          |          |          |          |          |
GLS     RTLSGHRVYG YAPDGVLPLE TGRDYTVVPI DDVWDDSIML SKDPIPPIVG NSGNLAIAYM
DS326   ---------- ---------- ---------- ---------- ---------- ----------
E/Del   ---------- ---------- ---------- ---------- ---------- ----------
D78     ---------- ---------- ---------- ---------- ---------- ----------
Cu-1    ---------- ---------- ---------- ---------- ---------- ----------
PBG98   ---------- ---------- ---------- ---------- ---------- ----------
52/70   ---------- ---------- ---------- ---------- ---------- ----------
STC     ---------- ---------- ---------- ---------- ---------- ----------
002-73  ---------- ---------- ---------- ---------- ---------- ----------
OH      ---------- ---------- ---------- ---------Q ---------- ----------

70         80         90        100        110
                 |          |          |          |          |
        DVFRPKVPIH VAMTGALNAC GEIEKISFRS TKLATAHRLG LKLAGPGAFD VNTGPNWATF -720
        ---------- -------Y-- ---------- ---------- ---------- ----------
        ---------- ---------- -----V---- ---------- -R-------- ----------
        ---------- ---------- -----V---- ---------- ---------- ----------
        ---------- ---------- -----V---- ---------- ---------- ----------
        -------P-- ---------- ---------- ---------- ---------- ----------
        ---------- -------F-- ---V------ ---------- ---------- -------I--
        ---------- ---------- --V--V---- ---------- ---------- ----------
        ---------- -------S-- ---SV----- ---------- -M-----DY- -----I----
```

FIG. 3G

```
             10         20         30         40         50         60
             |          |          |          |          |          |
       IKRFPHNPRD WDRLPYLNLP YLPPNAGRQY HLAMAASEFK ETPELESAVR AMEAAASVDP
GLS    ---------- ---------- ---------- ---------- ---------- ----------
DS326  ---------- ---------- ---------- ---------- ---------- -N--------
E/Del  ---------- ---------- ---------- ---------- ---------- -N--------
D78    ---------- ---------- ---------- ---------- ---------- -N--------
Cu-1   ---------- ---------- ---------- ---------- ---------- -N--------
PBG98  ---------- ---------- ---------- ---------- ---------- -N--------
52/70  ---------- ---------- ----S----- ------D--- ---------- -N--S-----
STC    ---------- ---------- ---------- ---------- ---------- -N--------
002-73 ---------- ---------- ---T--F--- ---------- ----D----- -D--------
OH     ---------G ---------- ---T--F-L- ---------- ----D----- -D--NA----

70         80         90        100        110
             |          |          |          |          |
       LFQSALSVFM WLEENGIVTD MANFALSDPN AHRMRNFLAN APQAGSKSQR AKYGTAGYGV - 840
GLS    ---------- ---------- ---------- ---------- ---------- ----------
DS326  ---------- -A-------- ---------- ---------- ---------- ----------
E/Del  ---------- ---------- ---------- ---------- ---------- ----------
D78    ---------- ---------- ---------- ---------- ---------- ----------
Cu-1   ---------- ---------- ---------- ---------- ---------- ----------
PBG98  ---------- ---------- ---------- ---------- ---------- ----------
52/70  ---------- ---------- --T------- ---------- ---------- ----------
STC    ---------- ---------- ---------- ---------- ---------- ----------
002-73 ---------- ---------- ---------- ---------- ---------- ----------
OH     --R---Q--- ---------- ---------- ----K----- ---------- ----------
```

FIG. 3H

```
                    10         20         30         40         50         60
                    |          |          |          |          |          |
GLS        EARGPTPEEA QREKDTRISK KMETMGIYFA TPEWVALNGH RGPSPGQLKY WQNTREIPDP
DS326      ---------- ---------- ---------- ---------- ---------- ----------
E/Del      ---------- ---------- ---------- ---------- ---------- ----------
D78        ---------- ---------- ---------- ---------- ---------- ----------
Cu-1       ---------- ---------- ---------- ---------- ---------- ----------
PBG98      ---------K ---------- ---------- ---------- ---------- ----------
52/70      ---------- --A------- ---------- ---------- -------A-- ----------
STC        ---------- ---------- ---------A ---------- ---------- ----------
002-73     ---------- ---------- ---------- ---------- ---------- ----------
OH         ---------- --A--A---- ---------- ---------- ---------- -------E--

70         80         90         100        110
                    |          |          |          |          |
           NEDYLDYVHA EKSRLASEEQ ILRAATSIYG APGQAEPPQA FIDEVAKVYE INHGRGPNQE  - 960
           ---------- ---------- ------K--- ---------- ---------- ----------
           ---------- ---------- ---------- ---------- ---------- ---------G
           ---------- -----D---- ---------- ---------- ---------- ----------
           ---------- ---------- ------K--- ---------- ---------- ----------
           ---------- ---------- ---------- ---------- ---------- ----------
           ---------- ---------- ---------- ---------- ---------- ----------
           ---------- ---------- ---------- ---------- ----R----- ----------
           ---------- ---------- ---------- ---------- ---------- ----------
           ---P------ ---------- ---------- ---------- ----R--T-- -------V--
```

FIG. 5A

```
*******************************************
* TRANSLATION OF A NUCLEIC ACID SEQUENCE *
*******************************************

Done on large genome segment A of GLS-IBDV.

DE  From cDNA clones pGLS-1 to pGLS-4.

Total number of bases is: 3230.
Analysis done on bases 114 to 3152.
Done on (absolute) phase(s): 3.
Using the Universal genetic code.

CC CCG
      10          20          30          40          50
       |           |           |           |           |
GGG GAG TCA CCC GGG GAC AGG CCG TCA AGG CCT TGT TCC AGG ATG GAA CTC CCC 60          70          80          90         100         110
|           |           |           |           |           |
CTT CTA CAA TGC TAT CAT TGA TGG TTA GTA GAG ATC GGA CAA ACG ATC GCA GCG 120         130         140         150         160
          |           |           |           |           |
ATG ACA AAC CTG CAA GAT CAA ACC CAA CAG ATT GTT CCG TTC ATA CGG AGC CTT
MET Thr Asn Leu Gln Asp Gln Thr Gln Gln Ile Val Pro Phe Ile Arg Ser Leu
VP2
```

```
         170               180               190               200               210
          |                 |                 |                 |                 |
         CTG ATG CCA ACA ACC GGA CCG GCG TCC ATT CCG GAC GAC ACC CTG GAG AAG CAC
         Leu MET Pro Thr Thr Gly Pro Ala Ser Ile Pro Asp Asp Thr Leu Glu Lys His 230               240               250               260               270
               |                 |                 |                 |                 |
              ACT CTC AGG TCA GAG ACC TCG ACC TAC AAT TTG ACT GTG GGG GAC ACA GGG TCA
              Thr Leu Arg Ser Glu Thr Ser Thr Tyr Asn Leu Thr Val Gly Asp Thr Gly Ser 280               290               300               310               320
          |                 |                 |                 |                 |
         GGG CTA ATT GTC TTT TTC CCT GGA TTC CCT GGC TCA ATT GTG GGT GCT CAC TAC
         Gly Leu Ile Val Phe Phe Pro Gly Phe Pro Gly Ser Ile Val Gly Ala His Tyr 340               350               360               370               380
               |                 |                 |                 |                 |
              ACA CTG CAG AGC AAT GGG AAC TAC AAG TTC GAT CAG ATG CTC CTG ACT GCC CAG
              Thr Leu Gln Ser Asn Gly Asn Tyr Lys Phe Asp Gln MET Leu Leu Thr Ala Gln 390               400               410               420               430
          |                 |                 |                 |                 |
         AAC CTA CCG GCC AGC TAC AAC TAC TGC AGG CTA GTG AGT CGG AGT CTC ACA GTA
         Asn Leu Pro Ala Ser Tyr Asn Tyr Cys Arg Leu Val Ser Arg Ser Leu Thr Val 450               460               470               480               490
               |                 |                 |                 |                 |
              AGG TCA AGC ACA CTC CCT GGT GGC GTT TAT GCA CTA AAC GGC ACC ATA AAC GCC
              Arg Ser Ser Thr Leu Pro Gly Gly Val Tyr Ala Leu Asn Gly Thr Ile Asn Ala
```

*FIG. 5B*

```
         500             510             520             530             540
          |               |               |               |               |
GTG ACC TTC CAA GGA AGC CTG AGT GAA CTG ACA GAT GTT AGC TAC AAT GGG TTG
Val Thr Phe Gln Gly Ser Leu Ser Glu Leu Thr Asp Val Ser Tyr Asn Gly Leu 550             560             570             580             590
          |               |               |               |               |
ATG TCT GCA ACA GCC AAC ATC AAC GAC AAA ATT GGG AAC GTC CTA GTA GGG GAA
MET Ser Ala Thr Ala Asn Ile Asn Asp Lys Ile Gly Asn Val Leu Val Gly Glu 600             610             620             630             640             650
          |               |               |               |               |               |
GGG GTT ACT GTC CTC AGC TTA CCC ACA TCA TAT GAT CTT GGG TAT GTG AGG CTT
Gly Val Thr Val Leu Ser Leu Pro Thr Ser Tyr Asp Leu Gly Tyr Val Arg Leu 660             670             680             690             700
          |               |               |               |               |
GGT GAC CCC ATA CCC GCT ATA GGG CTT GAC AAA ATG GTA GCA ACA TGT GAC
Gly Asp Pro Ile Pro Ala Ile Gly Leu Asp pPro Lys MET Val Ala Thr Cys Asp 710             720             730             740             750             760
          |               |               |               |               |               |
AGC AGT GAC AGG CCC AGA GTC TAC ACC ATA ACT GCA GCT GAT GAT TAC CAA TTC
Ser Ser Asp Arg Pro Arg Val Tyr Thr Ile Thr Ala Ala Asp Asp Tyr Gln Phe 770             780             790             800             810
          |               |               |               |               |
TCA TCA CAG TAC CAA ACA GGT GGG GTA ACA ATC ACC CTG TTC TCA GCC AAC ATT
Ser Ser Gln Tyr Gln Thr Gly Gly Val Thr Ile Thr Leu Phe Ser Ala Asn Ile
```

```
820                830              840              850              860
 —                  —                —                —                —
GAT GCC ATC ACA AGC CTC AGC GTT GGG GGA GAG CTC GTG TTT AAA ACA AGC GTC
Asp Ala Ile Thr Ser Leu Ser Val Gly Gly Glu Leu Val Phe Lys Thr Ser Val 870                880              890              900              910              920
 —                  —                —                —                —                —
CAC AGC CTT GTA CTG GGC GCC ACC ATC TAC CTT ATA GGC TTT GAT GGG TCT GCG
His Ser Leu Val Leu Gly Ala Thr Ile Tyr Leu Ile Gly Phe Asp Gly Ser Ala 930                940              950              960              970
 —                  —                —                —                —
GTA ATC ACT AGA GCT GTG GCC GCA AAC AAT GGG CTG ACG ACC GGC ACC GAC AAT
Val Ile Thr Arg Ala Val Ala Ala Asn Asn Gly Leu Thr Thr Gly Thr Asp Asn 980                990              1000             1010             1020             1030
 —                  —                —                —                —                —
CTT ATG CCA TTC AAT CTT GTG ATT CCA ACC AAC GAG ATA ACC CAG CCA ATC ACA
Leu MET Pro Phe Asn Leu Val Ile Pro Thr Asn Glu Ile Thr Gln Pro Ile Thr 1040               1050             1060             1070             1080
 —                  —                —                —                —
TCC ATC AAA CTG GAG ATA GTG ACC TCC AAA AGT GGT CAG GAA GGG GAC CAG
Ser Ile Lys Leu Glu Ile Val Thr Ser Lys Ser Gly Gln Glu Gly Asp Gln 1090               1100             1110             1120             1130
 —                  —                —                —                —
ATG TCA TGG TCG GCA AGT GGG AGC CTA GCA GTG ACG ATT CAT GGT GGC AAC TAT
MET Ser Trp Ser Ala Ser Gly Ser Leu Ala Val Thr Ile His Gly Gly Asn Tyr
```

FIG. 5E

```
1140                1150            1160            1170            1180            1190
 |                   |               |               |               |               |
CCA GGG GCC CTC CGT CCC GTC ACA CTA GCC TAC GAA AGA GTG GCA ACA GGA
Pro Gly Ala Leu Arg Pro Val Thr Leu Val Ala Tyr Glu Arg Val Ala Thr Gly 1200            1210            1220            1230            1240
     |               |               |               |               |
TCT GTC GTT ACG GTC GCT GGG GTG AGC AAC TTC GAG CTG ATC CCA AAT CCT GAA
Ser Val Val Thr Val Ala Gly Val Ser Asn Phe Glu Leu Ile Pro Asn Pro Glu 1250            1260            1270            1280            1290            1300
 |               |               |               |               |               |
CTA GCA AAG AAC CTG GTT ACA GAA TAC GGC CGA TTT GAC CCA GGA GCC ATG AAC
Leu Ala Lys Asn Leu Val Thr Glu Tyr Gly Arg Phe Asp Pro Gly Ala MET Asn 1310            1320            1330            1340            1350
     |               |               |               |               |
TAC ACA AAA TTG ATA CTG AGT GAG GAC CGC CTT GGC ATC AAG ACA GTC TGG
Tyr Thr Lys Leu Ile Leu Ser Glu Asp Arg Leu Gly Ile Lys Thr Val Trp 1360            1370            1380            1390            1400
 |               |               |               |               |
CCG ACA AGG GAG TAC ACC GAC TTT CGT GAG TAC TTC ATG GAG GTG GCC GAC CTC
Pro Thr Arg Glu Tyr Thr Asp Phe Arg Glu Tyr Phe MET Glu Val Ala Asp Leu 1410            1420            1430            1440            1450            1460
 |               |               |               |               |               |
AGC TCT CCC CTG AAG ATT GCA GGA GCA TTT GGC TTC AAA GAC ATA ATC CGG GCC
Ser Ser Pro Leu Lys Ile Ala Gly Ala Phe Gly Phe Lys Asp Ile Ile Arg Ala
```

FIG. 5F

```
        1470           1480           1490           1500           1510
          |              |              |              |              |
ATA AGG|AGG ATA GCT GTG CCG GTG GTC TCC ACA TTG TTC CCA CCT GCC GCT CCC
Ile Arg|Arg Ile Ala Val Pro Val Val Ser Thr Leu Phe Pro Pro Ala Ala Pro
       VP4

1520           1530           1540           1550           1560           1570
     |              |              |              |              |              |
CTG GCC CAT GCA ATT GGG GAA GGT GTA GAC TAC CTG CTG GGT GAT GAG GCA CAG
Leu Ala His Ala Ile Gly Glu Gly Val Asp Tyr Leu Leu Gly Asp Glu Ala Gln 1580           1590           1600           1610           1620
     |              |              |              |              |
GCT GCT TCA GGA ACT GCT CGA GCC GCG TCA GGA AAA GCA AGG GCT GCC TCA GGC
Ala Ala Ser Gly Thr Ala Arg Ala Ala Ser Gly Lys Ala Arg Ala Ala Ser Gly 1630           1640           1650           1660           1670
     |              |              |              |              |
CGC ATA AGG CAG CTG ACT CTC GCC GCC GAC AAG GGG TAC GAG GTA GTC GCG AAT
Arg Ile Arg Gln Leu Thr Leu Ala Ala Asp Lys Gly Tyr Glu Val Val Ala Asn 1680           1690           1700           1710           1720           1730
     |              |              |              |              |              |
CTA TTC CAG GTG CCC CAG AAT CCC GTA GTC GAC GGG ATT CTT GCT TCA CCC GGG
Leu Phe Gln Val Pro Gln Asn Pro Val Val Asp Gly Ile Leu Ala Ser Pro Gly 1740           1750           1760           1770           1780
     |              |              |              |              |
ATA CTC CGC GGT GCA CAC AAC CTC AAC TTG GAC TGC GTG TTA AGA GAG GCC ACG CTA
Ile Leu Arg Gly Ala His Asn Leu Asn Leu Asp Cys Val Leu Arg Glu Ala Thr Leu
```

```
1790                1800              1810              1820              1830              1840
 |                   |                 |                 |                 |                 |
TTC CCT GTG GTC ATC ACG ACA GTG GAA GAC GCC ATG ACA CCC AAA GCA CTA AAC
Phe Pro Val Val Ile Thr Thr Val Glu Asp Ala MET Thr Pro Lys Ala Leu Asn 1850              1860              1870              1880              1890
                |                 |                 |                 |                 |
AGC AAA ATG TTT GCT GTC ATT GAA GGC GTG CGA GAG GAC CTC CAA CCT CCA TCT
Ser Lys MET Phe Ala Val Ile Gly Gly Val Arg Glu Asp Leu Gln Pro Pro Ser 1900              1910              1920              1930              1940
 |                 |                 |                 |                 |
CAA AGA GGA TCC TTC ATA CGA ACT CTC TCC GGA CAC AGA GTC TAT GGA TAT GCT
Gln Arg Gly Ser Phe Ile Arg Thr Leu Ser Gly His Arg Val Tyr Gly Tyr Ala 1950              1960              1970              1980              1990              2000
 |                 |                 |                 |                 |                 |
CCA GAT GGG GTA CTT CCA CTG GAG ACT GGG AGA GAC TAC ACC GTT GTC CCA ATA
Pro Asp Gly Val Leu Pro Leu Glu Thr Gly Arg Asp Tyr Thr Val Val Pro Ile 2010              2020              2030              2040              2050
                |                 |                 |                 |                 |
GAT GAT GTC TGG GAC GAC AGC ATT ATG CTG TCC AAA GAC CCC ATA CCT CCT ATT
Asp Asp Val Trp Asp Asp Ser Ile MET Leu Ser Lys Asp Pro Ile Pro Pro Ile 2060              2070              2080              2090              2100              2110
 |                 |                 |                 |                 |                 |
GTG GGA AAC AGT GGA AAC CTA GCC ATA GCT TAC ATG GAT GTG TTT CGA CCC AAA
Val Gly Asn Ser Gly Asn Leu Ala Ile Ala Tyr MET Asp Val Phe Arg Pro Lys
```

```
     2120           2130           2140           2150           2160
      |              |              |              |              |
GTC CCC ATC CAT GTG GCC ATG ACG GGA GCC CTC AAC GCT TGT GGC GAG ATT GAG
Val Pro Ile His Val Ala MET Thr Gly Ala Leu Asn Ala Cys Gly Glu Ile Glu 2170           2180           2190           2200           2210
      |              |              |              |              |
AAA ATA AGC TTT AGA AGC ACC AAG CTC GCC GCA CAC CGG CTT GGC CTC AAG
Lys Ile Ser Phe Arg Ser Thr Lys Leu Ala Ala His Arg Leu Gly Leu Lys 2220           2230           2240           2250           2260           2270
      |              |              |              |              |              |
TTG GCT GGT CCC GGA GCA TTT GAT GTA AAC ACC GGG CCC AAC TGG GCA ACG TTC
Leu Ala Gly Pro Gly Ala Phe Asp Val Asn Thr Gly Pro Asn Trp Ala Thr Phe 2280           2290           2300           2310           2320
      |              |              |              |              |
ATC AAA|CGT TTC CCT CAC AAT CCA CGC GAC TGG GAC AGG CTC CCC TAC CTC AAC
Ile Lys|Arg Phe Pro His Asn Pro Arg Asp Trp Asp Arg Leu Pro Tyr Leu Asn
       VP3

2330           2340           2350           2360           2370           2380
      |              |              |              |              |              |
CTT CCA TAC CTT CCA CCC AAT GCA GGA CTC CAG TAC CAC CTC GCC ATG GCC GCA
Leu Pro Tyr Leu Pro Pro Asn Ala Gly Leu Gln Tyr His Leu Ala MET Ala Ala 2390           2400           2410           2420           2430
      |              |              |              |              |
TCA GAG TTC AAG GAG ACC CCT GAA CTC GAG AGC GCC GTC AGG GCC ATG GAA GCA
Ser Glu Phe Lys Glu Thr Pro Glu Leu Glu Ser Ala Val Arg Ala MET Glu Ala
```

```
2440                  2450                  2460                  2470                  2480
 |                    |                    |                    |                    |
GCA GCC AGT GTA GAC CCA CTG TTC CAA TCT GCA CTC AGT GTG TTC ATG TGG CTG
Ala Ala Ser Val Asp Pro Leu Phe Gln Ser Ala Leu Ser Val Phe MET Trp Leu 2490                  2500                  2510                  2520                  2530                  2540
 |                    |                    |                    |                    |                    |
GAA GAG AAT GGG ATT GTG ACT GAC ATG GCC AAC TTC GCA CTC AGC GAC CCG AAC
Glu Glu Asn Gly Ile Val Thr Asp MET Ala Asn Phe Ala Leu Ser Asp Pro Asn 2550                  2560                  2570                  2580                  2590
 |                    |                    |                    |                    |
GCC CAT CGG ATG CGA AAC TTT CTT GCA AAC GCA CCA CAA GCA GGT AGC AAG TCT
Ala His Arg MET Arg Asn Phe Leu Ala Asn Ala Pro Gln Ala Gly Ser Lys Ser 2600                  2610                  2620                  2630                  2640                  2650
 |                    |                    |                    |                    |                    |
CAA AGG GCC AAA TAC GGG ACA GCA GGC TAC GGA GTG GAG GCC CGG GGC CCC ACA
Gln Arg Ala Lys Tyr Gly Thr Ala Gly Tyr Gly Val Glu Ala Arg Gly Pro Thr 2660                  2670                  2680                  2690                  2700
 |                    |                    |                    |                    |
CCA GAA GAA GCA CAG AGG GAA AAA GAC ACA CGG ATC TCA AAG AAG ATG GAG ACC
Pro Glu Glu Ala Gln Arg Glu Lys Asp Thr Arg Ile Ser Lys Lys MET Glu Thr 2710                  2720                  2730                  2740                  2750
 |                    |                    |                    |                    |
ATG GGC ATC TAC TTT GCA ACA CCA GAA TGG GTA GCA CTC AAT GGG CAC CGA GGG
MET Gly Ile Tyr Phe Ala Thr Pro Glu Trp Val Ala Leu Asn Gly His Arg Gly
```

```
2760
     CCA AGC CCC GGC CAG CTA AAG TAC TGG CAG AAC ACA CGA GAA ATA CCG GAC CCA
     Pro Ser Pro Gly Gln Leu Lys Tyr Trp Gln Asn Thr Arg Glu Ile Pro Asp Pro
         2770        2780        2790        2800        2810

AAC GAG GAC TAT CTA GAC TAC GTG CAT GCA GAG AAG AGC CGG TTG GCA TCA GAA
     Asn Glu Asp Tyr Leu Asp Tyr Val His Ala Glu Lys Ser Arg Leu Ala Ser Glu
         2820        2830        2840        2850        2860

2870
     GAA CAA ATC CTA AGG GCA GCT ACG TCG ATC TAC GGG GCT CCA GGA CAG GCA GAG
     Glu Gln Ile Leu Arg Ala Ala Thr ser Ile Tyr Gly Ala Pro Gly Gln Ala Glu
         2880        2890        2900        2910        2920

CCA CCC CAA GCT TTC ATA GAC GAA GTT GCC AAA GTC TAT GAA ATC AAC CAT GGA
     Pro Pro Gln Ala Phe Ile Asp Glu Val Ala Lys Val Tyr Glu Ile Asn His Gly
         2930        2940        2950        2960        2970

CGT GGC CCA AAC CAA GAA CAG ATG CAA GAT CTG CTC TTG ACT GCG ATG GAG ATG
     Arg Gly Pro Asn Gln Glu Gln MET Lys Asp Leu Leu Leu Thr Ala MET Glu MET
         2980        2990        3000        3010        3020

3030
     AAG CAT CGC AAT CCC AGG CGG GCT CCA CCA AAG CCC AGA CCC AAC GCT
     Lys His Arg Asn Pro Arg Arg Ala Pro Pro Lys Pro Arg Pro Asn Ala
         3040        3050        3060        3070        3080
```

```
                    3090          3100          3110          3120          3130
                      |             |             |             |             |
CCA ACG CAG AGA CCC CCT GGT CGG CTG GGC CGC TGG ATC AGG ACT GTC TCT GAT
Pro Thr Gln Arg Pro Pro Gly Arg Leu Gly Arg Trp Ile Arg Thr Val Ser Asp 3140          3150          3160          3170          3180          3190
    |             |             |             |             |             |
GAG GAC CTT GAG TGA GGC TCC TGG GAG TCT CCC GAC ACC CGC GCA GGC GTG
Glu Asp Leu Glu ---

3200          3210          3220          3230
           |             |             |             |
GAC ACC AAT TCG GCC TTA CAA CAT CCC AAA TTG GAT CCG
----2 Aug - 1990 -----------------------------PC/Gene----
```

```
**************************************
* TRANSLATION OF A NUCLEIC ACID SEQUENCE *
**************************************

Done on DNA sequence EDEL22.

DE      E/DEL virus, vero cells adapted

Total number of bases is: 3180.
Analysis done on the complete sequence.
Done on (absolute) phase(s): 1.
Using the Universal genetic code.
```

```
         10          20          30          40          50
         |           |           |           |           |
GAA TTC CTC CTT CTA CAA AAC CTG CAA GAT CAA ACC CAC CAG ATT GTT CCG TTC ATA
                                                                             ---

60          70          80          90         100
                            |           |           |           |           |
ATC GCA GCG|ATG ACA AAC CTG CAA GAT CAA ACC CAC CAG ATT GTT CCG TTC ATA
---  ---  ---|MET Thr Asn Leu Gln Asp Gln Thr His Gln Ile Val Pro Phe Ile
            VP2

110         120         130         140         150         160
 |           |           |           |           |           |
CGG AGC CTT CTG ATG CCA ACA ACC GGA CCG GCG TCC ATT CCG GAC GAC ACC CTG
Arg Ser Leu Leu MET Pro Thr Thr Gly Pro Ala Ser Ile Pro Asp Asp Thr Leu
```

```
      170            180            190            200            210
       |              |              |              |              |
GAG AAG CAC ACT CTC AGG TCA GAG ACC TCG ACC TAC AAT TTG ACT GTG GGG GAC
Glu Lys His Thr Leu Arg Ser Glu Thr Ser Thr Tyr Asn Leu Thr Val Gly Asp 220            230            240            250            260            270
       |              |              |              |              |              |
ACA GGG TCA GGG CTA ATT GTC TTT TTC CCT GGA TTC CCT GGC TCA ATT GTG GGT
Thr Gly Ser Gly Leu Ile Val Phe Phe Pro Gly Phe Pro Gly Ser Ile Val Gly 280            290            300            310            320
       |              |              |              |              |
GCT CAC TAC ACA CTG CAG AGC AGT GGG AAC TAC AAG TTC GAT CAG ATG CTC CTG
Ala His Tyr Thr Leu Gln Ser Ser Gly Asn Tyr Lys Phe Asp Gln MET Leu Leu 330            340            350            360            370
       |              |              |              |              |
ACT GCC CAG AAC CTA CCG GCC AGC TAC AAC TAC TGC AGG CTA GTG AGT CGG AGT
Thr Ala Gln Asn Leu Pro Ala Ser Tyr Asn Tyr Cys Arg Leu Val Ser Arg Ser 380            390            400            410            420            430
       |              |              |              |              |              |
CTC ACA GTA AGG TCA AGC ACA CTC CCT GGT GGC GTT TAT GCA CTA AAC GGC ACC
Leu Thr Val Arg Ser Ser Thr Leu Pro Gly Gly Val Tyr Ala Leu Asn Gly Thr
```

*FIG. 6B*

```
        440                450                460                470                480
         |                  |                  |                  |                  |
ATA AAC GCC GTG ACC TTC CAA GGA AGC CTG AGT GAA CTG ACA GAT GTT AGC TAC
Ile Asn Ala Val Thr Phe Gln Gly Ser Leu Ser Glu Leu Thr Asp Val Ser Tyr 490                500                510                520                530                540
         |                  |                  |                  |                  |                  |
AAC GGG TTG ATG TCT GCA ACA GCC AAC ATC AAC GAC AAA ATT GGG AAC GTC CTA
Asn Gly Leu MET Ser Ala Thr Ala Asn Ile Asn Asp Lys Ile Gly Asn Val Leu 550                560                570                580                590
         |                  |                  |                  |                  |
GTA GGG GAA GGG GTA ACC GTC CTC AGC TTA CCC ACA TCA TAT GAT CTT GGG TAT
Val Gly Glu Gly Val Thr Val Leu Ser Leu Pro Thr Ser Tyr Asp Leu Gly Tyr 600                610                620                630                640
         |                  |                  |                  |                  |
GTG AGG CTT GGT GAC CCC ATA GGG CTT GAC CCA AAA ATG GTA GCA
Val Arg Leu Gly Asp Pro Ile Gly Leu Asp Pro Lys MET Val Ala 650                660                670                680                690                700
         |                  |                  |                  |                  |                  |
ACA TGT GAC AGC AGT GAC AGG CCC AGA GTC TAC ACC ATA ACT GCA GCC GAT AAT
Thr Cys Asp Ser Ser Asp Arg Pro Arg Val Tyr Thr Ile Thr Ala Ala Asp Asn
```

FIG. 6C

```
                    710             720             730             740             750
                    |               |               |               |               |
TAC CAA TTC TCA TCA CAG TAC CAA ACA GGT GTA ACA ATC ACA CTG TTC TCA
Tyr Gln Phe Ser Ser Gln Tyr Gln Thr Gly Val Thr Ile Thr Leu Phe Ser 760             770             780             790             800             810
    |               |               |               |               |               |
GCC AAC ATT GAT GCC ATC ACA AGT CTC AGC GTT GGG GGA GAG CTC GTG TTC AAA
Ala Asn Ile Asp Ala Ile Thr Ser Leu Ser Val Gly Gly Glu Leu Val Phe Lys 820             830             840             850             860
        |               |               |               |               |
ACA AGC GTC CAA AGC CTT GTA CTG GGC GCC ACC ATC TAC CTT ATA GGC TTT GAT
Thr Ser Val Gln Ser Leu Val Leu Gly Ala Thr Ile Tyr Leu Ile Gly Phe Asp 870             880             890             900             910
    |               |               |               |               |
GGG ACT GCG GTA ATC ACC AGA GCT GTG GCC GCA AAC AAT GGG CTG ACG GCC GGC
Gly Thr Ala Val Ile Thr Arg Ala Val Ala Ala Asn Asn Gly Leu Thr Ala Gly 920             930             940             950             960             970
|               |               |               |               |               |
ATC GAC AAT CTT ATG CCA TTC AAT CTT GTG ATT CCA ACC AAT GAG ATA ACC CAG
Ile Asp Asn Leu MET Pro Phe Asn Leu Val Ile Pro Thr Asn Glu Ile Thr Gln
```

*FIG. 6D*

```
      980             990            1000           1010           1020          1030
       |               |               |              |              |             |
CCA ATC ACA TCC ATC ATA CTG GAG ATA GTG ACC TCC AAA AGT GAT GGT CAG GCA
Pro Ile Thr Ser Ile Ile Leu Glu Ile Val Thr Ser Lys Ser Asp Gly Gln Ala 1030            1040           1050           1060           1070          1080
       |               |               |              |              |             |
GGG GAA CAG ATG TCA TGG TCG GCA AGT GGG AGC CTA GCA GTG CTA ACG ATC CAT GGT
Gly Glu Gln MET Ser Trp Ser Ala Ser Gly Ser Leu Ala Val Thr Ile His Gly 1090            1100           1110           1120           1130
       |               |               |              |              |
GGC AAC TAT CCA GGA GCC CTC CGT CCC GTC ACA CTA GTG GCC TAC GAA AGA GTG
Gly Asn Tyr Pro Gly Ala Leu Arg Pro Val Thr Leu Val Ala Tyr Glu Arg Val 1140            1150           1160           1170           1180
       |               |               |              |              |
GCA ACA GGA TCT GTC GTT ACG GTC GCT GGG GTG AGC AAC TTC GAG CTG ATC CCA
Ala Thr Gly Ser Val Val Thr Val Ala Gly Val Ser Asn Phe Glu Leu Ile Pro 1190            1200           1210           1220           1230          1240
       |               |               |              |              |             |
AAT CCT GAA CTA GCA AAG AAC CTG GTT ACA GAA TAC GGC CGA TTT GAC CCA GGA
Asn Pro Glu Leu Ala Lys Asn Leu Val Thr Glu Tyr Gly Arg Phe Asp Pro Gly
```

```
       1250            1260            1270            1280            1290
        |               |               |               |               |
GCC ATG AAC TAC ACG AAA TTG ATA CTG AGT GAG AGG GAC CAC CTT GGC ATC AAG
Ala MET Asn Tyr Thr Lys Leu Ile Leu Ser Glu Arg Asp His Leu Gly Ile Lys 1300            1310            1320            1330            1340            1350
        |               |               |               |               |               |
ACC GTC TGG CCA ACA AGG GAG TAC ACT GAC TTT CGT GAG TAC TTC ATG GAG GTG
Thr Val Trp Pro Thr Arg Glu Tyr Thr Asp Phe Arg Glu Tyr Phe MET Glu Val 1360            1370            1380            1390            1400
        |               |               |               |               |
GCC GAC CTC AAC TCT CCC CTG AAG ATT GCA GGA GCA TTT GGC TTC AAA GAG ATA
Ala Asp Leu Asn Ser Pro Leu Lys Ile Ala Gly Ala Phe Gly Phe Lys Asp Ile 1410            1420            1430            1440            1450
        |               |               |               |               |
ATC CGG GCC ATA AGG|AGG ATA GCT GTA CCG GTG GTC TCT ACA TTG TTC CCA CCT
Iel Arg Ala Ile Arg|Arg Ile Ala Val Pro Val Val Ser Thr Leu Phe Pro Pro
                VP4

1460            1470            1480            1490            1500            1510
        |               |               |               |               |               |
GCC GCT CCT CTA GCC CAT GCA ATT GGG GAA GGT GTA GAC TAC CTA CTG GGC GAT
Ala Ala Pro Leu Ala His Ala Ile Gly Glu Gly Val Asp Tyr Leu Leu Gly Asp
```

```
1520          1530          1540          1550          1560
 |             |             |             |             |
GAG GCA CAG GCT GCT TCA GGA ACC GCT CGA GCC GCG TCA GGA AAA GCA AGG GCT
Glu Ala Gln Ala Ala Ser Gly Thr Ala Arg Ala Ala Ser Gly Lys Ala Arg Ala 1570          1580          1590          1600          1610          1620
 |             |             |             |             |             |
GCC TCA GGC CGC ATA AGG CAG CTG ACT CTC GCC GCC GAC AAG GGG TAC GAG GTA
Ala Ser Gly Arg Ile Arg Gln Leu Thr Leu Ala Ala Asp Lys Gly Tyr Glu Val 1630          1640          1650          1660          1670
 |             |             |             |             |
GTC GCG AAT CTA TTC CAG GTG CCC CAG AAT CCC GTA GTC GAC GGG ATT CTT GCT
Val Ala Asn Leu Phe Gln Val Pro Gln Asn Pro Val Val Asp Gly Ile Leu Ala 1680          1690          1700          1710          1720
 |             |             |             |             |
TCA CCC GGG ATA CTT CGC GGT GCA CAC AAC CTC GAC TGC GTG CTA AGA GAG GGT
Ser Pro Gly Ile Leu Arg Gly Ala His Asn Leu Asp Cys Val Leu Arg Glu Gly 1730          1740          1750          1760          1770          1780
 |             |             |             |             |             |
GCC ACG CTA TTC CCT GTG GTC ATT ACG ACA GTG GAA GAC GCC ATG ACA CCC AAA
Ala Thr Leu Phe Pro Val Val Ile Thr Thr Val Glu Asp Ala MET Thr Pro Lys
```

*FIG. 6G*

```
      1790        1800        1810        1820        1830
       |           |           |           |           |
GCA CTG AAC AGC AAA ATG TTT GCT GTC ATT GAA GGC GTG CGA GAA GAC CTC CAA
Ala Leu Asn Ser Lys MET Phe Ala Val Ile Glu Gly Val Arg Glu Asp Leu Gln 1840        1850        1860        1870        1880        1890
       |           |           |           |           |           |
CCT CCA TCT CAA AGA GGA TCC TTC ATA CGA ACT CTC TCC GGA CAC AGA GTC TAT
Pro Pro Ser Gln Arg Gly Ser Phe Ile Arg Thr Leu Ser Gly His Arg Val Tyr 1900        1910        1920        1930        1940
       |           |           |           |           |
GGA TAT GCT CCA GAT GGG GTA CTT CCA CTG GAG ACT GGG AGA GAC TAC ACC GTT
Gly Tyr Ala Pro Asp Gly Val Leu Pro Leu Glu Thr Gly Arg Asp Tyr Thr Val 1950        1960        1970        1980        1990
       |           |           |           |           |
GTC CCA ATA GAT GAT GTC TGG GAC GAC AGC ATT ATG CTG TCC AAG GAC CCC ATA
Val Pro Ile Asp Asp Val Trp Asp Asp Ser Ile MET Leu Ser Lys Asp Pro Ile 2000        2010        2020        2030        2040        2050
       |           |           |           |           |           |
CCT CCT ATT GTG GGA AAC AGT GGA AAC CTA GCC ATA GCT TAC ATG GAT GTG TTT
pro Pro Ile Val Gly Asn Ser Gly Asn Leu Ala Ile Ala Tyr MET Asp Val Phe
```

```
     2060                 2070                 2080                 2090                 2100
      |                    |                    |                    |                    |
CGA CCC AAA GTC CCC ATC CAT GTG GCC ATG ACG GGA GCC CTC AAC GCT TGT GGC
Arg Pro Lys Val Pro Ile His Val Ala Met Thr Gly Ala Leu Asn Ala Cys Gly 2110                 2120                 2130                 2140                 2150                 2160
      |                    |                    |                    |                    |                    |
GAG ATT GAG AAA ATA AGC TTC AGA AGC ACC AAG CTC GCC ACC GCA CAC CGG CTT
Glu Ile Glu Lys Ile Ser Phe Arg Ser Thr Lys Leu Ala Thr Ala His Arg Leu 2170                 2180                 2190                 2200                 2210
      |                    |                    |                    |                    |
GGC CTC AAG TTG GCT GGT CCC GGA GCA TTC GAT GTA AAC ACC GGG CCC AAC TGG
Gly Leu Lys Leu Ala Gly Pro Gly Ala Phe Asp Val Asn Thr Gly Pro Asn Trp 2220                 2230         |        2240                 2250                 2260
      |                    |           |         |                    |                    |
GCA ACG TTC ATC AAA CGT TTC CCT CAC AAT CCA CGC GAC TGG GAC AGG CTC CCC
Ala Thr Phe Ile Lys Arg Phe Pro His Asn Pro Arg Asp Trp Asp Arg Leu Pro
                       VP3

2270                 2280                 2290                 2300                 2310                 2320
      |                    |                    |                    |                    |                    |
TAC CTC AAC CTT CCA TAC CTT CCA CCC AAT GCA GGA CGC CAG TAC CAC CTT GCC
Tyr Leu Asn Leu Pro Tyr Leu Pro Pro Asn Ala Gly Arg Gln Tyr His Leu Ala
```

```
2330                2340                2350                2360                2370
 |                   |                   |                   |                   |
ATG GCT GCA TCA GAG TTT AAA GAG ACC CCT GAA CTC GAG AGC GCC GTC AGA GCC
MET Ala Ala Ser Glu Phe Lys Glu Thr Pro Glu Leu Glu Ser Ala Val Arg Ala 2380                2390                2400                2410                2420                2430
      |                   |                   |                   |                   |                   |
ATG GAA GCA GCA GCC AAT GTG GAC CCA CTG TTC CAA TCT GCA CTC AGT GTG TTC
MET Glu Ala Ala Ala Asn Val Asp Pro Leu Phe Gln Ser Ala Leu Ser Val Phe 2440                2450                2460                2470                2480
      |                   |                   |                   |                   |
ATG TGG CTG GAA GAG AAT GGG ATT GTG GCT GAC ATG GCC AAT TTC GCA CTC AGC
MET Trp Leu Glu Glu Asn Gly Ile Val Ala Asp MET Ala Asn Phe Ala Leu Ser 2490                2500                2510                2520                2530
      |                   |                   |                   |                   |
GAC CCG AAC GCC CAT CGG ATG CGA AAT TTT CTT GCA AAC GCA CCA CAA GCA GGC
Asp Pro Asn Ala His Arg MET Arg Asn Phe Leu Ala Asn Ala Pro Gln Ala Gly 2540                2550                2560                2570                2580                2590
      |                   |                   |                   |                   |                   |
AGC AAG TCG CAA AGG GCC AAG TAC GGA ACA GCA GGC TAC GGA TGT GAG GCC CGG
Ser Lys Ser Gln Arg Ala Lys Tyr Gly Thr Ala Gly Tyr Gly Val Glu Ala Arg
```

*FIG. 6J*

```
2600                2610                2620                2630                2640
 |                   |                   |                   |                   |
GGC CCC ACA CCA GAG GAA GCA CAG AGG GAA AAA GAC ACA CGG ATC TCA AAG AAG
Gly Pro Thr Pro Glu Glu Ala Gln Arg Glu Lys Asp Thr Arg Ile Ser Lys Lys 2650                2660                2670                2680                2690                2700
 |                   |                   |                   |                   |                   |
ATG GAG ACC ATG GGC ATC TAC TTT GCA ACA CCA GAA TGG GTA GCA CTC AAT GGG
MET Glu Thr MET Gly Ile Tyr Phe Ala Thr Pro Glu Trp Val Ala Leu Asn Gly 2710                2720                2730                2740                2750
             |                   |                   |                   |                   |
CAC CGA GGG CCA AGC CCC GGC CAG CTA AAG TAC TGG CAG AAC ACA CGA GAA ATA
His Arg Gly Pro Ser Pro Gly Gln Leu Lys Tyr Trp Gln Asn Thr Arg Glu Ile 2760                2770                2780                2790                2800
 |                   |                   |                   |                   |
CCG GAC CCA AAC GAG GAC TAT CTA GAC TAC GTG CAT GCA GAG AAG AGC CGG TTG
Pro Asp Pro Asn Glu Asp Tyr Leu Asp Tyr Val His Ala Glu Lys Ser Arg Leu 2810                2820                2830                2840                2850                2860
 |                   |                   |                   |                   |                   |
GCA TCA GAA GAA CAA ATC CTA AAG GCA GCT ACG TCG ATC TAC GGG GCT CCA GGA
Ala Ser Glu Glu Gln Ile Leu Lys Ala Ala Thr Ser Ile Tyr Gly Ala Pro Gly
```

FIG. 6K

```
      2870                2880                2890                2900                2910
       |                   |                   |                   |                   |
CAG GCA GAG CCA CCC CAA GCT TTC ATA GAC GAA GTT GCC AAA GTC TAT GAA ATC
Gln Ala Glu Pro Pro Gln Ala Phe Ile Asp Glu Val Ala Lys Val Tye Glu Ile 2920                2930                2940                2950                2960                2970
       |                   |                   |                   |                   |                   |
AAC CAT GGA CGT GGC CCT AAC CAA CAG GAA CAG ATG AAA GAT CTG CTC TTG ACT GCA
Asn His Gly Arg Gly Pro Asn Gln Gln Glu Gln MET Lys Asp Leu Leu Leu Thr Ala 2980                2990                3000                3010                3020
       |                   |                   |                   |                   |
ATG GAG ATG AAG CAT CGC AAC CCC AGG GCT CCA CCA AAG CCC AAA CCA AAA
MET Glu MET Lys His Arg Asn Pro Arg Ala Pro Pro Lys Pro Lys Pro Lys 3030                3040                3050                3060                3070
       |                   |                   |                   |                   |
CCC AAT GCT CCA ACA CAG AGA CCC CCT GGT CGG CTG GGC CGC TGG ATC AGG ACC
Pro Asn Ala Pro Thr Gln Arg Pro Pro Gly Arg Leu Gly Arg Trp Ile Arg Thr 3080                3090                3100                3110                3120                3130
       |                   |                   |                   |                   |                   |
GTC TCT GAT GAG GAC CTT GAG TGA GGC CCC TGG GGG TCT CCC GAC ACC ACC CGC
Val Ser Asp Glu Asp Leu Glu  ---  ---  ---  ---  ---  ---  ---  ---  ---  ---  ---
```

*FIG. 6L*

```
       3140           3150          3160          3170          3180
        |              |             |             |             |
GCA GGC GTG GAC ACC AAT TCG GCC TTA CAA CAT CCC AAA TTG GAT CCG
===24-AUG-1992=================================================PC/GENE===
```

FIG. 6M

AMINO ACID CHANGES IN VP2 VARIOUS IBDV STRAINS

FIG. 7A — AMINO ACID RESIDUE NUMBER IN VP2

| VIRUSES | 5 | 74 | 76 | 80 | 213 | 222 | 239 | 242 | 249 | 253 | 254 | 258 | 263 | 264 | 269 | 270 | 272 | 279 |
|---|---|---|---|---|---|---|---|---|---|---|---|---|---|---|---|---|---|---|
| GLS | Gln | Leu | Ser | Tyr | Asp | Thr | Ser | Val | Lys | His | Ser | Gly | Leu | Ile | Ser | Ala | Ile | Asn |
| DS326 | " | " | " | " | " | Ser | " | " | " | Gln | " | " | " | " | Thr | " | " | " |
| E/DEL | " | " | " | " | Asn | Thr | " | " | Gln | His | " | " | " | " | " | Thr | " | " |
| D78 | " | " | Gly | " | Asp | Pro | " | " | " | " | Gly | " | " | " | " | " | " | " |
| Cu-1 | " | " | Ser | " | " | " | " | Ile | Arg | Gln | " | " | " | " | " | " | " | " |
| PBG98 | " | " | " | " | " | " | " | Val | Gln | " | " | " | Phe | " | " | Ala | " | Asp |
| 52/70 | " | " | " | " | " | " | " | " | " | " | " | " | " | " | " | Ala | " | Asp |
| SIC | " | " | " | Leu | " | " | " | " | " | " | " | Asn | Leu | Val | Thr | Thr | " | " |
| 002-73 | Ser | Met | " | Tyr | " | " | Asn | " | " | " | " | " | " | " | " | " | Thr | Gly |

FIG. 7B

| VIRUSES | 280 | 284 | 286 | 299 | 305 | 311 | 312 | 318 | 320 | 321 | 323 | 326 | 328 | 330 | 332 | 433 |
|---|---|---|---|---|---|---|---|---|---|---|---|---|---|---|---|---|
| GLS | Asn | Thr | Thr | Asn | Ile | Glu | Ile | Gly | Gln | Glu | Asp | Ser | Ser | Ser | Ser | Ser |
| DS326 | " | Ala | " | " | " | Lys | " | " | Leu | " | Glu | " | " | " | " | Asn |
| E/DEL | " | " | Ile | " | " | Glu | " | Asp | Gln | Ala | Asp | " | " | Arg | " | " |
| D78 | " | Thr | Thr | Ser | " | " | " | Gly | " | " | " | " | " | Lys | " | " |
| Cu-1 | " | " | " | Pro | " | " | " | " | " | " | " | " | " | Arg | " | " |
| PBG98 | Thr | " | " | " | " | " | " | " | " | " | " | " | " | Ser | " | " |
| 52/70 | " | " | " | " | " | " | Lys | " | " | " | " | Leu | " | " | " | " |
| SIC | Asn | Ala | " | " | Val | " | Glu | " | " | " | " | Ser | Leu | " | " | " |
| 002-73 | " | " | " | Ser | " | " | " | " | " | " | " | " | " | " | Asn | " |

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1012 amino acids
        ( B ) TYPE: amino acid
        ( C ) STRANDEDNESS: unknown
        ( D ) TOPOLOGY: unknown ( i i ) MOLECULE TYPE: protein (vi) ORIGINAL SOURCE:
  (A) ORGANISM: Infectious bursal disease virus
  (B) STRAIN: GLS (xi) SEQUENCE DESCRIPTION: SEQ ID NO:1:

```
Met Thr Asn Leu Gln Asp Gln Thr Gln Gln Ile Val Pro Phe Ile Arg
 1               5                  10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
50                      55                  60

Gly Ser Ile Val Gly Ala His Tyr Thr Leu Gln Ser Asn Gly Asn Tyr
65                      70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
            115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
            195                 200                 205

Thr Ala Ala Asp Asp Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val His Ser Leu Val
                245                 250                 255

Leu Gly Ala Thr Ile Tyr Leu Ile Gly Phe Asp Gly Ser Ala Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Glu Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
```

-continued

| | 385 | | | | 390 | | | | 395 | | | | 400 | |
|---|---|---|---|---|---|---|---|---|---|---|---|---|---|---|

Ile Leu Ser Glu Arg Asp Arg Leu Gly Ile Lys Thr Val Trp Pro Thr
                405                     410                 415

Arg Glu Tyr Thr Asp Phe Arg Glu Tyr Phe Met Glu Val Ala Asp Leu
            420                     425                 430

Ser Ser Pro Leu Lys Ile Ala Gly Ala Phe Gly Phe Lys Asp Ile Ile
            435                     440                 445

Arg Ala Ile Arg Arg Ile Ala Val Pro Val Val Ser Thr Leu Phe Pro
450                     455                     460

Pro Ala Ala Pro Leu Ala His Ala Ile Gly Glu Gly Val Asp Tyr Leu
465                     470                     475                 480

Leu Gly Asp Glu Ala Gln Ala Ala Ser Gly Thr Ala Arg Ala Ala Ser
                485                     490                     495

Gly Lys Ala Arg Ala Ala Ser Gly Arg Ile Arg Gln Leu Thr Leu Ala
            500                     505                     510

Ala Asp Lys Gly Tyr Glu Val Val Ala Asn Leu Phe Gln Val Pro Gln
            515                     520                     525

Asn Pro Val Val Asp Gly Ile Leu Ala Ser Pro Gly Ile Leu Arg Gly
    530                     535                     540

Ala His Asn Leu Asp Cys Val Leu Arg Glu Gly Ala Thr Leu Phe Pro
545                     550                     555                 560

Val Val Ile Thr Thr Val Glu Asp Ala Met Thr Pro Lys Ala Leu Asn
                565                     570                 575

Ser Lys Met Phe Ala Val Ile Glu Gly Val Arg Glu Asp Leu Gln Pro
            580                     585                 590

Pro Ser Gln Arg Gly Ser Phe Ile Arg Thr Leu Ser Gly His Arg Val
    595                     600                     605

Tyr Gly Tyr Ala Pro Asp Gly Val Leu Pro Leu Glu Thr Gly Arg Asp
610                     615                     620

Tyr Thr Val Val Pro Ile Asp Asp Val Trp Asp Ser Ile Met Leu
625                     630                     635                 640

Ser Lys Asp Pro Ile Pro Pro Ile Val Gly Asn Ser Gly Asn Leu Ala
            645                     650                     655

Ile Ala Tyr Met Asp Val Phe Arg Pro Lys Val Pro Ile His Val Ala
            660                     665                     670

Met Thr Gly Ala Leu Asn Ala Cys Gly Glu Ile Glu Lys Ile Ser Phe
            675                     680                     685

Arg Ser Thr Lys Leu Ala Thr Ala His Arg Leu Gly Leu Lys Leu Ala
690                     695                     700

Gly Pro Gly Ala Phe Asp Val Asn Thr Gly Pro Asn Trp Ala Thr Phe
705                     710                     715                 720

Ile Lys Arg Phe Pro His Asn Pro Arg Asp Trp Asp Arg Leu Pro Tyr
                725                     730                 735

Leu Asn Leu Pro Tyr Leu Pro Pro Asn Ala Gly Arg Gln Tyr His Leu
            740                     745                 750

Ala Met Ala Ala Ser Glu Phe Lys Glu Thr Pro Glu Leu Glu Ser Ala
            755                     760                 765

Val Arg Ala Met Glu Ala Ala Ala Ser Val Asp Pro Leu Phe Gln Ser
    770                     775                 780

Ala Leu Ser Val Phe Met Trp Leu Glu Glu Asn Gly Ile Val Thr Asp
785                     790                     795                 800

Met Ala Asn Phe Ala Leu Ser Asp Pro Asn Ala His Arg Met Arg Asn
            805                     810                     815

```
         Phe   Leu   Ala   Asn   Ala   Pro   Gln   Ala   Gly   Ser   Lys   Ser   Gln   Arg   Ala   Lys
                           820                   825                               830

Tyr   Gly   Thr   Ala   Gly   Tyr   Gly   Val   Glu   Ala   Arg   Gly   Pro   Thr   Pro   Glu
                     835                         840                               845

Glu   Ala   Gln   Arg   Glu   Lys   Asp   Thr   Arg   Ile   Ser   Lys   Lys   Met   Glu   Thr
               850                         855                         860

Met   Gly   Ile   Tyr   Phe   Ala   Thr   Pro   Glu   Trp   Val   Ala   Leu   Asn   Gly   His
         865                           870                   875                               880

Arg   Gly   Pro   Ser   Pro   Gly   Gln   Leu   Lys   Tyr   Trp   Gln   Asn   Thr   Arg   Glu
                                 885                         890                               895

Ile   Pro   Asp   Pro   Asn   Glu   Asp   Tyr   Leu   Asp   Tyr   Val   His   Ala   Glu   Lys
                           900                         905                               910

Ser   Arg   Leu   Ala   Ser   Glu   Glu   Gln   Ile   Leu   Arg   Ala   Ala   Thr   Ser   Ile
                     915                         920                               925

Tyr   Gly   Ala   Pro   Gly   Gln   Ala   Glu   Pro   Pro   Gln   Ala   Phe   Ile   Asp   Glu
               930                         935                               940

Val   Ala   Lys   Val   Tyr   Glu   Ile   Asn   His   Gly   Arg   Gly   Pro   Asn   Gln   Glu
         945                           950                         955                               960

Gln   Met   Lys   Asp   Leu   Leu   Leu   Thr   Ala   Met   Glu   Met   Lys   His   Arg   Asn
                                 965                         970                               975

Pro   Arg   Arg   Ala   Pro   Pro   Lys   Pro   Lys   Pro   Arg   Pro   Asn   Ala   Pro   Thr
                           980                         985                               990

Gln   Arg   Pro   Pro   Gly   Arg   Leu   Gly   Arg   Trp   Ile   Arg   Thr   Val   Ser   Asp
                     995                         1000                              1005

Glu   Asp   Leu   Glu
                     1010
```

( 2 ) INFORMATION FOR SEQ ID NO:2:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: DS326

( x i ) SEQUENCE DESCRIPTION: SEQ ID NO:2:

```
         Met   Thr   Asn   Leu   Gln   Asp   Gln   Thr   Gln   Gln   Ile   Val   Pro   Phe   Ile   Arg
         1                       5                         10                              15

Ser   Leu   Leu   Met   Pro   Thr   Thr   Gly   Pro   Ala   Ser   Ile   Pro   Asp   Asp   Thr
                           20                         25                              30

Leu   Glu   Lys   His   Thr   Leu   Arg   Ser   Glu   Thr   Ser   Thr   Tyr   Asn   Leu   Thr
                     35                         40                               45

Val   Gly   Asp   Thr   Gly   Ser   Gly   Leu   Ile   Val   Phe   Phe   Pro   Gly   Phe   Pro
               50                         55                               60

Gly   Ser   Ile   Val   Gly   Ala   His   Tyr   Thr   Leu   Gln   Ser   Asn   Gly   Asn   Tyr
         65                           70                         75                               80

Lys   Phe   Asp   Gln   Met   Leu   Leu   Thr   Ala   Gln   Asn   Leu   Pro   Ala   Ser   Tyr
                                 85                         90                               95

Asn   Tyr   Cys   Arg   Leu   Val   Ser   Arg   Ser   Leu   Thr   Val   Arg   Ser   Ser   Thr
                           100                         105                              110

Leu   Pro   Gly   Gly   Val   Tyr   Ala   Leu   Asn   Gly   Thr   Ile   Asn   Ala   Val   Thr
                     115                         120                              125
```

-continued

|     |     |     |     |     |     |     |     |     |     |     |     |     |     |     |     |
|-----|-----|-----|-----|-----|-----|-----|-----|-----|-----|-----|-----|-----|-----|-----|-----|
| Phe | Gln | Gly | Ser | Leu | Ser | Glu | Leu | Thr | Asp | Val | Ser | Tyr | Asn | Gly | Leu |
|     | 130 |     |     |     |     | 135 |     |     |     |     | 140 |     |     |     |     |
| Met | Ser | Ala | Thr | Ala | Asn | Ile | Asn | Asp | Lys | Ile | Gly | Asn | Val | Leu | Val |
| 145 |     |     |     |     | 150 |     |     |     |     | 155 |     |     |     |     | 160 |
| Gly | Glu | Gly | Val | Thr | Val | Leu | Ser | Leu | Pro | Thr | Ser | Tyr | Asp | Leu | Gly |
|     |     |     |     | 165 |     |     |     |     | 170 |     |     |     |     | 175 |     |
| Tyr | Val | Arg | Leu | Gly | Asp | Pro | Ile | Pro | Ala | Ile | Gly | Leu | Asp | Pro | Lys |
|     |     |     | 180 |     |     |     |     | 185 |     |     |     |     |     | 190 |     |
| Met | Val | Ala | Thr | Cys | Asp | Ser | Ser | Asp | Arg | Pro | Arg | Val | Tyr | Thr | Ile |
|     |     |     | 195 |     |     |     |     | 200 |     |     |     | 205 |     |     |     |
| Thr | Ala | Ala | Asp | Asp | Tyr | Gln | Phe | Ser | Ser | Gln | Tyr | Gln | Ser | Gly | Gly |
|     | 210 |     |     |     |     | 215 |     |     |     |     | 220 |     |     |     |     |
| Val | Thr | Ile | Thr | Leu | Phe | Ser | Ala | Asn | Ile | Asp | Ala | Ile | Thr | Ser | Leu |
| 225 |     |     |     |     | 230 |     |     |     |     | 235 |     |     |     |     | 240 |
| Ser | Val | Gly | Gly | Glu | Leu | Val | Phe | Lys | Thr | Ser | Val | Gln | Ser | Leu | Val |
|     |     |     |     | 245 |     |     |     |     | 250 |     |     |     |     | 255 |     |
| Leu | Gly | Ala | Thr | Ile | Tyr | Leu | Ile | Gly | Phe | Asp | Gly | Thr | Ala | Val | Ile |
|     |     |     |     | 260 |     |     |     |     | 265 |     |     |     | 270 |     |     |
| Thr | Arg | Ala | Val | Ala | Ala | Asn | Asn | Gly | Leu | Thr | Ala | Gly | Thr | Asp | Asn |
|     |     | 275 |     |     |     |     | 280 |     |     |     |     | 285 |     |     |     |
| Leu | Met | Pro | Phe | Asn | Leu | Val | Ile | Pro | Thr | Asn | Glu | Ile | Thr | Gln | Pro |
|     | 290 |     |     |     |     | 295 |     |     |     |     | 300 |     |     |     |     |
| Ile | Thr | Ser | Ile | Lys | Leu | Lys | Ile | Val | Thr | Ser | Lys | Ser | Gly | Gly | Leu |
| 305 |     |     |     |     | 310 |     |     |     |     | 315 |     |     |     |     | 320 |
| Glu | Gly | Asp | Gln | Met | Ser | Trp | Ser | Ala | Ser | Gly | Ser | Leu | Ala | Val | Thr |
|     |     |     |     | 325 |     |     |     | 330 |     |     |     |     |     | 335 |     |
| Ile | His | Gly | Gly | Asn | Tyr | Pro | Gly | Ala | Leu | Arg | Pro | Val | Thr | Leu | Val |
|     |     |     | 340 |     |     |     |     | 345 |     |     |     |     | 350 |     |     |
| Ala | Tyr | Glu | Arg | Val | Ala | Thr | Gly | Ser | Val | Val | Thr | Val | Ala | Gly | Val |
|     |     | 355 |     |     |     |     | 360 |     |     |     |     | 365 |     |     |     |
| Ser | Asn | Phe | Glu | Leu | Ile | Pro | Asn | Pro | Glu | Leu | Ala | Lys | Asn | Leu | Val |
|     | 370 |     |     |     |     | 375 |     |     |     |     | 380 |     |     |     |     |
| Thr | Glu | Tyr | Gly | Arg | Phe | Asp | Pro | Gly | Ala | Met | Asn | Tyr | Thr | Lys | Leu |
| 385 |     |     |     |     | 390 |     |     |     |     | 395 |     |     |     |     | 400 |
| Ile | Leu | Ser | Glu | Arg | Asp | Arg | Leu | Gly | Ile | Lys | Thr | Val | Trp | Pro | Thr |
|     |     |     |     | 405 |     |     |     |     | 410 |     |     |     |     | 415 |     |
| Arg | Glu | Tyr | Thr | Asp | Phe | Arg | Glu | Tyr | Phe | Met | Glu | Val | Ala | Asp | Leu |
|     |     |     | 420 |     |     |     |     | 425 |     |     |     |     |     | 430 |     |
| Asn | Ser | Pro | Leu | Lys | Ile | Ala | Gly | Ala | Phe | Gly | Phe | Lys | Asp | Ile | Ile |
|     |     | 435 |     |     |     |     | 440 |     |     |     |     | 445 |     |     |     |
| Arg | Ala | Ile | Arg | Arg | Ile | Ala | Val | Pro | Val | Val | Ser | Thr | Leu | Phe | Pro |
|     | 450 |     |     |     |     | 455 |     |     |     |     | 460 |     |     |     |     |
| Pro | Ala | Ala | Pro | Leu | Ala | His | Ala | Ile | Gly | Glu | Gly | Val | Asp | Tyr | Leu |
| 465 |     |     |     |     | 470 |     |     |     |     | 475 |     |     |     |     | 480 |
| Leu | Gly | Asp | Glu | Ala | Gln | Ala | Ala | Ser | Gly | Thr | Ala | Arg | Ala | Ala | Ser |
|     |     |     |     | 485 |     |     |     |     | 490 |     |     |     |     | 495 |     |
| Gly | Lys | Ala | Arg | Ala | Ala | Ser | Gly | Arg | Ile | Arg | Gln | Leu | Thr | Leu | Ala |
|     |     |     | 500 |     |     |     |     | 505 |     |     |     |     | 510 |     |     |
| Ala | Asp | Lys | Gly | Tyr | Glu | Val | Val | Ala | Asn | Leu | Phe | Gln | Val | Pro | Gln |
|     |     | 515 |     |     |     |     | 520 |     |     |     |     | 525 |     |     |     |
| Asn | Pro | Val | Val | Asp | Gly | Ile | Leu | Ala | Ser | Pro | Gly | Ile | Leu | Arg | Gly |
|     | 530 |     |     |     |     | 535 |     |     |     |     | 540 |     |     |     |     |
| Ala | His | Asn | Leu | Asp | Cys | Val | Leu | Arg | Glu | Gly | Ala | Thr | Leu | Phe | Pro |
| 545 |     |     |     |     | 550 |     |     |     |     | 555 |     |     |     |     | 560 |

-continued

| | | | | | | | | | | | | | | |
|---|---|---|---|---|---|---|---|---|---|---|---|---|---|---|
| Val | Val | Ile | Thr | Thr 565 | Val | Glu | Asp | Ala | Met 570 | Thr | Pro | Lys | Ala | Leu 575 | Asn |
| Ser | Lys | Met | Phe 580 | Ala | Val | Ile | Glu | Gly 585 | Ala | Arg | Glu | Asp | Leu 590 | Gln | Pro |
| Pro | Ser | Gln 595 | Arg | Gly | Ser | Phe | Ile 600 | Arg | Thr | Leu | Ser | Gly 605 | His | Arg | Val |
| Tyr | Gly 610 | Tyr | Ala | Pro | Asp | Gly 615 | Val | Leu | Pro | Leu | Glu 620 | Thr | Gly | Arg | Asp |
| Tyr 625 | Thr | Val | Val | Pro | Ile 630 | Asp | Asp | Val | Trp | Asp 635 | Ser | Ile | Met | Leu 640 |
| Ser | Lys | Asp | Pro | Ile 645 | Pro | Pro | Ile | Val | Gly 650 | Asn | Ser | Gly | Asn 655 | Leu | Ala |
| Ile | Ala | Tyr | Met 660 | Asp | Val | Phe | Arg | Pro 665 | Lys | Val | Pro | Ile 670 | His | Val | Ala |
| Met | Thr | Gly 675 | Ala | Leu | Asn | Ala | Tyr 680 | Gly | Glu | Ile | Glu | Lys 685 | Ile | Ser | Phe |
| Arg | Ser 690 | Thr | Lys | Leu | Ala | Thr 695 | Ala | His | Arg | Leu | Gly 700 | Leu | Lys | Leu | Ala |
| Gly 705 | Pro | Gly | Ala | Phe | Asp 710 | Val | Asn | Thr | Gly | Pro 715 | Asn | Trp | Ala | Thr | Phe 720 |
| Ile | Lys | Arg | Phe | Pro 725 | His | Asn | Pro | Arg | Asp 730 | Trp | Asp | Arg | Leu | Pro 735 | Tyr |
| Leu | Asn | Leu | Pro 740 | Tyr | Leu | Pro | Pro | Asn 745 | Ala | Gly | Arg | Gln | Tyr 750 | His | Leu |
| Ala | Met | Ala 755 | Ala | Ser | Glu | Phe | Lys 760 | Glu | Thr | Pro | Glu | Leu 765 | Glu | Ser | Ala |
| Val | Arg 770 | Ala | Met | Glu | Ala | Ala 775 | Ala | Asn | Val | Asp | Pro 780 | Leu | Phe | Gln | Ser |
| Ala 785 | Leu | Ser | Val | Phe | Met 790 | Trp | Leu | Glu | Glu | Asn 795 | Gly | Ile | Val | Ala | Asp 800 |
| Met | Ala | Asn | Phe | Ala 805 | Leu | Ser | Asp | Pro | Asn 810 | Ala | His | Arg | Met | Arg 815 | Asn |
| Phe | Leu | Ala | Asn 820 | Ala | Pro | Gln | Ala | Gly 825 | Ser | Lys | Ser | Gln | Arg 830 | Ala | Lys |
| Tyr | Gly | Thr 835 | Ala | Gly | Tyr | Gly | Val 840 | Glu | Ala | Arg | Gly | Pro 845 | Thr | Pro | Glu |
| Glu | Ala 850 | Gln | Arg | Glu | Lys | Asp 855 | Thr | Arg | Ile | Ser | Lys 860 | Lys | Met | Glu | Thr |
| Met 865 | Gly | Ile | Tyr | Phe | Ala 870 | Thr | Pro | Glu | Trp | Val 875 | Ala | Leu | Asn | Gly | His 880 |
| Arg | Gly | Pro | Ser | Pro 885 | Gly | Gln | Leu | Lys | Tyr 890 | Trp | Gln | Asn | Thr | Arg 895 | Glu |
| Ile | Pro | Asp | Pro 900 | Asn | Glu | Asp | Tyr | Leu 905 | Asp | Tyr | Val | His | Ala 910 | Glu | Lys |
| Ser | Arg | Leu 915 | Ala | Ser | Glu | Glu | Gln 920 | Ile | Leu | Lys | Ala | Ala 925 | Thr | Ser | Ile |
| Tyr | Gly 930 | Ala | Pro | Gly | Gln | Ala 935 | Glu | Pro | Pro | Gln | Ala 940 | Phe | Ile | Asp | Glu |
| Val 945 | Ala | Lys | Val | Tyr | Glu 950 | Ile | Asn | His | Gly | Arg 955 | Gly | Pro | Asn | Gln | Glu 960 |
| Gln | Met | Lys | Asp | Leu 965 | Leu | Leu | Thr | Ala | Met 970 | Glu | Met | Lys | His | Arg 975 | Asn |
| Pro | Arg | Arg | Ala | Pro | Pro | Lys | Pro | Lys | Pro | Lys | Pro | Asn | Ala | Pro | Thr |

|   |   |   |   |   |   |   | 980 |   |   |   |   |   | 985 |   |   |   |   |   | 990 |   |   |   |
|---|---|---|---|---|---|---|---|---|---|---|---|---|---|---|---|---|---|---|---|---|---|---|

Gln Arg Pro Pro Gly Arg Leu Gly Arg Trp Ile Arg Thr Val Ser Asp
              995                   1000                  1005

Glu Asp Leu Glu
         1010

( 2 ) INFORMATION FOR SEQ ID NO:3:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: E/DEL ( x i ) SEQUENCE DESCRIPTION: SEQ ID NO:3:

Met Thr Asn Leu Gln Asp Gln Thr Gln Gln Ile Val Pro Phe Ile Arg
 1               5                   10                  15

Ser Leu Leu Met Pro Thr Thr Gly Pro Ala Ser Ile Pro Asp Asp Thr
             20                  25                  30

Leu Glu Lys His Thr Leu Arg Ser Glu Thr Ser Thr Tyr Asn Leu Thr
         35                  40                  45

Val Gly Asp Thr Gly Ser Gly Leu Ile Val Phe Phe Pro Gly Phe Pro
     50                  55                  60

Gly Ser Ile Val Gly Ala His Tyr Thr Leu Gln Gly Asn Gly Asn Tyr
 65                  70                  75                  80

Lys Phe Asp Gln Met Leu Leu Thr Ala Gln Asn Leu Pro Ala Ser Tyr
                 85                  90                  95

Asn Tyr Cys Arg Leu Val Ser Arg Ser Leu Thr Val Arg Ser Ser Thr
             100                 105                 110

Leu Pro Gly Gly Val Tyr Ala Leu Asn Gly Thr Ile Asn Ala Val Thr
         115                 120                 125

Phe Gln Gly Ser Leu Ser Glu Leu Thr Asp Val Ser Tyr Asn Gly Leu
     130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                 165                 170                 175

Tyr Val Arg Leu Gly Asp Pro Ile Pro Ala Ile Gly Leu Asp Pro Lys
             180                 185                 190

Met Val Ala Thr Cys Asp Ser Ser Asp Arg Pro Arg Val Tyr Thr Ile
         195                 200                 205

Thr Ala Ala Asp Asp Tyr Gln Phe Ser Ser Gln Tyr Gln Pro Gly Gly
     210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Gln Thr Ser Val His Gly Leu Val
                 245                 250                 255

Leu Gly Ala Thr Ile Tyr Leu Ile Gly Phe Asp Gly Thr Thr Val Ile
             260                 265                 270

Thr Arg Ala Val Ala Ala Asn Asn Gly Leu Thr Thr Gly Thr Asp Asn
         275                 280                 285

Leu Met Pro Phe Asn Leu Val Ile Pro Thr Asn Glu Ile Thr Gln Pro

```
              290                      295                      300
       Ile Thr Ser Ile Lys Leu Glu Ile Val Thr Ser Lys Ser Gly Gly Gln
       305                 310                 315                 320
       Ala Gly Asp Gln Met Ser Trp Ser Ala Arg Gly Ser Leu Ala Val Thr
                       325                 330                 335
       Ile His Gly Gly Asn Tyr Pro Gly Ala Leu Arg Pro Val Thr Leu Val
                   340                 345                 350
       Ala Tyr Glu Arg Val Ala Thr Gly Ser Val Val Thr Val Ala Gly Val
                   355                 360                 365
       Ser Asn Phe Glu Leu Ile Pro Asn Pro Glu Leu Ala Lys Asn Leu Val
           370                 375                 380
       Thr Glu Tyr Gly Arg Phe Asp Pro Gly Ala Met Asn Tyr Thr Lys Leu
       385                 390                 395                 400
       Ile Leu Ser Glu Arg Asp Arg Leu Gly Ile Lys Thr Val Trp Pro Thr
                       405                 410                 415
       Arg Glu Tyr Thr Asp Phe Arg Glu Tyr Phe Met Glu Val Ala Asp Leu
                       420                 425                 430
       Asn Ser Pro Leu Lys Ile Ala Gly Ala Phe Gly Phe Lys Asp Ile Ile
                   435                 440                 445
       Arg Ala Ile Arg Arg Ile Ala Val Pro Val Val Ser Thr Leu Phe Pro
           450                 455                 460
       Pro Ala Ala Pro Leu Ala His Ala Ile Gly Glu Gly Val Asp Tyr Leu
       465                 470                 475                 480
       Leu Gly Asp Glu Ala Gln Ala Ala Ser Gly Thr Ala Arg Ala Ala Ser
                       485                 490                 495
       Gly Lys Ala Arg Ala Ala Ser Gly Arg Ile Arg Gln Leu Thr Leu Ala
                   500                 505                 510
       Ala Asp Lys Gly Tyr Glu Val Val Ala Asn Leu Phe Gln Val Pro Gln
                   515                 520                 525
       Asn Pro Val Val Asp Gly Ile Leu Ala Ser Pro Gly Val Leu Arg Gly
           530                 535                 540
       Ala His Asn Leu Asp Cys Val Leu Arg Glu Gly Ala Thr Leu Phe Pro
       545                 550                 555                 560
       Val Val Ile Thr Thr Val Glu Asp Ala Met Thr Pro Lys Ala Leu Asn
                       565                 570                 575
       Ser Lys Met Phe Ala Val Ile Glu Gly Val Arg Glu Asp Leu Gln Pro
                       580                 585                 590
       Pro Ser Gln Arg Gly Ser Phe Ile Arg Thr Leu Ser Gly His Arg Val
                   595                 600                 605
       Tyr Gly Tyr Ala Pro Asp Gly Val Leu Pro Leu Glu Thr Gly Arg Asp
           610                 615                 620
       Tyr Thr Val Val Pro Ile Asp Asp Val Trp Asp Asp Ser Ile Met Leu
       625                 630                 635                 640
       Ser Lys Asp Pro Ile Pro Pro Ile Val Gly Asn Ser Gly Asn Leu Ala
                       645                 650                 655
       Ile Ala Tyr Met Asp Val Phe Arg Pro Lys Val Pro Ile His Val Ala
                       660                 665                 670
       Met Thr Gly Ala Leu Asn Ala Cys Gly Glu Ile Glu Lys Val Ser Phe
                   675                 680                 685
       Arg Ser Thr Lys Leu Ala Thr Ala His Arg Leu Gly Leu Arg Leu Ala
           690                 695                 700
       Gly Pro Gly Ala Phe Asp Val Asn Thr Gly Pro Asn Trp Ala Thr Phe
       705                 710                 715                 720
```

-continued

```
Ile Lys Arg Phe Pro His Asn Pro Arg Asp Trp Asp Arg Leu Pro Tyr
                725                 730                 735
Leu Asn Leu Pro Tyr Leu Pro Pro Asn Ala Gly Arg Gln Tyr His Leu
            740                 745                 750
Ala Met Ala Ala Ser Glu Phe Lys Glu Thr Pro Glu Leu Glu Ser Ala
        755                 760                 765
Val Arg Ala Met Glu Ala Ala Asn Val Asp Pro Leu Phe Gln Ser
    770                 775                 780
Ala Leu Ser Val Phe Met Trp Leu Glu Glu Asn Gly Ile Val Thr Asp
785                 790                 795                 800
Met Ala Asn Phe Ala Leu Ser Asp Pro Asn Ala His Arg Met Arg Asn
                805                 810                 815
Phe Leu Ala Asn Ala Pro Gln Ala Gly Ser Lys Ser Gln Arg Ala Lys
            820                 825                 830
Tyr Gly Thr Ala Gly Tyr Gly Val Glu Ala Arg Gly Pro Thr Pro Glu
        835                 840                 845
Glu Ala Gln Arg Glu Lys Asp Thr Arg Ile Ser Lys Lys Met Glu Thr
    850                 855                 860
Met Gly Ile Tyr Phe Ala Thr Pro Glu Trp Val Ala Leu Asn Gly His
865                 870                 875                 880
Arg Gly Pro Ser Pro Gly Gln Leu Lys Tyr Trp Gln Asn Thr Arg Glu
                885                 890                 895
Ile Pro Asp Pro Asn Glu Asp Tyr Leu Asp Tyr Val His Ala Glu Lys
            900                 905                 910
Ser Arg Leu Ala Ser Glu Glu Gln Ile Leu Arg Ala Ala Thr Ser Ile
        915                 920                 925
Tyr Gly Ala Pro Gly Gln Ala Glu Pro Pro Gln Ala Phe Ile Asp Glu
    930                 935                 940
Val Ala Lys Val Tyr Glu Ile Asn His Gly Arg Gly Pro Asn Gln Glu
945                 950                 955                 960
Gln Met Lys Asp Leu Leu Leu Thr Ala Met Glu Met Lys His Arg Asn
                965                 970                 975
Pro Arg Arg Ala Leu Pro Lys Pro Lys Pro Lys Pro Asn Ala Pro Thr
            980                 985                 990
Gln Arg Pro Pro Gly Arg Leu Gly Arg Trp Ile Arg Thr Val Ser Asp
        995                 1000                1005
Glu Asp Leu Glu
    1010
```

( 2 ) INFORMATION FOR SEQ ID NO:4:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: D78

( x i ) SEQUENCE DESCRIPTION: SEQ ID NO:4:

```
Met Thr Asn Leu Gln Asp Gln Thr His Gln Ile Val Pro Phe Ile Arg
1               5                   10                  15

Ser Leu Leu Met Pro Thr Thr Gly Pro Ala Ser Ile Pro Asp Asp Thr
            20                  25                  30
```

| Leu | Glu | Lys<br>35 | His | Thr | Leu | Arg | Ser<br>40 | Glu | Thr | Ser | Thr | Tyr<br>45 | Asn | Leu | Thr |
|---|---|---|---|---|---|---|---|---|---|---|---|---|---|---|---|
| Val | Gly<br>50 | Asp | Thr | Gly | Ser<br>55 | Gly | Leu | Ile | Val | Phe<br>60 | Phe | Pro | Gly | Phe | Pro |
| Gly<br>65 | Ser | Ile | Val | Gly<br>70 | Ala | His | Tyr | Thr | Leu<br>75 | Gln | Ser | Ser | Gly | Asn | Tyr<br>80 |
| Lys | Phe | Asp | Gln | Met<br>85 | Leu | Leu | Thr | Ala | Gln<br>90 | Asn | Leu | Pro | Ala | Ser<br>95 | Tyr |
| Asn | Tyr | Cys | Arg<br>100 | Leu | Val | Ser | Arg | Ser<br>105 | Leu | Thr | Val | Arg | Ser<br>110 | Ser | Thr |
| Leu | Pro | Gly<br>115 | Gly | Val | Tyr | Ala | Leu<br>120 | Asn | Gly | Thr | Ile | Asn<br>125 | Ala | Val | Thr |
| Phe | Gln<br>130 | Gly | Ser | Leu | Ser | Glu<br>135 | Leu | Thr | Asp | Val | Ser<br>140 | Tyr | Asn | Gly | Leu |
| Met<br>145 | Ser | Ala | Thr | Ala | Asn<br>150 | Ile | Asn | Asp | Lys | Ile<br>155 | Gly | Asn | Val | Leu | Val<br>160 |
| Gly | Glu | Gly | Val | Thr<br>165 | Val | Leu | Ser | Leu | Pro<br>170 | Thr | Ser | Tyr | Asp | Leu<br>175 | Gly |
| Tyr | Val | Arg | Leu<br>180 | Gly | Asp | Pro | Ile | Pro<br>185 | Ala | Ile | Gly | Leu | Asp<br>190 | Pro | Lys |
| Met | Val | Ala<br>195 | Thr | Cys | Asp | Ser | Ser<br>200 | Asp | Arg | Pro | Arg | Val<br>205 | Tyr | Thr | Ile |
| Thr | Ala<br>210 | Ala | Asp | Asn | Tyr | Gln<br>215 | Phe | Ser | Ser | Gln | Tyr<br>220 | Gln | Thr | Gly | Gly |
| Val<br>225 | Thr | Ile | Thr | Leu | Phe<br>230 | Ser | Ala | Asn | Ile | Asp<br>235 | Ala | Ile | Thr | Ser | Leu<br>240 |
| Ser | Val | Gly | Gly | Glu<br>245 | Leu | Val | Phe | Lys | Thr<br>250 | Ser | Val | Gln | Ser | Leu<br>255 | Val |
| Leu | Gly | Ala | Thr<br>260 | Ile | Tyr | Leu | Ile | Gly<br>265 | Phe | Asp | Gly | Thr | Ala<br>270 | Val | Ile |
| Thr | Arg | Ala<br>275 | Val | Ala | Ala | Asn | Asn<br>280 | Gly | Leu | Thr | Ala | Gly<br>285 | Ile | Asp | Asn |
| Leu | Met<br>290 | Pro | Phe | Asn | Leu | Val<br>295 | Ile | Pro | Thr | Asn | Glu<br>300 | Ile | Thr | Gln | Pro |
| Ile<br>305 | Thr | Ser | Ile | Ile | Leu<br>310 | Glu | Ile | Val | Thr | Ser<br>315 | Lys | Ser | Asp | Gly | Gln<br>320 |
| Ala | Gly | Glu | Gln | Met<br>325 | Ser | Trp | Ser | Ala | Ser<br>330 | Gly | Ser | Leu | Ala | Val<br>335 | Thr |
| Ile | His | Gly | Gly<br>340 | Asn | Tyr | Pro | Gly | Ala<br>345 | Leu | Arg | Pro | Val | Thr<br>350 | Leu | Val |
| Ala | Tyr | Glu<br>355 | Arg | Val | Ala | Thr | Gly<br>360 | Ser | Val | Val | Thr | Val<br>365 | Ala | Gly | Val |
| Ser | Asn<br>370 | Phe | Glu | Leu | Ile | Pro<br>375 | Asn | Pro | Glu | Leu | Ala<br>380 | Lys | Asn | Leu | Val |
| Thr<br>385 | Glu | Tyr | Gly | Arg | Phe<br>390 | Asp | Pro | Gly | Ala | Met<br>395 | Asn | Tyr | Thr | Lys | Leu<br>400 |
| Ile | Leu | Ser | Glu | Arg<br>405 | Asp | His | Leu | Gly | Ile<br>410 | Lys | Thr | Val | Trp | Pro<br>415 | Thr |
| Arg | Glu | Tyr | Thr<br>420 | Asp | Phe | Arg | Glu | Tyr<br>425 | Phe | Met | Glu | Val | Ala<br>430 | Asp | Leu |
| Asn | Ser | Pro<br>435 | Leu | Lys | Ile | Ala | Gly<br>440 | Ala | Phe | Gly | Phe | Lys<br>445 | Asp | Ile | Ile |
| Arg | Ala<br>450 | Ile | Arg | Arg | Ile | Ala<br>455 | Val | Pro | Val | Val | Ser<br>460 | Thr | Leu | Phe | Pro |

```
Pro  Ala  Ala  Pro  Leu  Ala  His  Ala  Ile  Gly  Glu  Gly  Val  Asp  Tyr  Leu
465                 470                 475                 480

Leu  Gly  Asp  Glu  Ala  Gln  Ala  Ala  Ser  Gly  Thr  Ala  Arg  Ala  Ala  Ser
                    485                 490                      495

Gly  Lys  Ala  Arg  Ala  Ala  Ser  Gly  Arg  Ile  Arg  Gln  Leu  Thr  Leu  Ala
               500                 505                      510

Ala  Asp  Lys  Gly  Tyr  Glu  Val  Val  Ala  Asn  Leu  Phe  Gln  Val  Pro  Gln
          515                 520                      525

Asn  Pro  Val  Val  Asp  Gly  Ile  Leu  Ala  Ser  Pro  Gly  Ile  Leu  Arg  Gly
     530                 535                      540

Ala  His  Asn  Leu  Asp  Cys  Val  Leu  Arg  Glu  Gly  Ala  Thr  Leu  Phe  Pro
545                 550                 555                           560

Val  Val  Ile  Thr  Thr  Val  Glu  Asp  Ala  Met  Thr  Pro  Lys  Ala  Leu  Asn
                    565                 570                      575

Ser  Lys  Met  Phe  Ala  Val  Ile  Glu  Gly  Val  Arg  Glu  Asp  Leu  Gln  Pro
               580                 585                      590

Pro  Ser  Gln  Arg  Gly  Ser  Phe  Ile  Arg  Thr  Leu  Ser  Gly  His  Arg  Val
          595                 600                      605

Tyr  Gly  Tyr  Ala  Pro  Asp  Gly  Val  Leu  Pro  Leu  Glu  Thr  Gly  Arg  Asp
610                 615                      620

Tyr  Thr  Val  Val  Pro  Ile  Asp  Asp  Val  Trp  Asp  Asp  Ser  Ile  Met  Leu
625                 630                 635                           640

Ser  Lys  Asp  Pro  Ile  Pro  Pro  Ile  Val  Gly  Asn  Ser  Gly  Asn  Leu  Ala
               645                 650                           655

Ile  Ala  Tyr  Met  Asp  Val  Phe  Arg  Pro  Lys  Val  Pro  Ile  His  Val  Ala
               660                 665                      670

Met  Thr  Gly  Ala  Leu  Asn  Ala  Cys  Gly  Glu  Ile  Glu  Lys  Ile  Ser  Phe
          675                 680                      685

Arg  Ser  Thr  Lys  Leu  Ala  Thr  Ala  His  Arg  Leu  Gly  Leu  Lys  Leu  Ala
     690                 695                      700

Gly  Pro  Gly  Ala  Phe  Asp  Val  Asn  Thr  Gly  Pro  Asn  Trp  Ala  Thr  Phe
705                 710                 715                           720

Ile  Lys  Arg  Phe  Pro  His  Asn  Pro  Arg  Asp  Trp  Asp  Arg  Leu  Pro  Tyr
               725                 730                      735

Leu  Asn  Leu  Pro  Tyr  Leu  Pro  Pro  Asn  Ala  Gly  Arg  Gln  Tyr  His  Leu
               740                 745                      750

Ala  Met  Ala  Ala  Ser  Glu  Phe  Lys  Glu  Thr  Pro  Glu  Leu  Glu  Ser  Ala
          755                 760                      765

Val  Arg  Ala  Met  Glu  Ala  Ala  Ala  Asn  Val  Asp  Pro  Leu  Phe  Gln  Ser
     770                 775                      780

Ala  Leu  Ser  Val  Phe  Met  Trp  Leu  Glu  Glu  Asn  Gly  Ile  Val  Thr  Asp
785                 790                 795                           800

Met  Ala  Asn  Phe  Ala  Leu  Ser  Asp  Pro  Asn  Ala  His  Arg  Met  Arg  Asn
               805                 810                      815

Phe  Leu  Ala  Asn  Ala  Pro  Gln  Ala  Gly  Ser  Lys  Ser  Gln  Arg  Ala  Lys
               820                 825                      830

Tyr  Gly  Thr  Ala  Gly  Tyr  Gly  Val  Glu  Ala  Arg  Gly  Pro  Thr  Pro  Glu
          835                 840                      845

Glu  Ala  Gln  Arg  Glu  Lys  Asp  Thr  Arg  Ile  Ser  Lys  Lys  Met  Glu  Thr
     850                 855                      860

Met  Gly  Ile  Tyr  Phe  Ala  Thr  Pro  Glu  Trp  Val  Ala  Leu  Asn  Gly  His
865                 870                 875                           880

Arg  Gly  Pro  Ser  Pro  Gly  Gln  Leu  Lys  Tyr  Trp  Gln  Asn  Thr  Arg  Glu
```

|  |  |  |  | 885 |  |  |  | 890 |  |  |  | 895 |  |  |
|---|---|---|---|---|---|---|---|---|---|---|---|---|---|---|
| Ile | Pro | Asp | Pro<br>900 | Asn | Glu | Asp | Tyr | Leu<br>905 | Asp | Tyr | Val | His | Ala<br>910 | Glu | Lys |
| Ser | Arg | Leu<br>915 | Ala | Ser | Glu | Glu | Gln<br>920 | Ile | Leu | Arg | Ala | Ala<br>925 | Thr | Ser | Ile |
| Tyr | Gly<br>930 | Ala | Pro | Gly | Gln | Ala<br>935 | Glu | Pro | Pro | Gln | Ala<br>940 | Phe | Ile | Asp | Glu |
| Val<br>945 | Ala | Lys | Val | Tyr | Glu<br>950 | Ile | Asn | His | Gly | Arg<br>955 | Gly | Pro | Asn | Gln | Gly<br>960 |
| Gln | Met | Lys | Asp | Leu<br>965 | Leu | Leu | Thr | Ala | Met<br>970 | Glu | Met | Lys | His | Arg<br>975 | Asn |
| Pro | Arg | Arg | Ala<br>980 | Pro | Pro | Lys | Pro | Lys<br>985 | Pro | Lys | Pro | Asn | Ala<br>990 | Pro | Thr |
| Gln | Arg | Pro<br>995 | Pro | Gly | Arg | Leu | Gly<br>1000 | Arg | Trp | Ile | Arg | Thr<br>1005 | Val | Ser | Asp |
| Glu | Asp | Leu | Glu<br>1010 |  |  |  |  |  |  |  |  |  |  |  |  |

( 2 ) INFORMATION FOR SEQ ID NO:5:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: CU-1

( x i ) SEQUENCE DESCRIPTION: SEQ ID NO:5:

| Met<br>1 | Thr | Asn | Leu | Gln<br>5 | Asp | Gln | Thr | Gln | Gln<br>10 | Ile | Val | Pro | Phe | Ile<br>15 | Arg |
|---|---|---|---|---|---|---|---|---|---|---|---|---|---|---|---|
| Ser | Leu | Leu | Met<br>20 | Pro | Thr | Thr | Gly | Pro<br>25 | Ala | Ser | Ile | Pro | Asp<br>30 | Asp | Thr |
| Leu | Glu | Lys<br>35 | His | Thr | Leu | Arg | Ser<br>40 | Glu | Thr | Ser | Thr | Tyr<br>45 | Asn | Leu | Thr |
| Val | Gly<br>50 | Asp | Thr | Gly | Ser<br>55 | Gly | Leu | Ile | Val | Phe<br>60 | Phe | Pro | Gly | Phe | Pro |
| Gly<br>65 | Ser | Ile | Val | Gly<br>70 | Ala | His | Tyr | Thr | Leu<br>75 | Gln | Ser | Asn | Gly | Asn | Tyr<br>80 |
| Lys | Phe | Asp | Gln | Met<br>85 | Leu | Leu | Thr | Ala | Gln<br>90 | Asn | Leu | Pro | Ala | Ser<br>95 | Tyr |
| Asn | Tyr | Cys | Arg<br>100 | Leu | Val | Ser | Arg | Ser<br>105 | Leu | Thr | Val | Arg | Ser<br>110 | Ser | Thr |
| Leu | Pro | Gly<br>115 | Gly | Val | Tyr | Ala | Leu<br>120 | Asn | Gly | Thr | Ile | Asn<br>125 | Ala | Val | Thr |
| Phe | Gln<br>130 | Gly | Ser | Leu | Ser | Glu<br>135 | Leu | Thr | Asp | Val | Ser<br>140 | Tyr | Asn | Gly | Leu |
| Met<br>145 | Ser | Ala | Thr | Ala | Asn<br>150 | Ile | Asn | Asp | Lys | Ile<br>155 | Gly | Asn | Val | Leu | Val<br>160 |
| Gly | Glu | Gly | Val | Thr<br>165 | Val | Leu | Ser | Leu | Pro<br>170 | Thr | Ser | Tyr | Asp | Leu<br>175 | Gly |
| Tyr | Val | Arg | Leu<br>180 | Gly | Asp | Pro | Ile | Pro<br>185 | Ala | Ile | Gly | Leu | Asp<br>190 | Pro | Lys |
| Met | Val | Ala | Thr | Cys | Asp | Ser | Ser | Asp | Arg | Pro | Arg | Val | Tyr | Thr | Ile |

-continued

|  |  |  | 195 |  |  |  | 200 |  |  |  | 205 |  |  |
|---|---|---|---|---|---|---|---|---|---|---|---|---|---|
| Thr | Ala | Ala | Asp | Asp | Tyr | Gln | Phe | Ser | Ser | Gln | Tyr | Gln | Pro | Gly | Gly |
| 210 | | | | | 215 | | | | | 220 | | | | | |
| Val | Thr | Ile | Thr | Leu | Phe | Ser | Ala | Asn | Ile | Asp | Ala | Ile | Thr | Ser | Leu |
| 225 | | | | | 230 | | | | | 235 | | | | | 240 |
| Ser | Val | Gly | Gly | Glu | Leu | Val | Phe | Gln | Thr | Ser | Val | His | Gly | Leu | Val |
| | | | | 245 | | | | | 250 | | | | | 255 | |
| Leu | Gly | Ala | Thr | Ile | Tyr | Leu | Ile | Gly | Phe | Asp | Gly | Thr | Thr | Val | Ile |
| | | | 260 | | | | | 265 | | | | | 270 | | |
| Thr | Arg | Ala | Val | Ala | Ala | Asn | Asn | Gly | Leu | Thr | Thr | Gly | Thr | Asp | Asn |
| | 275 | | | | | 280 | | | | | 285 | | | | |
| Leu | Met | Pro | Phe | Asn | Leu | Val | Ile | Ser | Thr | Asn | Glu | Ile | Thr | Gln | Pro |
| | 290 | | | | | 295 | | | | | 300 | | | | |
| Ile | Thr | Ser | Ile | Lys | Leu | Glu | Ile | Val | Thr | Ser | Lys | Ser | Gly | Gly | Gln |
| 305 | | | | | 310 | | | | | 315 | | | | | 320 |
| Ala | Gly | Asp | Gln | Met | Ser | Trp | Ser | Ala | Lys | Gly | Ser | Leu | Ala | Val | Thr |
| | | | | 325 | | | | | 330 | | | | | 335 | |
| Ile | His | Gly | Gly | Asn | Tyr | Pro | Gly | Ala | Leu | Arg | Pro | Val | Thr | Leu | Val |
| | | | 340 | | | | | 345 | | | | | 350 | | |
| Ala | Tyr | Glu | Arg | Val | Ala | Thr | Gly | Ser | Val | Val | Thr | Val | Ala | Gly | Val |
| | | 355 | | | | | 360 | | | | | 365 | | | |
| Ser | Asn | Phe | Glu | Leu | Ile | Pro | Asn | Pro | Glu | Leu | Ala | Lys | Asn | Leu | Val |
| | 370 | | | | | 375 | | | | | 380 | | | | |
| Thr | Glu | Tyr | Gly | Arg | Phe | Asp | Pro | Gly | Ala | Met | Asn | Tyr | Thr | Lys | Leu |
| 385 | | | | | 390 | | | | | 395 | | | | | 400 |
| Ile | Leu | Ser | Glu | Arg | Asp | Arg | Leu | Gly | Ile | Lys | Thr | Val | Trp | Pro | Thr |
| | | | | 405 | | | | | 410 | | | | | 415 | |
| Arg | Glu | Tyr | Thr | Asp | Phe | Arg | Glu | Tyr | Phe | Met | Glu | Val | Ala | Asp | Leu |
| | | | 420 | | | | | 425 | | | | | 430 | | |
| Asn | Ser | Pro | Leu | Lys | Ile | Ala | Gly | Ala | Phe | Gly | Phe | Lys | Asp | Ile | Ile |
| | | 435 | | | | | 440 | | | | | 445 | | | |
| Arg | Ala | Ile | Arg | Arg | Ile | Ala | Val | Pro | Val | Val | Ser | Thr | Leu | Phe | Pro |
| | 450 | | | | | 455 | | | | | 460 | | | | |
| Pro | Ala | Ala | Pro | Leu | Ala | His | Ala | Ile | Gly | Glu | Gly | Val | Asp | Tyr | Leu |
| 465 | | | | | 470 | | | | | 475 | | | | | 480 |
| Leu | Gly | Asp | Glu | Ala | Gln | Ala | Ala | Ser | Gly | Thr | Ala | Arg | Ala | Ala | Ser |
| | | | | 485 | | | | | 490 | | | | | 495 | |
| Gly | Lys | Ala | Arg | Ala | Ala | Ser | Gly | Arg | Ile | Arg | Gln | Leu | Thr | Leu | Ala |
| | | | 500 | | | | | 505 | | | | | 510 | | |
| Ala | Asp | Lys | Gly | Tyr | Glu | Val | Val | Ala | Asn | Leu | Phe | Gln | Val | Pro | Gln |
| | | 515 | | | | | 520 | | | | | 525 | | | |
| Asn | Pro | Val | Val | Asp | Gly | Ile | Leu | Ala | Ser | Pro | Gly | Val | Leu | Arg | Gly |
| | 530 | | | | | 535 | | | | | 540 | | | | |
| Ala | His | Asn | Leu | Asp | Cys | Val | Leu | Arg | Glu | Gly | Ala | Thr | Leu | Phe | Pro |
| 545 | | | | | 550 | | | | | 555 | | | | | 560 |
| Val | Val | Ile | Thr | Thr | Val | Glu | Asp | Ala | Met | Thr | Pro | Lys | Ala | Leu | Asn |
| | | | | 565 | | | | | 570 | | | | | 575 | |
| Ser | Lys | Met | Phe | Ala | Val | Ile | Glu | Gly | Val | Arg | Glu | Asp | Leu | Gln | Pro |
| | | | 580 | | | | | 585 | | | | | 590 | | |
| Pro | Ser | Gln | Arg | Gly | Ser | Phe | Ile | Arg | Thr | Leu | Ser | Gly | His | Arg | Val |
| | | 595 | | | | | 600 | | | | | 605 | | | |
| Tyr | Gly | Tyr | Ala | Pro | Asp | Gly | Val | Leu | Pro | Leu | Glu | Thr | Gly | Arg | Asp |
| | 610 | | | | | 615 | | | | | 620 | | | | |

| | | | | | | | | | | | | | | |
|---|---|---|---|---|---|---|---|---|---|---|---|---|---|---|
| Tyr | Thr | Val | Val | Pro | Ile | Asp | Asp | Val | Trp | Asp | Asp | Ser | Ile | Met | Leu |
| 625 | | | | | 630 | | | | 635 | | | | | | 640 |
| Ser | Lys | Asp | Pro | Ile | Pro | Pro | Ile | Val | Gly | Asn | Ser | Gly | Asn | Leu | Ala |
| | | | | 645 | | | | | 650 | | | | | 655 | |
| Ile | Ala | Tyr | Met | Asp | Val | Phe | Arg | Pro | Lys | Val | Pro | Ile | His | Val | Ala |
| | | | 660 | | | | | 665 | | | | | 670 | | |
| Met | Thr | Gly | Ala | Leu | Asn | Ala | Cys | Gly | Glu | Ile | Glu | Lys | Val | Ser | Phe |
| | | 675 | | | | | 680 | | | | | 685 | | | |
| Arg | Ser | Thr | Lys | Leu | Ala | Thr | Ala | His | Arg | Leu | Gly | Leu | Lys | Leu | Ala |
| | 690 | | | | | 695 | | | | | 700 | | | | |
| Gly | Pro | Gly | Ala | Phe | Asp | Val | Asn | Thr | Gly | Pro | Asn | Trp | Ala | Thr | Phe |
| 705 | | | | | 710 | | | | 715 | | | | | | 720 |
| Ile | Lys | Arg | Phe | Pro | His | Asn | Pro | Arg | Asp | Trp | Asp | Arg | Leu | Pro | Tyr |
| | | | | 725 | | | | | 730 | | | | | 735 | |
| Leu | Asn | Leu | Pro | Tyr | Leu | Pro | Pro | Asn | Ala | Gly | Arg | Gln | Tyr | His | Leu |
| | | | 740 | | | | | 745 | | | | | 750 | | |
| Ala | Met | Ala | Ala | Ser | Glu | Phe | Lys | Glu | Thr | Pro | Glu | Leu | Glu | Ser | Ala |
| | | 755 | | | | | 760 | | | | | 765 | | | |
| Val | Arg | Ala | Met | Glu | Ala | Ala | Ala | Asn | Val | Asp | Pro | Leu | Phe | Gln | Ser |
| | 770 | | | | | 775 | | | | | 780 | | | | |
| Ala | Leu | Ser | Val | Phe | Met | Trp | Leu | Glu | Glu | Asn | Gly | Ile | Val | Thr | Asp |
| 785 | | | | | 790 | | | | 795 | | | | | | 800 |
| Met | Ala | Asn | Phe | Ala | Leu | Ser | Asp | Pro | Asn | Ala | His | Arg | Met | Arg | Asn |
| | | | | 805 | | | | | 810 | | | | | 815 | |
| Phe | Leu | Ala | Asn | Ala | Pro | Gln | Ala | Gly | Ser | Lys | Ser | Gln | Arg | Ala | Lys |
| | | | 820 | | | | | 825 | | | | | 830 | | |
| Tyr | Gly | Thr | Ala | Gly | Tyr | Gly | Val | Glu | Ala | Arg | Gly | Pro | Thr | Pro | Glu |
| | | 835 | | | | | 840 | | | | | 845 | | | |
| Glu | Ala | Gln | Arg | Glu | Lys | Asp | Thr | Arg | Ile | Ser | Lys | Lys | Met | Glu | Thr |
| | 850 | | | | | 855 | | | | | 860 | | | | |
| Met | Gly | Ile | Tyr | Phe | Ala | Thr | Pro | Glu | Trp | Val | Ala | Leu | Asn | Gly | His |
| 865 | | | | | 870 | | | | 875 | | | | | | 880 |
| Arg | Gly | Pro | Ser | Pro | Gly | Gln | Leu | Lys | Tyr | Trp | Gln | Asn | Thr | Arg | Glu |
| | | | | 885 | | | | | 890 | | | | | 895 | |
| Ile | Pro | Asp | Pro | Asn | Glu | Asp | Tyr | Leu | Asp | Tyr | Val | His | Ala | Glu | Lys |
| | | | 900 | | | | | 905 | | | | | 910 | | |
| Ser | Arg | Leu | Ala | Ser | Glu | Glu | Gln | Ile | Leu | Arg | Ala | Ala | Thr | Ser | Ile |
| | | 915 | | | | | 920 | | | | | 925 | | | |
| Tyr | Gly | Ala | Pro | Gly | Gln | Ala | Glu | Pro | Pro | Gln | Ala | Phe | Ile | Asp | Glu |
| | 930 | | | | | 935 | | | | | 940 | | | | |
| Val | Ala | Lys | Val | Tyr | Glu | Ile | Asn | His | Gly | Arg | Gly | Pro | Asn | Gln | Glu |
| 945 | | | | | 950 | | | | 955 | | | | | | 960 |
| Gln | Met | Lys | Asp | Leu | Leu | Leu | Thr | Ala | Met | Glu | Met | Lys | His | Arg | Asn |
| | | | | 965 | | | | | 970 | | | | | 975 | |
| Pro | Arg | Arg | Ala | Leu | Pro | Lys | Pro | Lys | Pro | Lys | Pro | Asn | Ala | Pro | Thr |
| | | | 980 | | | | | 985 | | | | | 990 | | |
| Gln | Arg | Pro | Pro | Gly | Arg | Leu | Gly | Arg | Trp | Ile | Arg | Thr | Val | Ser | Asp |
| | | 995 | | | | | 1000 | | | | | 1005 | | | |
| Glu | Asp | Leu | Glu | | | | | | | | | | | | |
| | | | 1010 | | | | | | | | | | | | |

( 2 ) INFORMATION FOR SEQ ID NO:6:

( i ) SEQUENCE CHARACTERISTICS:
    ( A ) LENGTH: 1012 amino acids ( B ) TYPE: amino acid
( C ) STRANDEDNESS:
( D ) TOPOLOGY: unknown ( i i ) MOLECULE TYPE: protein ( v i ) ORIGINAL SOURCE:
   ( A ) ORGANISM: Infectious bursal disease virus
   ( B ) STRAIN: PBG98

( x i ) SEQUENCE DESCRIPTION: SEQ ID NO:6:

```
Xaa Xaa Xaa Xaa Xaa Xaa Xaa Xaa Xaa Xaa Xaa Xaa Xaa Xaa Xaa
 1           5                  10                  15

Xaa Xaa Xaa Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Thr Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Leu Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365
```

| | | | | | | | | | | | | | | |
|---|---|---|---|---|---|---|---|---|---|---|---|---|---|---|
| Ser | Asn | Phe | Glu | Leu | Ile | Pro | Asn | Pro | Glu | Leu | Ala | Lys | Asn | Leu | Val |
| | 370 | | | | | 375 | | | | 380 | | | | |
| Thr | Glu | Tyr | Gly | Arg | Phe | Asp | Pro | Gly | Ala | Met | Asn | Tyr | Thr | Lys | Leu |
| 385 | | | | | 390 | | | | | 395 | | | | | 400 |
| Ile | Leu | Ser | Glu | Arg | Asp | Arg | Leu | Gly | Ile | Lys | Thr | Val | Trp | Pro | Thr |
| | | | | 405 | | | | | 410 | | | | | 415 | |
| Arg | Glu | Tyr | Thr | Asp | Phe | Arg | Glu | Tyr | Phe | Met | Glu | Val | Ala | Asp | Leu |
| | | | 420 | | | | | 425 | | | | | 430 | | |
| Asn | Ser | Pro | Leu | Lys | Ile | Ala | Gly | Ala | Phe | Gly | Phe | Lys | Asp | Ile | Ile |
| | | 435 | | | | | 440 | | | | | 445 | | | |
| Arg | Ala | Ile | Arg | Arg | Ile | Ala | Val | Pro | Val | Val | Ser | Thr | Leu | Phe | Pro |
| | 450 | | | | | 455 | | | | | 460 | | | | |
| Pro | Ala | Ala | Pro | Leu | Ala | His | Ala | Ile | Gly | Glu | Gly | Val | Asp | Tyr | Leu |
| 465 | | | | | 470 | | | | | 475 | | | | | 480 |
| Leu | Gly | Asp | Glu | Ala | Gln | Ala | Ala | Ser | Gly | Thr | Ala | Arg | Ala | Ala | Ser |
| | | | | 485 | | | | | 490 | | | | | | 495 |
| Gly | Lys | Ala | Arg | Ala | Ala | Ser | Gly | Arg | Ile | Arg | Gln | Leu | Thr | Leu | Ala |
| | | | 500 | | | | | 505 | | | | | 510 | | |
| Ala | Asp | Lys | Gly | Tyr | Glu | Val | Val | Ala | Asn | Leu | Phe | Gln | Val | Pro | Gln |
| | | 515 | | | | | 520 | | | | | 525 | | | |
| Asn | Pro | Val | Val | Asp | Gly | Ile | Leu | Ala | Ser | Pro | Gly | Val | Leu | Arg | Gly |
| | 530 | | | | | 535 | | | | | 540 | | | | |
| Ala | His | Asn | Leu | Asp | Cys | Val | Leu | Arg | Glu | Gly | Ala | Thr | Leu | Phe | Pro |
| 545 | | | | | 550 | | | | | 555 | | | | | 560 |
| Val | Val | Ile | Thr | Thr | Val | Glu | Asp | Ala | Met | Thr | Pro | Lys | Ala | Leu | Asn |
| | | | | 565 | | | | | 570 | | | | | 575 | |
| Ser | Lys | Met | Phe | Ala | Val | Ile | Glu | Gly | Val | Arg | Glu | Asp | Leu | Gln | Pro |
| | | | 580 | | | | | 585 | | | | | 590 | | |
| Pro | Ser | Gln | Arg | Gly | Ser | Phe | Ile | Arg | Thr | Leu | Ser | Gly | His | Arg | Val |
| | | 595 | | | | | 600 | | | | | 605 | | | |
| Tyr | Gly | Tyr | Ala | Pro | Asp | Gly | Val | Leu | Pro | Leu | Glu | Thr | Gly | Arg | Asp |
| | 610 | | | | | 615 | | | | | 620 | | | | |
| Tyr | Thr | Val | Val | Pro | Ile | Asp | Asp | Val | Trp | Asp | Asp | Ser | Ile | Met | Leu |
| 625 | | | | | 630 | | | | | 635 | | | | | 640 |
| Ser | Lys | Asp | Pro | Ile | Pro | Pro | Ile | Val | Gly | Asn | Ser | Gly | Asn | Leu | Ala |
| | | | | 645 | | | | | 650 | | | | | 655 | |
| Ile | Ala | Tyr | Met | Asp | Val | Phe | Arg | Pro | Lys | Val | Pro | Ile | His | Val | Ala |
| | | | 660 | | | | | 665 | | | | | 670 | | |
| Met | Thr | Gly | Ala | Leu | Asn | Ala | Cys | Gly | Glu | Ile | Glu | Lys | Val | Ser | Phe |
| | | 675 | | | | | 680 | | | | | 685 | | | |
| Arg | Ser | Thr | Lys | Leu | Ala | Thr | Ala | His | Arg | Leu | Gly | Leu | Lys | Leu | Ala |
| | 690 | | | | | 695 | | | | | 700 | | | | |
| Gly | Pro | Gly | Ala | Phe | Asp | Val | Asn | Thr | Gly | Pro | Asn | Trp | Ala | Thr | Phe |
| 705 | | | | | 710 | | | | | 715 | | | | | 720 |
| Ile | Lys | Arg | Phe | Pro | His | Asn | Pro | Arg | Asp | Trp | Asp | Arg | Leu | Pro | Tyr |
| | | | | 725 | | | | | 730 | | | | | 735 | |
| Leu | Asn | Leu | Pro | Tyr | Leu | Pro | Pro | Asn | Ala | Gly | Arg | Gln | Tyr | His | Leu |
| | | | 740 | | | | | 745 | | | | | 750 | | |
| Ala | Met | Ala | Ala | Ser | Glu | Phe | Lys | Glu | Thr | Pro | Glu | Leu | Glu | Ser | Ala |
| | | 755 | | | | | 760 | | | | | 765 | | | |
| Val | Arg | Ala | Met | Glu | Ala | Ala | Ala | Asn | Val | Asp | Pro | Leu | Phe | Gln | Ser |
| | 770 | | | | | 775 | | | | | 780 | | | | |
| Ala | Leu | Ser | Val | Phe | Met | Trp | Leu | Glu | Glu | Asn | Gly | Ile | Val | Thr | Asp |

-continued

```
                    785                     790                      795                     800
    Met  Ala  Asn  Phe  Ala  Leu  Ser  Asp  Pro  Asn  Ala  His  Arg  Met  Arg  Asn
                        805                      810                      815

Phe  Leu  Ala  Asn  Ala  Pro  Gln  Ala  Gly  Ser  Lys  Ser  Gln  Arg  Ala  Lys
                        820                      825                      830

Tyr  Gly  Thr  Ala  Gly  Tyr  Gly  Val  Glu  Ala  Arg  Gly  Pro  Thr  Pro  Glu
                        835                      840                      845

Glu  Ala  Gln  Arg  Glu  Lys  Asp  Thr  Arg  Ile  Ser  Lys  Lys  Met  Glu  Thr
                   850                      855                      860

Met  Gly  Ile  Tyr  Phe  Ala  Thr  Pro  Glu  Trp  Val  Ala  Leu  Asn  Gly  His
    865                      870                      875                      880

Arg  Gly  Pro  Ser  Pro  Gly  Gln  Leu  Lys  Tyr  Trp  Gln  Asn  Thr  Arg  Glu
                        885                      890                      895

Ile  Pro  Asp  Pro  Asn  Glu  Asp  Tyr  Leu  Asp  Tyr  Val  His  Ala  Glu  Lys
                        900                      905                      910

Ser  Arg  Leu  Ala  Ser  Glu  Glu  Gln  Ile  Leu  Arg  Ala  Ala  Thr  Ser  Ile
                   915                      920                      925

Tyr  Gly  Ala  Pro  Gly  Gln  Ala  Glu  Pro  Pro  Gln  Ala  Phe  Ile  Asp  Glu
         930                      935                      940

Val  Ala  Lys  Val  Tyr  Glu  Ile  Asn  His  Gly  Arg  Gly  Pro  Asn  Gln  Glu
    945                      950                      955                      960

Gln  Met  Lys  Asp  Leu  Leu  Leu  Thr  Ala  Met  Glu  Met  Lys  His  Arg  Asn
                        965                      970                      975

Pro  Arg  Arg  Ala  Leu  Pro  Lys  Pro  Lys  Pro  Lys  Pro  Asn  Ala  Pro  Thr
                        980                      985                      990

Gln  Arg  Pro  Pro  Gly  Arg  Leu  Gly  Arg  Trp  Ile  Arg  Thr  Val  Ser  Asp
                   995                      1000                     1005

Glu  Asp  Leu  Glu
                   1010
```

( 2 ) INFORMATION FOR SEQ ID NO:7:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: 52/70

( x i ) SEQUENCE DESCRIPTION: SEQ ID NO:7:

```
    Met  Thr  Asn  Leu  Gln  Asp  Gln  Thr  Gln  Gln  Ile  Val  Pro  Phe  Ile  Arg
    1                   5                        10                       15

Ser  Leu  Leu  Met  Pro  Thr  Thr  Gly  Pro  Ala  Ser  Ile  Pro  Asp  Asp  Thr
                        20                       25                       30

Leu  Glu  Lys  His  Thr  Leu  Arg  Ser  Glu  Thr  Ser  Thr  Tyr  Asn  Leu  Thr
                   35                       40                       45

Val  Gly  Asp  Thr  Gly  Ser  Gly  Leu  Ile  Val  Phe  Phe  Pro  Gly  Phe  Pro
         50                       55                       60

Gly  Ser  Ile  Val  Gly  Ala  His  Tyr  Thr  Leu  Gln  Ser  Asn  Gly  Asn  Tyr
    65                       70                       75                       80

Lys  Phe  Asp  Gln  Met  Leu  Leu  Thr  Ala  Gln  Asn  Leu  Pro  Ala  Ser  Tyr
                        85                       90                       95

Asn  Tyr  Cys  Arg  Leu  Val  Ser  Arg  Ser  Leu  Thr  Val  Arg  Ser  Ser  Thr
```

|  |  |  |  |  |  |  |  |  |  |  |  |  |  |  |
|---|---|---|---|---|---|---|---|---|---|---|---|---|---|---|
|  |  |  | 100 |  |  |  | 105 |  |  |  | 110 |  |  |  |
| Leu | Pro | Gly | Gly | Val | Tyr | Ala | Leu | Asn | Gly | Thr | Ile | Asn | Ala | Val | Thr |
|  |  | 115 |  |  |  | 120 |  |  |  | 125 |  |  |  |
| Phe | Gln | Gly | Ser | Leu | Ser | Glu | Leu | Thr | Asp | Val | Ser | Tyr | Asn | Gly | Leu |
|  | 130 |  |  |  |  | 135 |  |  |  |  | 140 |  |  |  |
| Met | Ser | Ala | Thr | Ala | Asn | Ile | Asn | Asp | Lys | Ile | Gly | Asn | Val | Leu | Val |
| 145 |  |  |  |  | 150 |  |  |  |  | 155 |  |  |  |  | 160 |
| Gly | Glu | Gly | Val | Thr | Val | Leu | Ser | Leu | Pro | Thr | Ser | Tyr | Asp | Leu | Gly |
|  |  |  |  | 165 |  |  |  |  | 170 |  |  |  |  | 175 |
| Tyr | Val | Arg | Leu | Gly | Asp | Pro | Ile | Pro | Ala | Ile | Gly | Leu | Asp | Pro | Lys |
|  |  |  | 180 |  |  |  |  | 185 |  |  |  |  | 190 |  |
| Met | Val | Ala | Thr | Cys | Asp | Ser | Ser | Asp | Arg | Pro | Arg | Val | Tyr | Thr | Ile |
|  |  |  | 195 |  |  |  |  | 200 |  |  |  |  | 205 |  |
| Thr | Ala | Ala | Asp | Asp | Tyr | Gln | Phe | Ser | Ser | Gln | Tyr | Gln | Pro | Gly | Gly |
|  | 210 |  |  |  |  | 215 |  |  |  |  | 220 |  |  |  |
| Val | Thr | Ile | Thr | Leu | Phe | Ser | Ala | Asn | Ile | Asp | Ala | Ile | Thr | Ser | Leu |
| 225 |  |  |  |  | 230 |  |  |  |  | 235 |  |  |  |  | 240 |
| Ser | Ile | Gly | Gly | Glu | Leu | Val | Phe | Gln | Thr | Ser | Val | Gln | Gly | Leu | Val |
|  |  |  |  | 245 |  |  |  |  | 250 |  |  |  |  | 255 |
| Leu | Gly | Ala | Thr | Ile | Tyr | Leu | Ile | Gly | Phe | Asp | Gly | Thr | Ala | Val | Ile |
|  |  |  | 260 |  |  |  |  | 265 |  |  |  |  | 270 |  |
| Thr | Arg | Ala | Val | Ala | Ala | Asp | Asn | Gly | Leu | Thr | Ala | Gly | Thr | Asp | Asn |
|  |  | 275 |  |  |  |  | 280 |  |  |  |  | 285 |  |  |
| Leu | Met | Pro | Phe | Asn | Leu | Val | Ile | Pro | Thr | Asn | Glu | Ile | Thr | Gln | Pro |
|  | 290 |  |  |  |  | 295 |  |  |  |  | 300 |  |  |  |
| Ile | Thr | Ser | Ile | Lys | Leu | Glu | Ile | Val | Thr | Ser | Lys | Ser | Gly | Gly | Gln |
| 305 |  |  |  |  | 310 |  |  |  |  | 315 |  |  |  |  | 320 |
| Ala | Gly | Asp | Gln | Met | Ser | Trp | Ser | Ala | Ser | Gly | Ser | Leu | Ala | Val | Thr |
|  |  |  |  | 325 |  |  |  |  | 330 |  |  |  |  | 335 |
| Ile | His | Gly | Gly | Asn | Tyr | Pro | Gly | Ala | Leu | Arg | Pro | Val | Thr | Leu | Val |
|  |  |  | 340 |  |  |  |  | 345 |  |  |  |  | 350 |  |
| Ala | Tyr | Glu | Arg | Val | Ala | Thr | Gly | Ser | Val | Val | Thr | Val | Ala | Gly | Val |
|  |  | 355 |  |  |  |  | 360 |  |  |  |  | 365 |  |  |
| Ser | Asn | Phe | Glu | Leu | Ile | Pro | Asn | Pro | Glu | Leu | Ala | Lys | Asn | Leu | Val |
|  | 370 |  |  |  |  | 375 |  |  |  |  | 380 |  |  |  |
| Thr | Glu | Tyr | Gly | Arg | Phe | Asp | Pro | Gly | Ala | Met | Asn | Tyr | Thr | Lys | Leu |
| 385 |  |  |  |  | 390 |  |  |  |  | 395 |  |  |  |  | 400 |
| Ile | Leu | Ser | Glu | Arg | Asp | Arg | Leu | Gly | Ile | Lys | Thr | Val | Trp | Pro | Thr |
|  |  |  |  | 405 |  |  |  |  | 410 |  |  |  |  | 415 |
| Arg | Glu | Tyr | Thr | Asp | Phe | Arg | Glu | Tyr | Phe | Met | Glu | Val | Ala | Asp | Leu |
|  |  |  | 420 |  |  |  |  | 425 |  |  |  |  | 430 |  |
| Asn | Ser | Pro | Leu | Lys | Ile | Ala | Gly | Ala | Phe | Gly | Phe | Lys | Asp | Ile | Ile |
|  |  | 435 |  |  |  |  | 440 |  |  |  |  | 445 |  |  |
| Arg | Ala | Ile | Arg | Arg | Ile | Ala | Val | Pro | Val | Val | Ser | Thr | Leu | Phe | Pro |
|  | 450 |  |  |  |  | 455 |  |  |  |  | 460 |  |  |  |
| Pro | Ala | Ala | Pro | Leu | Ala | His | Ala | Ile | Gly | Glu | Gly | Val | Asp | Tyr | Leu |
| 465 |  |  |  |  | 470 |  |  |  |  | 475 |  |  |  |  | 480 |
| Leu | Gly | Asp | Glu | Ala | Gln | Ala | Ala | Ser | Gly | Thr | Ala | Arg | Ala | Ala | Ser |
|  |  |  |  | 485 |  |  |  |  | 490 |  |  |  |  | 495 |
| Gly | Lys | Ala | Arg | Ala | Ala | Ser | Gly | Arg | Ile | Arg | Gln | Leu | Thr | Leu | Ala |
|  |  |  | 500 |  |  |  |  | 505 |  |  |  |  | 510 |  |
| Ala | Asp | Lys | Gly | Tyr | Glu | Val | Val | Ala | Asn | Leu | Phe | Gln | Val | Pro | Gln |
|  |  | 515 |  |  |  |  | 520 |  |  |  |  | 525 |  |  |

```
Asn  Pro  Val  Val  Asp  Gly  Ile  Leu  Ala  Ser  Pro  Gly  Val  Leu  Arg  Gly
     530                 535                      540

Ala  His  Asn  Leu  Asp  Cys  Val  Leu  Arg  Glu  Gly  Ala  Thr  Leu  Phe  Pro
545                      550                 555                           560

Val  Val  Ile  Thr  Thr  Val  Glu  Asp  Ala  Met  Thr  Pro  Lys  Ala  Leu  Asn
               565                      570                      575

Ser  Lys  Met  Phe  Ala  Val  Ile  Glu  Gly  Val  Arg  Glu  Asp  Leu  Gln  Pro
               580                 585                           590

Pro  Ser  Gln  Arg  Gly  Ser  Phe  Ile  Arg  Thr  Leu  Ser  Gly  His  Arg  Val
          595                      600                 605

Tyr  Gly  Tyr  Ala  Pro  Asp  Gly  Val  Leu  Pro  Leu  Glu  Thr  Gly  Arg  Asp
     610                 615                      620

Tyr  Thr  Val  Val  Pro  Ile  Asp  Asp  Val  Trp  Asp  Asp  Ser  Ile  Met  Leu
625                      630                 635                           640

Ser  Lys  Asp  Pro  Ile  Pro  Pro  Ile  Val  Gly  Asn  Ser  Gly  Asn  Leu  Ala
               645                      650                      655

Ile  Ala  Tyr  Met  Asp  Val  Phe  Arg  Pro  Lys  Val  Pro  Ile  His  Val  Ala
               660                      665                      670

Met  Thr  Gly  Ala  Pro  Asn  Ala  Cys  Gly  Glu  Ile  Glu  Lys  Ile  Ser  Phe
          675                      680                 685

Arg  Ser  Thr  Lys  Leu  Ala  Thr  Ala  His  Arg  Leu  Gly  Leu  Lys  Leu  Ala
     690                 695                      700

Gly  Pro  Gly  Ala  Phe  Asp  Val  Asn  Thr  Gly  Pro  Asn  Trp  Ala  Thr  Phe
705                      710                      715                      720

Ile  Lys  Arg  Phe  Pro  His  Asn  Pro  Arg  Asp  Trp  Asp  Arg  Leu  Pro  Tyr
               725                      730                      735

Leu  Asn  Leu  Pro  Tyr  Leu  Pro  Pro  Asn  Ala  Gly  Arg  Gln  Tyr  His  Leu
               740                      745                 750

Ala  Met  Ala  Ala  Ser  Glu  Phe  Lys  Asp  Thr  Pro  Glu  Leu  Glu  Ser  Ala
               755                 760                      765

Val  Arg  Ala  Met  Glu  Ala  Ala  Ala  Asn  Val  Asp  Ser  Leu  Phe  Gln  Ser
     770                 775                      780

Ala  Leu  Ser  Val  Phe  Met  Trp  Leu  Glu  Glu  Asn  Gly  Ile  Val  Thr  Asp
785                      790                      795                      800

Met  Ala  Asn  Phe  Thr  Leu  Ser  Asp  Pro  Asn  Ala  His  Arg  Met  Arg  Asn
               805                      810                      815

Phe  Leu  Ala  Asn  Ala  Pro  Gln  Ala  Gly  Ser  Lys  Ser  Gln  Arg  Ala  Lys
               820                      825                      830

Tyr  Gly  Thr  Ala  Gly  Tyr  Gly  Val  Glu  Ala  Arg  Gly  Pro  Thr  Pro  Glu
          835                      840                      845

Glu  Ala  Gln  Arg  Lys  Lys  Asp  Thr  Arg  Ile  Ser  Lys  Lys  Met  Glu  Thr
     850                      855                      860

Met  Gly  Ile  Tyr  Phe  Ala  Thr  Pro  Glu  Trp  Val  Ala  Leu  Asn  Gly  His
865                      870                 875                           880

Arg  Gly  Pro  Ser  Pro  Gly  Gln  Leu  Lys  Tyr  Trp  Gln  Asn  Thr  Arg  Glu
                    885                      890                           895

Ile  Pro  Asp  Pro  Asn  Glu  Asp  Tyr  Leu  Asp  Tyr  Val  His  Ala  Glu  Lys
               900                      905                 910

Ser  Arg  Leu  Ala  Ser  Asp  Glu  Gln  Ile  Leu  Arg  Ala  Ala  Thr  Ser  Ile
          915                      920                 925

Tyr  Gly  Ala  Pro  Gly  Gln  Ala  Glu  Pro  Pro  Gln  Ala  Phe  Ile  Asp  Glu
     930                      935                 940

Val  Ala  Lys  Val  Tyr  Glu  Ile  Asn  His  Gly  Arg  Gly  Pro  Asn  Gln  Glu
945                      950                 955                           960
```

|   |     |     |     |     |     |     |     |     |     |     |     |     |     |     |
|---|-----|-----|-----|-----|-----|-----|-----|-----|-----|-----|-----|-----|-----|-----|
| Gln | Met | Lys | Asp | Leu<br>965 | Leu | Leu | Thr | Ala | Met<br>970 | Glu | Met | Lys | His<br>975 | Arg | Asn |
| Pro | Arg | Arg | Ala<br>980 | Pro | Pro | Lys | Pro<br>985 | Lys | Pro | Lys | Pro | Asn<br>990 | Ala | Pro | Thr |
| Gln | Arg | Pro<br>995 | Pro | Gly | Arg | Leu | Gly<br>1000 | Arg | Trp | Ile | Arg | Thr<br>1005 | Val | Ser | Asp |
| Glu | Asp | Leu | Glu<br>1010 | | | | | | | | | | | | |

( 2 ) INFORMATION FOR SEQ ID NO:8:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: STC ( x i ) SEQUENCE DESCRIPTION: SEQ ID NO:8:

|   |     |     |     |     |     |     |     |     |     |     |     |     |     |     |
|---|-----|-----|-----|-----|-----|-----|-----|-----|-----|-----|-----|-----|-----|-----|
| Met<br>1 | Thr | Asn | Leu | Gln<br>5 | Asp | Gln | Thr | Gln | Gln<br>10 | Ile | Val | Pro | Phe | Ile<br>15 | Arg |
| Ser | Leu | Leu | Met<br>20 | Pro | Thr | Thr | Gly | Pro<br>25 | Ala | Ser | Ile | Pro | Asp<br>30 | Asp | Thr |
| Leu | Glu | Lys<br>35 | His | Thr | Leu | Arg | Ser<br>40 | Glu | Thr | Ser | Thr | Tyr<br>45 | Asn | Leu | Thr |
| Val | Gly<br>50 | Asp | Thr | Gly | Ser<br>55 | Gly | Leu | Ile | Val | Phe<br>60 | Phe | Pro | Gly | Phe | Pro |
| Gly<br>65 | Ser | Ile | Val | Gly<br>70 | Ala | His | Tyr | Thr | Leu<br>75 | Gln | Ser | Asn | Gly | Asn | Leu<br>80 |
| Lys | Phe | Asp | Gln | Met<br>85 | Leu | Leu | Thr | Ala | Gln<br>90 | Asn | Leu | Pro | Ala | Ser<br>95 | Tyr |
| Asn | Tyr | Cys | Arg<br>100 | Leu | Val | Ser | Arg | Ser<br>105 | Leu | Thr | Val | Arg | Ser<br>110 | Ser | Thr |
| Leu | Pro | Gly<br>115 | Gly | Val | Tyr | Ala | Leu<br>120 | Asn | Gly | Thr | Ile | Asn<br>125 | Ala | Val | Thr |
| Phe | Gln<br>130 | Gly | Ser | Leu | Ser | Glu<br>135 | Leu | Thr | Asp | Val | Ser<br>140 | Tyr | Asn | Gly | Leu |
| Met<br>145 | Ser | Ala | Thr | Ala | Asn<br>150 | Ile | Asn | Asp | Lys | Ile<br>155 | Gly | Asn | Val | Leu | Val<br>160 |
| Gly | Glu | Gly | Val | Thr<br>165 | Val | Leu | Ser | Leu | Pro<br>170 | Thr | Ser | Tyr | Asp | Leu<br>175 | Gly |
| Tyr | Val | Arg | Leu<br>180 | Gly | Asp | Pro | Ile | Pro<br>185 | Ala | Ile | Gly | Leu | Asp<br>190 | Pro | Lys |
| Met | Val | Ala | Thr<br>195 | Cys | Asp | Ser | Ser | Asp<br>200 | Arg | Pro | Arg | Val | Tyr<br>205 | Thr | Ile |
| Thr | Ala<br>210 | Ala | Asp | Asp | Tyr | Gln<br>215 | Phe | Ser | Ser | Gln | Tyr<br>220 | Gln | Pro | Gly | Gly |
| Val<br>225 | Thr | Ile | Thr | Leu | Phe<br>230 | Ser | Ala | Asn | Ile | Asp<br>235 | Ala | Ile | Thr | Ser | Leu<br>240 |
| Ser | Val | Gly | Gly | Glu<br>245 | Leu | Val | Phe | Gln | Thr<br>250 | Ser | Val | Gln | Gly | Leu<br>255 | Val |
| Leu | Gly | Ala | Thr | Ile<br>260 | Tyr | Phe | Ile | Gly | Phe<br>265 | Asp | Gly | Thr | Thr<br>270 | Val | Ile |

| | | | | | | | | | | | | | | |
|---|---|---|---|---|---|---|---|---|---|---|---|---|---|---|
| Thr | Arg | Ala 275 | Val | Ala | Ala | Asp | Asn 280 | Gly | Leu | Thr | Ala 285 | Thr | Asp | Asn |
| Leu | Met 290 | Pro | Phe | Asn | Leu | Val 295 | Ile | Pro | Thr | Asn 300 | Glu | Ile | Thr | Gln | Pro |
| Ile 305 | Thr | Ser | Ile | Lys | Leu 310 | Glu | Val | Val | Thr | Ser 315 | Lys | Ser | Gly | Gly | Gln 320 |
| Ala | Gly | Asp | Gln | Met 325 | Ser | Trp | Ser | Ala | Ser 330 | Gly | Ser | Leu | Ala | Val 335 | Thr |
| Ile | His | Gly | Gly 340 | Asn | Tyr | Pro | Gly | Ala 345 | Leu | Arg | Pro | Val | Thr 350 | Leu | Val |
| Ala | Tyr | Glu 355 | Arg | Val | Ala | Thr | Gly 360 | Ser | Val | Val | Thr | Val 365 | Ala | Gly | Val |
| Ser | Asn 370 | Phe | Glu | Leu | Ile | Pro 375 | Asn | Pro | Glu | Leu 380 | Ala | Lys | Asn | Leu | Val |
| Thr 385 | Glu | Tyr | Gly | Arg | Phe 390 | Asp | Pro | Gly | Ala | Met 395 | Asn | Tyr | Thr | Lys | Leu 400 |
| Ile | Leu | Ser | Glu | Arg 405 | Asp | Arg | Leu | Gly | Ile 410 | Lys | Thr | Val | Trp | Pro 415 | Thr |
| Arg | Glu | Tyr | Thr 420 | Asp | Phe | Arg | Glu | Tyr 425 | Phe | Met | Glu | Val | Ala 430 | Asp | Leu |
| Asn | Ser | Pro 435 | Leu | Lys | Ile | Ala | Gly 440 | Ala | Phe | Gly | Phe | Lys 445 | Asp | Ile | Ile |
| Arg | Ala 450 | Ile | Arg | Arg | Ile | Ala 455 | Val | Pro | Val | Val | Ser 460 | Thr | Leu | Phe | Pro |
| Pro 465 | Ala | Ala | Pro | Leu | Ala 470 | His | Ala | Ile | Gly | Glu 475 | Gly | Val | Asp | Tyr | Leu 480 |
| Leu | Gly | Asp | Glu | Ala 485 | Gln | Ala | Ala | Ser | Gly 490 | Thr | Ala | Arg | Ala | Ala 495 | Ser |
| Gly | Lys | Ala | Arg 500 | Ala | Ala | Ser | Gly | Arg 505 | Ile | Arg | Gln | Leu | Thr 510 | Leu | Ala |
| Ala | Asp | Lys 515 | Gly | Tyr | Glu | Val | Val 520 | Ala | Asn | Leu | Phe | Gln 525 | Val | Pro | Gln |
| Asn | Pro 530 | Val | Val | Asp | Gly | Ile 535 | Leu | Ala | Ser | Pro | Gly 540 | Val | Leu | Arg | Gly |
| Ala 545 | His | Asn | Leu | Asp | Cys 550 | Val | Leu | Arg | Glu | Gly 555 | Ala | Thr | Leu | Phe | Pro 560 |
| Val | Val | Ile | Thr | Thr 565 | Val | Glu | Asp | Ala | Met 570 | Thr | Pro | Lys | Ala | Leu 575 | Asn |
| Ser | Lys | Ile | Phe 580 | Ala | Val | Ile | Glu | Gly 585 | Val | Arg | Glu | Asp | Leu 590 | Gln | Pro |
| Pro | Ser | Gln 595 | Arg | Gly | Ser | Phe | Ile 600 | Arg | Thr | Leu | Ser | Gly 605 | His | Arg | Val |
| Tyr | Gly 610 | Tyr | Ala | Pro | Asp | Gly 615 | Val | Leu | Pro | Leu | Glu 620 | Thr | Gly | Arg | Asp |
| Tyr 625 | Thr | Val | Val | Pro | Ile 630 | Asp | Asp | Val | Trp | Asp 635 | Asp | Ser | Ile | Met | Leu 640 |
| Ser | Lys | Asp | Pro | Ile 645 | Pro | Pro | Ile | Val | Gly 650 | Asn | Ser | Gly | Asn | Leu 655 | Ala |
| Ile | Ala | Tyr | Met 660 | Asp | Val | Phe | Arg | Pro 665 | Lys | Val | Pro | Ile 670 | His | Val | Ala |
| Met | Thr | Gly 675 | Ala | Leu | Asn | Ala | Phe 680 | Gly | Glu | Ile | Glu | Lys 685 | Val | Ser | Phe |
| Arg | Ser | Thr | Lys | Leu | Ala | Thr | Ala | His | Arg | Leu | Gly | Leu | Lys | Leu | Ala |

|     |     |     |     | 690 |     |     |     | 695 |     |     |     | 700 |     |     |
| --- | --- | --- | --- | --- | --- | --- | --- | --- | --- | --- | --- | --- | --- | --- |
| Gly | Pro | Gly | Ala | Phe | Asp | Val | Asn | Thr | Gly | Pro | Asn | Trp | Ala | Thr | Phe |
| 705 |     |     |     | 710 |     |     |     | 715 |     |     |     |     |     |     | 720 |
| Ile | Lys | Arg | Phe | Pro | His | Asn | Pro | Arg | Asp | Trp | Asp | Arg | Leu | Pro | Tyr |
|     |     |     |     | 725 |     |     |     | 730 |     |     |     |     |     | 735 |     |
| Leu | Asn | Leu | Pro | Tyr | Leu | Pro | Pro | Asn | Ala | Gly | Arg | Gln | Tyr | His | Leu |
|     |     |     | 740 |     |     |     | 745 |     |     |     |     |     | 750 |     |     |
| Ala | Met | Ala | Ala | Ser | Glu | Phe | Lys | Glu | Thr | Pro | Glu | Leu | Glu | Ser | Ala |
|     |     | 755 |     |     |     |     | 760 |     |     |     |     | 765 |     |     |     |
| Val | Arg | Ala | Met | Glu | Ala | Ala | Asn | Val | Asp | Pro | Leu | Phe | Gln | Ser |
|     | 770 |     |     |     | 775 |     |     |     |     | 780 |     |     |     |     |
| Ala | Leu | Ser | Val | Phe | Met | Trp | Leu | Glu | Glu | Asn | Gly | Ile | Val | Thr | Asp |
| 785 |     |     |     |     | 790 |     |     |     |     | 795 |     |     |     |     | 800 |
| Met | Ala | Asn | Phe | Ala | Leu | Ser | Asp | Pro | Asn | Ala | His | Arg | Met | Arg | Asn |
|     |     |     |     | 805 |     |     |     |     | 810 |     |     |     |     | 815 |     |
| Phe | Leu | Ala | Asn | Ala | Pro | Gln | Ala | Gly | Ser | Lys | Ser | Gln | Arg | Ala | Lys |
|     |     |     | 820 |     |     |     |     | 825 |     |     |     |     | 830 |     |     |
| Tyr | Gly | Thr | Ala | Gly | Tyr | Gly | Val | Glu | Ala | Arg | Gly | Pro | Thr | Pro | Glu |
|     |     | 835 |     |     |     |     | 840 |     |     |     |     | 845 |     |     |     |
| Glu | Ala | Gln | Arg | Ala | Lys | Asp | Thr | Arg | Ile | Ser | Lys | Lys | Met | Glu | Thr |
|     | 850 |     |     |     |     | 855 |     |     |     |     | 860 |     |     |     |     |
| Met | Gly | Ile | Tyr | Phe | Ala | Thr | Pro | Glu | Trp | Val | Ala | Leu | Asn | Gly | His |
| 865 |     |     |     |     | 870 |     |     |     |     | 875 |     |     |     |     | 880 |
| Arg | Gly | Pro | Ser | Pro | Ala | Gln | Leu | Lys | Tyr | Trp | Gln | Asn | Thr | Arg | Glu |
|     |     |     |     | 885 |     |     |     |     | 890 |     |     |     |     | 895 |     |
| Ile | Pro | Asp | Pro | Asn | Glu | Asp | Tyr | Leu | Asp | Tyr | Val | His | Ala | Glu | Lys |
|     |     |     | 900 |     |     |     |     | 905 |     |     |     |     | 910 |     |     |
| Ser | Arg | Leu | Ala | Ser | Glu | Glu | Gln | Ile | Leu | Lys | Ala | Ala | Thr | Ser | Ile |
|     |     | 915 |     |     |     |     | 920 |     |     |     |     | 925 |     |     |     |
| Tyr | Gly | Ala | Pro | Gly | Gln | Ala | Glu | Pro | Pro | Gln | Ala | Phe | Ile | Asp | Glu |
|     |     | 930 |     |     |     |     | 935 |     |     |     |     | 940 |     |     |     |
| Val | Ala | Lys | Val | Tyr | Glu | Ile | Asn | His | Gly | Arg | Gly | Pro | Asn | Gln | Glu |
| 945 |     |     |     |     | 950 |     |     |     |     | 955 |     |     |     |     | 960 |
| Gln | Met | Lys | Asp | Leu | Leu | Leu | Thr | Ala | Met | Glu | Leu | Lys | His | Arg | Asn |
|     |     |     |     | 965 |     |     |     |     | 970 |     |     |     |     | 975 |     |
| Pro | Arg | Arg | Ala | Pro | Pro | Lys | Pro | Lys | Pro | Lys | Pro | Asn | Ala | Pro | Thr |
|     |     |     | 980 |     |     |     |     | 985 |     |     |     |     | 990 |     |     |
| Gln | Arg | Pro | Pro | Gly | Arg | Leu | Gly | Arg | Trp | Ile | Arg | Thr | Val | Ser | Asp |
|     |     | 995 |     |     |     |     | 1000|     |     |     |     | 1005|     |     |     |
| Glu | Asp | Leu | Glu |     |     |     |     |     |     |     |     |     |     |     |     |
|     |     | 1010|     |     |     |     |     |     |     |     |     |     |     |     |     |

( 2 ) INFORMATION FOR SEQ ID NO:9:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: 002-73

( x i ) SEQUENCE DESCRIPTION: SEQ ID NO:9:

| Met | Thr | Asn | Leu | Ser | Asp | Gln | Thr | Gln | Gln | Ile | Val | Pro | Phe | Ile | Arg |
| --- | --- | --- | --- | --- | --- | --- | --- | --- | --- | --- | --- | --- | --- | --- | --- |

-continued

```
  1                    5                        10                      15

Ser   Leu   Leu   Met   Pro   Thr   Thr   Gly   Pro   Ala   Ser   Ile   Pro   Asp   Thr
                  20                      25                      30

Leu   Glu   Lys   His   Thr   Leu   Arg   Ser   Glu   Thr   Ser   Thr   Tyr   Asn   Leu   Thr
            35                            40                            45

Val   Gly   Asp   Thr   Gly   Ser   Gly   Leu   Ile   Val   Phe   Phe   Pro   Gly   Phe   Pro
      50                      55                            60

Gly   Ser   Ile   Val   Gly   Ala   His   Tyr   Met   Leu   Gln   Ser   Asn   Gly   Asn   Tyr
65                            70                      75                            80

Lys   Phe   Asp   Gln   Met   Leu   Leu   Thr   Ala   Gln   Asn   Leu   Pro   Ala   Ser   Tyr
                  85                      90                            95

Asn   Tyr   Cys   Arg   Leu   Val   Ser   Arg   Ser   Leu   Thr   Val   Arg   Ser   Ser   Thr
            100                           105                           110

Leu   Pro   Gly   Gly   Val   Tyr   Ala   Leu   Asn   Gly   Thr   Ile   Asn   Ala   Val   Thr
            115                           120                           125

Phe   Gln   Gly   Ser   Leu   Ser   Glu   Leu   Thr   Asp   Val   Ser   Tyr   Asn   Gly   Leu
      130                           135                     140

Met   Ser   Ala   Thr   Ala   Asn   Ile   Asn   Asp   Lys   Ile   Gly   Asn   Val   Leu   Val
145                           150                     155                           160

Gly   Glu   Gly   Val   Thr   Val   Leu   Ser   Leu   Pro   Thr   Ser   Tyr   Asp   Leu   Gly
                        165                     170                           175

Tyr   Val   Arg   Leu   Gly   Asp   Pro   Ile   Pro   Ala   Ile   Gly   Leu   Asp   Pro   Lys
            180                     185                           190

Met   Val   Ala   Thr   Cys   Asp   Ser   Ser   Asp   Arg   Pro   Arg   Val   Tyr   Thr   Ile
            195                     200                     205

Thr   Ala   Ala   Asp   Asp   Tyr   Gln   Phe   Ser   Ser   Gln   Tyr   Gln   Pro   Gly   Gly
      210                     215                     220

Val   Thr   Ile   Thr   Leu   Phe   Ser   Ala   Asn   Ile   Asp   Ala   Ile   Asn   Ser   Leu
225                     230                           235                           240

Ser   Val   Gly   Gly   Glu   Leu   Val   Phe   Gln   Thr   Ser   Val   Gln   Gly   Leu   Val
                  245                     250                           255

Leu   Asn   Ala   Thr   Ile   Tyr   Leu   Val   Gly   Phe   Asp   Gly   Thr   Thr   Val   Thr
                  260                     265                     270

Thr   Arg   Ala   Val   Ala   Ala   Gly   Asn   Gly   Leu   Thr   Ala   Gly   Thr   Asp   Asn
            275                     280                     285

Leu   Met   Pro   Phe   Asn   Leu   Val   Ile   Pro   Thr   Ser   Glu   Ile   Thr   Gln   Pro
      290                     295                     300

Val   Thr   Ser   Ile   Lys   Leu   Glu   Ile   Val   Thr   Ser   Lys   Ser   Gly   Gly   Gln
305                     310                     315                           320

Ala   Gly   Asp   Gln   Met   Ser   Trp   Leu   Ala   Ser   Gly   Asn   Leu   Ala   Val   Thr
                  325                     330                           335

Ile   His   Gly   Gly   Asn   Tyr   Pro   Gly   Ala   Leu   Arg   Pro   Val   Thr   Leu   Val
                  340                     345                     350

Ala   Tyr   Glu   Arg   Val   Ala   Thr   Gly   Ser   Val   Val   Thr   Val   Ala   Gly   Val
            355                     360                     365

Ser   Asn   Phe   Glu   Leu   Ile   Pro   Asn   Pro   Glu   Leu   Ala   Lys   Asn   Leu   Val
      370                     375                     380

Thr   Glu   Tyr   Gly   Arg   Phe   Asp   Pro   Gly   Ala   Met   Asn   Tyr   Thr   Lys   Leu
385                     390                     395                           400

Ile   Leu   Ser   Glu   Arg   Asp   Arg   Leu   Gly   Ile   Lys   Thr   Val   Trp   Pro   Thr
                  405                     410                           415

Arg   Glu   Tyr   Thr   Asp   Phe   Arg   Glu   Tyr   Phe   Met   Glu   Val   Ala   Asp   Leu
                  420                     425                           430
```

```
Asn  Ser  Pro  Leu  Lys  Ile  Ala  Gly  Ala  Phe  Gly  Phe  Lys  Asp  Ile  Ile
          435                 440                      445

Arg  Ala  Ile  Arg  Arg  Ile  Ala  Val  Pro  Val  Val  Ser  Thr  Leu  Phe  Pro
     450                 455                      460

Pro  Ala  Ala  Pro  Leu  Ala  His  Ala  Ile  Gly  Glu  Gly  Val  Asp  Tyr  Leu
465                      470                 475                           480

Leu  Gly  Asp  Glu  Ala  Gln  Ala  Ala  Ser  Gly  Thr  Ala  Arg  Ala  Ala  Ser
                    485                      490                           495

Gly  Lys  Ala  Arg  Ala  Ala  Ser  Gly  Arg  Ile  Arg  Gln  Leu  Thr  Leu  Ala
               500                      505                      510

Ala  Asp  Lys  Gly  Tyr  Glu  Val  Val  Ala  Asn  Leu  Phe  Gln  Val  Pro  Gln
          515                      520                      525

Asn  Pro  Val  Val  Asp  Gly  Ile  Leu  Ala  Ser  Pro  Gly  Val  Leu  Arg  Gly
     530                      535                      540

Ala  His  Asn  Leu  Asp  Cys  Val  Leu  Arg  Glu  Gly  Ala  Thr  Leu  Phe  Pro
545                           550                      555                 560

Val  Val  Ile  Thr  Thr  Val  Glu  Asp  Ala  Met  Thr  Pro  Lys  Ala  Leu  Asn
                    565                      570                      575

Ser  Lys  Met  Phe  Ala  Val  Ile  Glu  Gly  Val  Arg  Glu  Asp  Leu  Gln  Pro
               580                      585                      590

Pro  Ser  Gln  Arg  Gly  Ser  Phe  Ile  Arg  Thr  Leu  Ser  Gly  His  Arg  Val
          595                      600                      605

Tyr  Gly  Tyr  Ala  Pro  Asp  Gly  Val  Leu  Pro  Leu  Glu  Thr  Gly  Arg  Asp
     610                      615                      620

Tyr  Thr  Val  Val  Pro  Ile  Asp  Asp  Val  Trp  Asp  Asp  Ser  Ile  Met  Leu
625                      630                      635                      640

Ser  Lys  Asp  Pro  Ile  Pro  Pro  Ile  Val  Gly  Asn  Ser  Gly  Asn  Leu  Ala
                    645                      650                      655

Ile  Ala  Tyr  Met  Asp  Val  Phe  Arg  Pro  Lys  Val  Pro  Ile  His  Val  Ala
               660                      665                      670

Met  Thr  Gly  Ala  Leu  Asn  Ala  Cys  Gly  Glu  Val  Glu  Lys  Val  Ser  Phe
          675                      680                      685

Arg  Ser  Thr  Lys  Leu  Ala  Thr  Ala  His  Arg  Leu  Gly  Leu  Lys  Leu  Ala
     690                      695                      700

Gly  Pro  Gly  Ala  Phe  Asp  Ile  Asn  Thr  Gly  Pro  Asn  Trp  Ala  Thr  Phe
705                      710                      715                      720

Ile  Lys  Arg  Phe  Pro  His  Asn  Pro  Arg  Asp  Trp  Asp  Arg  Leu  Pro  Tyr
                    725                      730                      735

Leu  Asn  Leu  Pro  Tyr  Leu  Pro  Pro  Ser  Ala  Gly  Arg  Gln  Tyr  His  Leu
               740                      745                      750

Ala  Met  Ala  Ala  Ser  Glu  Phe  Lys  Glu  Thr  Pro  Glu  Leu  Glu  Ser  Ala
          755                      760                      765

Val  Arg  Ala  Met  Glu  Ala  Ala  Asp  Val  Asp  Pro  Leu  Phe  Gln  Ser
     770                      775                      780

Ala  Leu  Ser  Val  Phe  Met  Trp  Leu  Glu  Glu  Asn  Gly  Ile  Val  Thr  Asp
785                      790                      795                      800

Met  Ala  Asn  Phe  Ala  Leu  Ser  Asp  Pro  Asn  Ala  His  Arg  Met  Arg  Asn
                    805                      810                      815

Phe  Leu  Ala  Asn  Ala  Pro  Gln  Ala  Gly  Ser  Lys  Ser  Gln  Arg  Ala  Lys
               820                      825                      830

Tyr  Gly  Thr  Ala  Gly  Tyr  Gly  Val  Glu  Ala  Arg  Gly  Pro  Thr  Pro  Glu
          835                      840                      845

Glu  Ala  Gln  Arg  Glu  Lys  Asp  Thr  Arg  Ile  Ser  Lys  Lys  Met  Glu  Ala
850                      855                      860
```

| Met | Gly | Ile | Tyr | Phe | Ala | Thr | Pro | Glu | Trp | Val | Ala | Leu | Asn | Gly | His |
|-----|-----|-----|-----|-----|-----|-----|-----|-----|-----|-----|-----|-----|-----|-----|-----|
| 865 |     |     |     |     | 870 |     |     |     | 875 |     |     |     |     |     | 880 |
| Arg | Gly | Pro | Ser | Pro | Gly | Gln | Leu | Lys | Tyr | Trp | Gln | Asn | Thr | Arg | Glu |
|     |     |     |     | 885 |     |     |     |     | 890 |     |     |     |     | 895 |     |
| Ile | Pro | Asp | Pro | Asn | Glu | Asp | Tyr | Leu | Asp | Tyr | Val | His | Ala | Glu | Lys |
|     |     |     | 900 |     |     |     |     |     | 905 |     |     |     | 910 |     |     |
| Ser | Arg | Leu | Ala | Ser | Glu | Glu | Gln | Ile | Leu | Arg | Ala | Ala | Thr | Ser | Ile |
|     |     | 915 |     |     |     |     | 920 |     |     |     |     | 925 |     |     |     |
| Tyr | Gly | Ala | Pro | Gly | Gln | Ala | Glu | Pro | Pro | Gln | Ala | Phe | Ile | Asp | Glu |
|     | 930 |     |     |     |     | 935 |     |     |     |     | 940 |     |     |     |     |
| Val | Ala | Lys | Val | Tyr | Glu | Ile | Asn | His | Gly | Arg | Gly | Pro | Asn | Gln | Glu |
| 945 |     |     |     |     | 950 |     |     |     |     | 955 |     |     |     |     | 960 |
| Gln | Met | Lys | Asp | Leu | Leu | Leu | Thr | Ala | Met | Glu | Met | Lys | His | Arg | Asn |
|     |     |     |     | 965 |     |     |     |     | 970 |     |     |     |     | 975 |     |
| Pro | Arg | Arg | Ala | Pro | Pro | Lys | Pro | Lys | Pro | Lys | Pro | Asn | Ala | Pro | Ser |
|     |     |     | 980 |     |     |     |     | 985 |     |     |     |     | 990 |     |     |
| Gln | Arg | Pro | Pro | Gly | Arg | Leu | Gly | Arg | Trp | Ile | Arg | Thr | Val | Ser | Asp |
|     |     | 995 |     |     |     |     | 1000|     |     |     |     | 1005|     |     |     |
| Glu | Asp | Leu | Glu |
|     |     |1010 |     |

( 2 ) INFORMATION FOR SEQ ID NO:10:

( i ) SEQUENCE CHARACTERISTICS:
        ( A ) LENGTH: 1012 amino acids
        ( B ) TYPE: amino acid
        ( C ) STRANDEDNESS:
        ( D ) TOPOLOGY: unknown ( i i ) MOLECULE TYPE: protein ( v i ) ORIGINAL SOURCE:
        ( A ) ORGANISM: Infectious bursal disease virus
        ( B ) STRAIN: OH ( x i ) SEQUENCE DESCRIPTION: SEQ ID NO:10:

| Met | Thr | Asn | Leu | Met | Asp | His | Thr | Gln | Gln | Ile | Val | Pro | Phe | Ile | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Leu | Met | Pro | Thr | Thr | Gly | Pro | Ala | Ser | Ile | Pro | Asp | Asp | Thr |
|     |     |     | 20  |     |     |     |     | 25  |     |     |     |     | 30  |     |     |
| Leu | Glu | Lys | His | Thr | Leu | Arg | Ser | Glu | Thr | Ser | Thr | Tyr | Asn | Leu | Thr |
|     |     | 35  |     |     |     |     | 40  |     |     |     |     | 45  |     |     |     |
| Val | Gly | Asp | Thr | Gly | Ser | Gly | Leu | Ile | Val | Phe | Phe | Pro | Gly | Phe | Pro |
|     | 50  |     |     |     |     | 55  |     |     |     |     | 60  |     |     |     |     |
| Gly | Ser | Val | Val | Gly | Ala | His | Tyr | Thr | Leu | Gln | Ser | Asn | Gly | Ser | Tyr |
| 65  |     |     |     |     | 70  |     |     |     |     | 75  |     |     |     |     | 80  |
| Gln | Phe | Asp | Gln | Met | Leu | Leu | Thr | Ala | Gln | Asn | Leu | Pro | Val | Ser | Tyr |
|     |     |     |     | 85  |     |     |     |     | 90  |     |     |     |     | 95  |     |
| Asn | Tyr | Cys | Arg | Leu | Val | Ser | Arg | Ser | Leu | Thr | Val | Arg | Ser | Ser | Thr |
|     |     |     |     | 100 |     |     |     |     | 105 |     |     |     |     | 110 |     |
| Leu | Pro | Gly | Gly | Val | Tyr | Ala | Leu | Asn | Gly | Thr | Ile | Asn | Ala | Val | Thr |
|     |     |     | 115 |     |     |     |     | 120 |     |     |     |     | 125 |     |     |
| Phe | Gln | Gly | Ser | Leu | Ser | Glu | Leu | Thr | Asp | Tyr | Ser | Tyr | Asn | Gly | Leu |
|     |     |     | 130 |     |     |     |     | 135 |     |     |     |     | 140 |     |     |
| Met | Ser | Ala | Thr | Ala | Asn | Ile | Asn | Asp | Lys | Ile | Gly | Asn | Val | Leu | Val |
| 145 |     |     |     |     | 150 |     |     |     |     | 155 |     |     |     |     | 160 |
| Gly | Glu | Gly | Val | Thr | Val | Leu | Ser | Leu | Pro | Thr | Ser | Tyr | Asp | Leu | Ser |
|     |     |     |     | 165 |     |     |     |     | 170 |     |     |     |     | 175 |     |

```
Tyr  Val  Arg  Leu  Gly  Asp  Pro  Ile  Pro  Ala  Ala  Gly  Leu  Asp  Pro  Lys
               180                 185                      190

Leu  Met  Ala  Thr  Cys  Asp  Ser  Ser  Asp  Arg  Pro  Arg  Val  Tyr  Thr  Val
               195                 200                      205

Thr  Ala  Ala  Asp  Glu  Tyr  Gln  Phe  Ser  Ser  Gln  Leu  Ile  Pro  Ser  Gly
     210                      215                      220

Val  Lys  Thr  Thr  Leu  Phe  Thr  Ala  Asn  Ile  Asp  Ala  Leu  Thr  Ser  Leu
225                      230                 235                           240

Ser  Val  Gly  Gly  Glu  Leu  Ile  Phe  Ser  Gln  Val  Thr  Ile  His  Ser  Ile
               245                      250                           255

Glu  Val  Asp  Val  Thr  Ile  Tyr  Phe  Ile  Gly  Phe  Asp  Gly  Thr  Glu  Val
               260                      265                 270

Thr  Val  Lys  Ala  Val  Ala  Thr  Asp  Phe  Gly  Leu  Thr  Thr  Gly  Thr  Asn
          275                      280                      285

Asn  Leu  Val  Pro  Phe  Asn  Leu  Gly  Gly  Pro  Thr  Ser  Glu  Ile  Thr  Gln
     290                      295                 300

Pro  Ile  Thr  Ser  Met  Lys  Leu  Glu  Val  Val  Thr  Tyr  Lys  Arg  Gly  Gly
305                      310                      315                      320

Thr  Ala  Gly  Asp  Pro  Ile  Ser  Trp  Thr  Val  Ser  Gly  Thr  Leu  Ala  Val
               325                 330                      335

Thr  Ile  Val  Gly  Gly  Asn  Tyr  Pro  Gly  Ala  Leu  Arg  Pro  Val  Thr  Leu
               340                 345                      350

Val  Ala  Tyr  Glu  Arg  Val  Ala  Ala  Gly  Ser  Val  Val  Thr  Val  Ala  Gly
          355                      360                      365

Val  Ser  Asn  Phe  Glu  Leu  Ile  Pro  Asn  Pro  Glu  Leu  Ala  Lys  Asn  Leu
     370                      375                      380

Val  Thr  Glu  Tyr  Gly  Arg  Phe  Asp  Pro  Gly  Ala  Met  Asn  Tyr  Thr  Lys
385                      390                      395                      400

Leu  Ile  Leu  Ser  Glu  Arg  Asp  Arg  Leu  Gly  Ile  Lys  Thr  Val  Trp  Pro
               405                      410                      415

Thr  Arg  Glu  Tyr  Thr  Asp  Phe  Arg  Glu  Tyr  Phe  Met  Glu  Val  Ala  Asp
               420                      425                 430

Leu  Asn  Ser  Pro  Leu  Lys  Ile  Ala  Gly  Ala  Phe  Gly  Phe  Lys  Asp  Ile
               435                      440                 445

Ile  Arg  Ala  Ile  Arg  Lys  Ile  Ala  Val  Pro  Val  Val  Ser  Thr  Leu  Phe
     450                      455                 460

Pro  Pro  Ala  Ala  Pro  Leu  Ala  His  Ala  Asn  Arg  Glu  Gly  Val  Asp  Tyr
465                      470                      475                      480

Leu  Leu  Gly  Asp  Glu  Ala  Gln  Ala  Ala  Ser  Gly  Thr  Ala  Arg  Gly  Ala
               485                      490                      495

Ser  Gly  Lys  Ala  Arg  Ala  Ala  Ser  Gly  Arg  Ile  Arg  Gln  Leu  Thr  Leu
               500                      505                      510

Ala  Ala  Asp  Lys  Gly  Tyr  Glu  Val  Val  Ala  Asn  Met  Phe  Gln  Val  Pro
          515                      520                 525

Gln  Asn  Pro  Ile  Val  Asp  Gly  Ile  Leu  Ala  Ser  Pro  Gly  Ile  Leu  Arg
     530                      535                 540

Gly  Ala  His  Asn  Leu  Asp  Cys  Val  Ser  Lys  Glu  Gly  Ala  Thr  Leu  Phe
545                      550                 555                           560

Pro  Val  Val  Ile  Thr  Thr  Leu  Glu  Asp  Glu  Leu  Thr  Pro  Lys  Ala  Leu
               565                      570                      575

Asn  Ser  Lys  Met  Phe  Ala  Val  Ile  Glu  Gly  Ala  Arg  Glu  Asp  Leu  Gln
               580                      585                      590

Pro  Pro  Ser  Gln  Arg  Gly  Ser  Phe  Ile  Arg  Thr  Leu  Ser  Gly  His  Arg
```

|     |     |     |     |     |     |     |     |     |     |     |     |     |     |     |
|-----|-----|-----|-----|-----|-----|-----|-----|-----|-----|-----|-----|-----|-----|-----|
|     |     | 595 |     |     |     |     | 600 |     |     |     |     | 605 |     |     |
| Val | Tyr | Gly | Tyr | Ala | Pro | Asp | Gly | Val | Leu | Pro | Leu | Glu | Thr | Gly | Arg |
|     |     | 610 |     |     |     | 615 |     |     |     | 620 |     |     |     |     |
| Asp | Tyr | Thr | Val | Val | Pro | Ile | Asp | Asp | Val | Trp | Asp | Asp | Ser | Ile | Met |
| 625 |     |     |     |     | 630 |     |     |     | 635 |     |     |     |     | 640 |
| Leu | Ser | Gln | Asp | Pro | Ile | Pro | Pro | Ile | Val | Gly | Asn | Ser | Gly | Asn | Leu |
|     |     |     |     | 645 |     |     |     |     | 650 |     |     |     |     | 655 |
| Ala | Ile | Ala | Tyr | Met | Asp | Val | Phe | Arg | Pro | Lys | Val | Pro | Ile | His | Val |
|     |     |     | 660 |     |     |     |     | 665 |     |     |     | 670 |     |     |
| Ala | Met | Thr | Gly | Ala | Leu | Asn | Ala | Ser | Glu | Ile | Glu | Ser | Val | Ser | Phe |
|     |     | 675 |     |     |     |     | 680 |     |     |     |     | 685 |     |     |
| Arg | Ser | Thr | Lys | Leu | Ala | Thr | Ala | His | Arg | Leu | Gly | Met | Lys | Leu | Ala |
|     |     | 690 |     |     |     |     | 695 |     |     |     |     | 700 |     |     |
| Gly | Pro | Gly | Asp | Tyr | Asp | Ile | Asn | Thr | Gly | Pro | Asn | Trp | Ala | Thr | Phe |
| 705 |     |     |     |     | 710 |     |     |     |     | 715 |     |     |     |     | 720 |
| Ile | Lys | Arg | Phe | Pro | His | Asn | Pro | Arg | Gly | Trp | Asp | Arg | Leu | Pro | Tyr |
|     |     |     |     | 725 |     |     |     |     | 730 |     |     |     |     | 735 |
| Leu | Asn | Leu | Pro | Tyr | Leu | Pro | Pro | Thr | Ala | Gly | Arg | Gln | Phe | His | Leu |
|     |     |     | 740 |     |     |     |     | 745 |     |     |     |     | 750 |     |
| Ala | Leu | Ala | Ala | Ser | Glu | Phe | Lys | Glu | Thr | Pro | Glu | Leu | Glu | Asp | Ala |
|     |     |     | 755 |     |     |     |     | 760 |     |     |     |     | 765 |     |
| Val | Arg | Ala | Met | Asp | Ala | Ala | Asn | Ala | Asp | Pro | Leu | Phe | Arg | Ser |
|     |     | 770 |     |     |     |     | 775 |     |     |     | 780 |     |     |     |
| Ala | Leu | Gln | Val | Phe | Met | Trp | Leu | Glu | Glu | Asn | Gly | Ile | Val | Thr | Asp |
| 785 |     |     |     |     | 790 |     |     |     |     | 795 |     |     |     |     | 800 |
| Met | Ala | Asn | Phe | Ala | Leu | Ser | Asp | Pro | Asn | Ala | His | Arg | Met | Lys | Asn |
|     |     |     |     | 805 |     |     |     |     | 810 |     |     |     |     | 815 |
| Phe | Leu | Ala | Asn | Ala | Pro | Gln | Ala | Gly | Ser | Lys | Ser | Gln | Arg | Ala | Lys |
|     |     |     | 820 |     |     |     |     | 825 |     |     |     |     | 830 |     |
| Tyr | Gly | Thr | Ala | Gly | Tyr | Gly | Val | Glu | Ala | Arg | Gly | Pro | Thr | Pro | Glu |
|     |     | 835 |     |     |     |     | 840 |     |     |     |     | 845 |     |     |
| Glu | Ala | Gln | Arg | Ala | Lys | Asp | Ala | Arg | Ile | Ser | Lys | Lys | Met | Glu | Thr |
|     | 850 |     |     |     |     | 855 |     |     |     |     | 860 |     |     |     |
| Met | Gly | Ile | Tyr | Phe | Ala | Thr | Pro | Glu | Trp | Val | Ala | Leu | Asn | Gly | His |
| 865 |     |     |     |     | 870 |     |     |     |     | 875 |     |     |     |     | 880 |
| Arg | Gly | Pro | Ser | Pro | Gly | Gln | Leu | Lys | Tyr | Trp | Gln | Asn | Thr | Arg | Glu |
|     |     |     |     | 885 |     |     |     |     | 890 |     |     |     |     | 895 |
| Ile | Pro | Glu | Pro | Asn | Glu | Asp | Tyr | Pro | Asp | Tyr | Val | His | Ala | Glu | Lys |
|     |     |     | 900 |     |     |     |     | 905 |     |     |     |     | 910 |     |
| Ser | Arg | Leu | Ala | Ser | Glu | Glu | Gln | Ile | Leu | Arg | Ala | Ala | Thr | Ser | Ile |
|     |     | 915 |     |     |     |     | 920 |     |     |     |     | 925 |     |     |
| Tyr | Gly | Ala | Pro | Gly | Gln | Ala | Glu | Pro | Pro | Gln | Ala | Phe | Ile | Asp | Glu |
|     |     | 930 |     |     |     |     | 935 |     |     |     |     | 940 |     |     |
| Val | Ala | Arg | Val | Tyr | Glu | Thr | Asn | His | Gly | Arg | Val | Pro | Asn | Gln | Glu |
| 945 |     |     |     |     | 950 |     |     |     |     | 955 |     |     |     |     | 960 |
| Gln | Met | Lys | Asp | Leu | Leu | Leu | Thr | Ala | Met | Glu | Met | Lys | His | Arg | Asn |
|     |     |     |     | 965 |     |     |     |     | 970 |     |     |     |     | 975 |
| Pro | Arg | Arg | Ala | Pro | Pro | Lys | Pro | Lys | Pro | Lys | Pro | Asn | Ala | Pro | Ser |
|     |     |     | 980 |     |     |     |     | 985 |     |     |     |     | 990 |     |
| Gln | Arg | Pro | Pro | Gly | Arg | Leu | Gly | Arg | Trp | Ile | Arg | Thr | Val | Ser | Asp |
|     |     |     | 995 |     |     |     |     | 1000|     |     |     |     | 1005|     |
| Glu | Asp | Leu | Glu |     |     |     |     |     |     |     |     |     |     |     |
|     |     | 1010|     |     |     |     |     |     |     |     |     |     |     |     |

( 2 ) INFORMATION FOR SEQ ID NO:11:

( i ) SEQUENCE CHARACTERISTICS:
        ( A ) LENGTH: 3230 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 114..3149

( x i ) SEQUENCE DESCRIPTION: SEQ ID NO:11:

```
CCCCGGGGGA GTCACCCGGG GACAGGCCGT CAAGGCCTTG TTCCAGGATG GAACTCCCCC              60

TTCTACAATG CTATCATTGA TGGTTAGTAG AGATCGGACA AACGATCGCA GCG ATG              116
                                                          Met
                                                           1

ACA AAC CTG CAA GAT CAA ACC CAA CAG ATT GTT CCG TTC ATA CGG AGC             164
Thr Asn Leu Gln Asp Gln Thr Gln Gln Ile Val Pro Phe Ile Arg Ser
          5                  10                  15

CTT CTG ATG CCA ACA ACC GGA CCG GCG TCC ATT CCG GAC GAC ACC CTG             212
Leu Leu Met Pro Thr Thr Gly Pro Ala Ser Ile Pro Asp Asp Thr Leu
         20                  25                  30

GAG AAG CAC ACT CTC AGG TCA GAG ACC TCG ACC TAC AAT TTG ACT GTG             260
Glu Lys His Thr Leu Arg Ser Glu Thr Ser Thr Tyr Asn Leu Thr Val
     35                  40                  45

GGG GAC ACA GGG TCA GGG CTA ATT GTC TTT TTC CCT GGA TTC CCT GGC             308
Gly Asp Thr Gly Ser Gly Leu Ile Val Phe Phe Pro Gly Phe Pro Gly
 50                  55                  60                  65

TCA ATT GTG GGT GCT CAC TAC ACA CTG CAG AGC AAT GGG AAC TAC AAG             356
Ser Ile Val Gly Ala His Tyr Thr Leu Gln Ser Asn Gly Asn Tyr Lys
                 70                  75                  80

TTC GAT CAG ATG CTC CTG ACT GCC CAG AAC CTA CCG GCC AGC TAC AAC             404
Phe Asp Gln Met Leu Leu Thr Ala Gln Asn Leu Pro Ala Ser Tyr Asn
             85                  90                  95

TAC TGC AGG CTA GTG AGT CGG AGT CTC ACA GTA AGG TCA AGC ACA CTC             452
Tyr Cys Arg Leu Val Ser Arg Ser Leu Thr Val Arg Ser Ser Thr Leu
        100                 105                 110

CCT GGT GGC GTT TAT GCA CTA AAC GGC ACC ATA AAC GCC GTG ACC TTC             500
Pro Gly Gly Val Tyr Ala Leu Asn Gly Thr Ile Asn Ala Val Thr Phe
    115                 120                 125

CAA GGA AGC CTG AGT GAA CTG ACA GAT GTT AGC TAC AAT GGG TTG ATG             548
Gln Gly Ser Leu Ser Glu Leu Thr Asp Val Ser Tyr Asn Gly Leu Met
130                 135                 140                 145

TCT GCA ACA GCC AAC ATC AAC GAC AAA ATT GGG AAC GTC CTA GTA GGG             596
Ser Ala Thr Ala Asn Ile Asn Asp Lys Ile Gly Asn Val Leu Val Gly
                150                 155                 160

GAA GGG GTT ACT GTC CTC AGC TTA CCC ACA TCA TAT GAT CTT GGG TAT             644
Glu Gly Val Thr Val Leu Ser Leu Pro Thr Ser Tyr Asp Leu Gly Tyr
            165                 170                 175

GTG AGG CTT GGT GAC CCC ATA CCC GCT ATA GGG CTT GAC CCA AAA ATG             692
Val Arg Leu Gly Asp Pro Ile Pro Ala Ile Gly Leu Asp Pro Lys Met
        180                 185                 190

GTA GCA ACA TGT GAC AGC AGT GAC AGG CCC AGA GTC TAC ACC ATA ACT             740
Val Ala Thr Cys Asp Ser Ser Asp Arg Pro Arg Val Tyr Thr Ile Thr
    195                 200                 205

GCA GCT GAT GAT TAC CAA TTC TCA TCA CAG TAC CAA ACA GGT GGG GTA             788
Ala Ala Asp Asp Tyr Gln Phe Ser Ser Gln Tyr Gln Thr Gly Gly Val
210                 215                 220                 225

ACA ATC ACC CTG TTC TCA GCC AAC ATT GAT GCC ATC ACA AGC CTC AGC             836
```

```
Thr Ile Thr Leu Phe Ser Ala Asn Ile Asp Ala Ile Thr Ser Leu Ser
            230                 235                 240

GTT GGG GGA GAG CTC GTG TTT AAA ACA AGC GTC CAC AGC CTT GTA CTG      884
Val Gly Gly Glu Leu Val Phe Lys Thr Ser Val His Ser Leu Val Leu
            245                 250                 255

GGC GCC ACC ATC TAC CTT ATA GGC TTT GAT GGG TCT GCG GTA ATC ACT      932
Gly Ala Thr Ile Tyr Leu Ile Gly Phe Asp Gly Ser Ala Val Ile Thr
            260                 265                 270

AGA GCT GTG GCC GCA AAC AAT GGG CTG ACG ACC GGC ACC GAC AAT CTT      980
Arg Ala Val Ala Ala Asn Asn Gly Leu Thr Thr Gly Thr Asp Asn Leu
    275                 280                 285

ATG CCA TTC AAT CTT GTG ATT CCA ACC AAC GAG ATA ACC CAG CCA ATC     1028
Met Pro Phe Asn Leu Val Ile Pro Thr Asn Glu Ile Thr Gln Pro Ile
290                 295                 300                 305

ACA TCC ATC AAA CTG GAG ATA GTG ACC TCC AAA AGT GGT GGT CAG GAA     1076
Thr Ser Ile Lys Leu Glu Ile Val Thr Ser Lys Ser Gly Gly Gln Glu
                310                 315                 320

GGG GAC CAG ATG TCA TGG TCG GCA AGT GGG AGC CTA GCA GTG ACG ATT     1124
Gly Asp Gln Met Ser Trp Ser Ala Ser Gly Ser Leu Ala Val Thr Ile
                325                 330                 335

CAT GGT GGC AAC TAT CCA GGG GCC CTC CGT CCC GTC ACA CTA GTA GCC     1172
His Gly Gly Asn Tyr Pro Gly Ala Leu Arg Pro Val Thr Leu Val Ala
            340                 345                 350

TAC GAA AGA GTG GCA ACA GGA TCT GTC GTT ACG GTC GCT GGG GTG AGC     1220
Tyr Glu Arg Val Ala Thr Gly Ser Val Val Thr Val Ala Gly Val Ser
            355                 360                 365

AAC TTC GAG CTG ATC CCA AAT CCT GAA CTA GCA AAG AAC CTG GTT ACA     1268
Asn Phe Glu Leu Ile Pro Asn Pro Glu Leu Ala Lys Asn Leu Val Thr
370                 375                 380                 385

GAA TAC GGC CGA TTT GAC CCA GGA GCC ATG AAC TAC ACA AAA TTG ATA     1316
Glu Tyr Gly Arg Phe Asp Pro Gly Ala Met Asn Tyr Thr Lys Leu Ile
                390                 395                 400

CTG AGT GAG AGG GAC CGC CTT GGC ATC AAG ACA GTC TGG CCG ACA AGG     1364
Leu Ser Glu Arg Asp Arg Leu Gly Ile Lys Thr Val Trp Pro Thr Arg
            405                 410                 415

GAG TAC ACC GAC TTT CGT GAG TAC TTC ATG GAG GTG GCC GAC CTC AGC     1412
Glu Tyr Thr Asp Phe Arg Glu Tyr Phe Met Glu Val Ala Asp Leu Ser
            420                 425                 430

TCT CCC CTG AAG ATT GCA GGA GCA TTT GGC TTC AAA GAC ATA ATC CGG     1460
Ser Pro Leu Lys Ile Ala Gly Ala Phe Gly Phe Lys Asp Ile Ile Arg
    435                 440                 445

GCC ATA AGG AGG ATA GCT GTG CCG GTG GTC TCC ACA TTG TTC CCA CCT     1508
Ala Ile Arg Arg Ile Ala Val Pro Val Val Ser Thr Leu Phe Pro Pro
450                 455                 460                 465

GCC GCT CCC CTG GCC CAT GCA ATT GGG GAA GGT GTA GAC TAC CTG CTG     1556
Ala Ala Pro Leu Ala His Ala Ile Gly Glu Gly Val Asp Tyr Leu Leu
                470                 475                 480

GGT GAT GAG GCA CAG GCT GCT TCA GGA ACT GCT CGA GCC GCG TCA GGA     1604
Gly Asp Glu Ala Gln Ala Ala Ser Gly Thr Ala Arg Ala Ala Ser Gly
            485                 490                 495

AAA GCA AGG GCT GCC TCA GGC CGC ATA AGG CAG CTG ACT CTC GCC GCC     1652
Lys Ala Arg Ala Ala Ser Gly Arg Ile Arg Gln Leu Thr Leu Ala Ala
    500                 505                 510

GAC AAG GGG TAC GAG GTA GTC GCG AAT CTA TTC CAG GTG CCC CAG AAT     1700
Asp Lys Gly Tyr Glu Val Val Ala Asn Leu Phe Gln Val Pro Gln Asn
515                 520                 525

CCC GTA GTC GAC GGG ATT CTT GCT TCA CCC GGG ATA CTC CGC GGT GCA     1748
Pro Val Val Asp Gly Ile Leu Ala Ser Pro Gly Ile Leu Arg Gly Ala
530                 535                 540                 545

CAC AAC CTC GAC TGC GTG TTA AGA GAG GGC GCC ACG CTA TTC CCT GTG     1796
```

| | | | | | | | | | | | | | | | | |
|---|---|---|---|---|---|---|---|---|---|---|---|---|---|---|---|---|
| His | Asn | Leu | Asp | Cys | Val | Leu | Arg | Glu | Gly | Ala | Thr | Leu | Phe | Pro | Val | |
| | | | | 550 | | | | 555 | | | | | | 560 | | |
| GTC | ATC | ACG | ACA | GTG | GAA | GAC | GCC | ATG | ACA | CCC | AAA | GCA | CTA | AAC | AGC | 1844 |
| Val | Ile | Thr | Thr | Val | Glu | Asp | Ala | Met | Thr | Pro | Lys | Ala | Leu | Asn | Ser | |
| | | | 565 | | | | | 570 | | | | | 575 | | | |
| AAA | ATG | TTT | GCT | GTC | ATT | GAA | GGC | GTG | CGA | GAG | GAC | CTC | CAA | CCT | CCA | 1892 |
| Lys | Met | Phe | Ala | Val | Ile | Glu | Gly | Val | Arg | Glu | Asp | Leu | Gln | Pro | Pro | |
| | | 580 | | | | | 585 | | | | | 590 | | | | |
| TCT | CAA | AGA | GGA | TCC | TTC | ATA | CGA | ACT | CTC | TCC | GGA | CAC | AGA | GTC | TAT | 1940 |
| Ser | Gln | Arg | Gly | Ser | Phe | Ile | Arg | Thr | Leu | Ser | Gly | His | Arg | Val | Tyr | |
| | 595 | | | | | 600 | | | | | 605 | | | | | |
| GGA | TAT | GCT | CCA | GAT | GGG | GTA | CTT | CCA | CTG | GAG | ACT | GGG | AGA | GAC | TAC | 1988 |
| Gly | Tyr | Ala | Pro | Asp | Gly | Val | Leu | Pro | Leu | Glu | Thr | Gly | Arg | Asp | Tyr | |
| 610 | | | | | 615 | | | | | 620 | | | | | 625 | |
| ACC | GTT | GTC | CCA | ATA | GAT | GAT | GTC | TGG | GAC | GAC | AGC | ATT | ATG | CTG | TCC | 2036 |
| Thr | Val | Val | Pro | Ile | Asp | Asp | Val | Trp | Asp | Asp | Ser | Ile | Met | Leu | Ser | |
| | | | | 630 | | | | 635 | | | | | 640 | | | |
| AAA | GAC | CCC | ATA | CCT | CCT | ATT | GTG | GGA | AAC | AGT | GGA | AAC | CTA | GCC | ATA | 2084 |
| Lys | Asp | Pro | Ile | Pro | Pro | Ile | Val | Gly | Asn | Ser | Gly | Asn | Leu | Ala | Ile | |
| | | | 645 | | | | | 650 | | | | | 655 | | | |
| GCT | TAC | ATG | GAT | GTG | TTT | CGA | CCC | AAA | GTC | CCC | ATC | CAT | GTG | GCC | ATG | 2132 |
| Ala | Tyr | Met | Asp | Val | Phe | Arg | Pro | Lys | Val | Pro | Ile | His | Val | Ala | Met | |
| | | 660 | | | | | 665 | | | | | 670 | | | | |
| ACG | GGA | GCC | CTC | AAC | GCT | TGT | GGC | GAG | ATT | GAG | AAA | ATA | AGC | TTT | AGA | 2180 |
| Thr | Gly | Ala | Leu | Asn | Ala | Cys | Gly | Glu | Ile | Glu | Lys | Ile | Ser | Phe | Arg | |
| | 675 | | | | | 680 | | | | | 685 | | | | | |
| AGC | ACC | AAG | CTC | GCC | ACC | GCA | CAC | CGG | CTT | GGC | CTC | AAG | TTG | GCT | GGT | 2228 |
| Ser | Thr | Lys | Leu | Ala | Thr | Ala | His | Arg | Leu | Gly | Leu | Lys | Leu | Ala | Gly | |
| 690 | | | | | 695 | | | | | 700 | | | | | 705 | |
| CCC | GGA | GCA | TTT | GAT | GTA | AAC | ACC | GGG | CCC | AAC | TGG | GCA | ACG | TTC | ATC | 2276 |
| Pro | Gly | Ala | Phe | Asp | Val | Asn | Thr | Gly | Pro | Asn | Trp | Ala | Thr | Phe | Ile | |
| | | | | 710 | | | | 715 | | | | | 720 | | | |
| AAA | CGT | TTC | CCT | CAC | AAT | CCA | CGC | GAC | TGG | GAC | AGG | CTC | CCC | TAC | CTC | 2324 |
| Lys | Arg | Phe | Pro | His | Asn | Pro | Arg | Asp | Trp | Asp | Arg | Leu | Pro | Tyr | Leu | |
| | | | 725 | | | | | 730 | | | | | 735 | | | |
| AAC | CTT | CCA | TAC | CTT | CCA | CCC | AAT | GCA | GGA | CGC | CAG | TAC | CAC | CTC | GCC | 2372 |
| Asn | Leu | Pro | Tyr | Leu | Pro | Pro | Asn | Ala | Gly | Arg | Gln | Tyr | His | Leu | Ala | |
| | | 740 | | | | | 745 | | | | | 750 | | | | |
| ATG | GCC | GCA | TCA | GAG | TTC | AAG | GAG | ACC | CCT | GAA | CTC | GAG | AGC | GCC | GTC | 2420 |
| Met | Ala | Ala | Ser | Glu | Phe | Lys | Glu | Thr | Pro | Glu | Leu | Glu | Ser | Ala | Val | |
| | 755 | | | | | 760 | | | | | 765 | | | | | |
| AGG | GCC | ATG | GAA | GCA | GCA | GCC | AGT | GTA | GAC | CCA | CTG | TTC | CAA | TCT | GCA | 2468 |
| Arg | Ala | Met | Glu | Ala | Ala | Ala | Ser | Val | Asp | Pro | Leu | Phe | Gln | Ser | Ala | |
| 770 | | | | | 775 | | | | | 780 | | | | | 785 | |
| CTC | AGT | GTG | TTC | ATG | TGG | CTG | GAA | GAG | AAT | GGG | ATT | GTG | ACT | GAC | ATG | 2516 |
| Leu | Ser | Val | Phe | Met | Trp | Leu | Glu | Glu | Asn | Gly | Ile | Val | Thr | Asp | Met | |
| | | | | 790 | | | | 795 | | | | | 800 | | | |
| GCC | AAC | TTC | GCA | CTC | AGC | GAC | CCG | AAC | GCC | CAT | CGG | ATG | CGA | AAC | TTT | 2564 |
| Ala | Asn | Phe | Ala | Leu | Ser | Asp | Pro | Asn | Ala | His | Arg | Met | Arg | Asn | Phe | |
| | | | 805 | | | | | 810 | | | | | 815 | | | |
| CTT | GCA | AAC | GCA | CCA | CAA | GCA | GGT | AGC | AAG | TCT | CAA | AGG | GCC | AAA | TAC | 2612 |
| Leu | Ala | Asn | Ala | Pro | Gln | Ala | Gly | Ser | Lys | Ser | Gln | Arg | Ala | Lys | Tyr | |
| | | 820 | | | | | 825 | | | | | 830 | | | | |
| GGG | ACA | GCA | GGC | TAC | GGA | GTG | GAG | GCC | CGG | GGC | CCC | ACA | CCA | GAA | GAA | 2660 |
| Gly | Thr | Ala | Gly | Tyr | Gly | Val | Glu | Ala | Arg | Gly | Pro | Thr | Pro | Glu | Glu | |
| | 835 | | | | | 840 | | | | | 845 | | | | | |
| GCA | CAG | AGG | GAA | AAA | GAC | ACA | CGG | ATC | TCA | AAG | AAG | ATG | GAG | ACC | ATG | 2708 |
| Ala | Gln | Arg | Glu | Lys | Asp | Thr | Arg | Ile | Ser | Lys | Lys | Met | Glu | Thr | Met | |
| 850 | | | | | 855 | | | | | 860 | | | | | 865 | |
| GGC | ATC | TAC | TTT | GCA | ACA | CCA | GAA | TGG | GTA | GCA | CTC | AAT | GGG | CAC | CGA | 2756 |

-continued

```
       Gly Ile Tyr Phe Ala Thr Pro Glu Trp Val Ala Leu Asn Gly His Arg
                       870                 875                 880

GGG CCA AGC CCC GGC CAG CTA AAG TAC TGG CAG AAC ACA CGA GAA ATA          2804
Gly Pro Ser Pro Gly Gln Leu Lys Tyr Trp Gln Asn Thr Arg Glu Ile
            885                 890                 895

CCG GAC CCA AAC GAG GAC TAT CTA GAC TAC GTG CAT GCA GAG AAG AGC          2852
Pro Asp Pro Asn Glu Asp Tyr Leu Asp Tyr Val His Ala Glu Lys Ser
            900                 905                 910

CGG TTG GCA TCA GAA GAA CAA ATC CTA AGG GCA GCT ACG TCG ATC TAC          2900
Arg Leu Ala Ser Glu Glu Gln Ile Leu Arg Ala Ala Thr Ser Ile Tyr
        915                 920                 925

GGG GCT CCA GGA CAG GCA GAG CCA CCC CAA GCT TTC ATA GAC GAA GTT          2948
Gly Ala Pro Gly Gln Ala Glu Pro Pro Gln Ala Phe Ile Asp Glu Val
930                 935                 940                 945

GCC AAA GTC TAT GAA ATC AAC CAT GGA CGT GGC CCA AAC CAA GAA CAG          2996
Ala Lys Val Tyr Glu Ile Asn His Gly Arg Gly Pro Asn Gln Glu Gln
                950                 955                 960

ATG AAA GAT CTG CTC TTG ACT GCG ATG GAG ATG AAG CAT CGC AAT CCC          3044
Met Lys Asp Leu Leu Leu Thr Ala Met Glu Met Lys His Arg Asn Pro
                965                 970                 975

AGG CGG GCT CCA CCA AAG CCC AAG CCA AGA CCC AAC GCT CCA ACG CAG          3092
Arg Arg Ala Pro Pro Lys Pro Lys Pro Arg Pro Asn Ala Pro Thr Gln
            980                 985                 990

AGA CCC CCT GGT CGG CTG GGC CGC TGG ATC AGG ACT GTC TCT GAT GAG          3140
Arg Pro Pro Gly Arg Leu Gly Arg Trp Ile Arg Thr Val Ser Asp Glu
995                 1000                1005

GAC CTT GAG TGAGGCTCCT GGGAGTCTCC CGACACCACC CGCGCAGGCG                  3189
Asp Leu Glu
1010

TGGACACCAA TTCGGCCTTA CAACATCCCA AATTGGATCC G                            3230
```

( 2 ) INFORMATION FOR SEQ ID NO:12:

( i ) SEQUENCE CHARACTERISTICS:
        ( A ) LENGTH: 1012 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
                20                  25                  30

Leu Glu Lys His Thr Leu Arg Ser Glu Thr Ser Thr Tyr Asn Leu Thr
                35                  40                  45

Val Gly Asp Thr Gly Ser Gly Leu Ile Val Phe Phe Pro Gly Phe Pro
            50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
                100                 105                 110

Leu Pro Gly Gly Val Tyr Ala Leu Asn Gly Thr Ile Asn Ala Val Thr
            115                 120                 125

Phe Gln Gly Ser Leu Ser Glu Leu Thr Asp Val Ser Tyr Asn Gly Leu
130                 135                 140
```

```
Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
            165                 170                 175

Tyr Val Arg Leu Gly Asp Pro Ile Pro Ala Ile Gly Leu Asp Pro Lys
        180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val His Ser Leu Val
            245                 250                 255

Leu Gly Ala Thr Ile Tyr Leu Ile Gly Phe Asp Gly Ser Ala Val Ile
        260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Glu Gly Asp Gln Met Ser Trp Ser Ala Ser Gly Ser Leu Ala Val Thr
            325                 330                 335

Ile His Gly Gly Asn Tyr Pro Gly Ala Leu Arg Pro Val Thr Leu Val
        340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
            405                 410                 415

Arg Glu Tyr Thr Asp Phe Arg Glu Tyr Phe Met Glu Val Ala Asp Leu
        420                 425                 430

Ser Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
            485                 490                 495

Gly Lys Ala Arg Ala Ala Ser Gly Arg Ile Arg Gln Leu Thr Leu Ala
        500                 505                 510

Ala Asp Lys Gly Tyr Glu Val Val Ala Asn Leu Phe Gln Val Pro Gln
        515                 520                 525

Asn Pro Val Val Asp Gly Ile Leu Ala Ser Pro Gly Ile Leu Arg Gly
    530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
            565                 570                 575
```

-continued

| | | | | | | | | | | | | | | |
|---|---|---|---|---|---|---|---|---|---|---|---|---|---|---|
| Ser | Lys | Met | Phe 580 | Ala | Val | Ile | Glu 585 | Val | Arg | Glu | Asp | Leu 590 | Gln | Pro |
| Pro | Ser | Gln 595 | Arg | Gly | Ser | Phe | Ile 600 | Arg | Thr | Leu | Ser | Gly 605 | His | Arg | Val |
| Tyr | Gly 610 | Tyr | Ala | Pro | Asp | Gly 615 | Val | Leu | Pro | Leu | Glu 620 | Thr | Gly | Arg | Asp |
| Tyr 625 | Thr | Val | Val | Pro | Ile 630 | Asp | Asp | Val | Trp | Asp 635 | Asp | Ser | Ile | Met | Leu 640 |
| Ser | Lys | Asp | Pro | Ile 645 | Pro | Pro | Ile | Val | Gly 650 | Asn | Ser | Gly | Asn | Leu 655 | Ala |
| Ile | Ala | Tyr | Met 660 | Asp | Val | Phe | Arg | Pro 665 | Lys | Val | Pro | Ile 670 | His | Val | Ala |
| Met | Thr | Gly 675 | Ala | Leu | Asn | Ala | Cys 680 | Gly | Glu | Ile | Glu | Lys 685 | Ile | Ser | Phe |
| Arg | Ser 690 | Thr | Lys | Leu | Ala | Thr 695 | Ala | His | Arg | Leu | Gly 700 | Leu | Lys | Leu | Ala |
| Gly 705 | Pro | Gly | Ala | Phe | Asp 710 | Val | Asn | Thr | Gly | Pro 715 | Asn | Trp | Ala | Thr | Phe 720 |
| Ile | Lys | Arg | Phe | Pro 725 | His | Asn | Pro | Arg | Asp 730 | Trp | Asp | Arg | Leu | Pro 735 | Tyr |
| Leu | Asn | Leu | Pro 740 | Tyr | Leu | Pro | Pro | Asn 745 | Ala | Gly | Arg | Gln | Tyr 750 | His | Leu |
| Ala | Met | Ala 755 | Ala | Ser | Glu | Phe | Lys 760 | Glu | Thr | Pro | Glu | Leu 765 | Glu | Ser | Ala |
| Val | Arg 770 | Ala | Met | Glu | Ala | Ala 775 | Ala | Ser | Val | Asp | Pro 780 | Leu | Phe | Gln | Ser |
| Ala 785 | Leu | Ser | Val | Phe | Met 790 | Trp | Leu | Glu | Glu | Asn 795 | Gly | Ile | Val | Thr | Asp 800 |
| Met | Ala | Asn | Phe | Ala 805 | Leu | Ser | Asp | Pro | Asn 810 | Ala | His | Arg | Met | Arg 815 | Asn |
| Phe | Leu | Ala | Asn 820 | Ala | Pro | Gln | Ala | Gly 825 | Ser | Lys | Ser | Gln | Arg 830 | Ala | Lys |
| Tyr | Gly | Thr 835 | Ala | Gly | Tyr | Gly | Val 840 | Glu | Ala | Arg | Gly | Pro 845 | Thr | Pro | Glu |
| Glu | Ala 850 | Gln | Arg | Glu | Lys | Asp 855 | Thr | Arg | Ile | Ser | Lys 860 | Lys | Met | Glu | Thr |
| Met 865 | Gly | Ile | Tyr | Phe | Ala 870 | Thr | Pro | Glu | Trp | Val 875 | Ala | Leu | Asn | Gly | His 880 |
| Arg | Gly | Pro | Ser | Pro 885 | Gly | Gln | Leu | Lys | Tyr 890 | Trp | Gln | Asn | Thr | Arg 895 | Glu |
| Ile | Pro | Asp | Pro 900 | Asn | Glu | Asp | Tyr | Leu 905 | Asp | Tyr | Val | His | Ala 910 | Glu | Lys |
| Ser | Arg | Leu 915 | Ala | Ser | Glu | Glu | Gln 920 | Ile | Leu | Arg | Ala | Ala 925 | Thr | Ser | Ile |
| Tyr | Gly 930 | Ala | Pro | Gly | Gln | Ala 935 | Glu | Pro | Pro | Gln | Ala 940 | Phe | Ile | Asp | Glu |
| Val 945 | Ala | Lys | Val | Tyr | Glu 950 | Ile | Asn | His | Gly | Arg 955 | Gly | Pro | Asn | Gln | Glu 960 |
| Gln | Met | Lys | Asp | Leu 965 | Leu | Leu | Thr | Ala | Met 970 | Glu | Met | Lys | His | Arg 975 | Asn |
| Pro | Arg | Arg | Ala 980 | Pro | Pro | Lys | Pro | Lys 985 | Pro | Arg | Pro | Asn | Ala 990 | Pro | Thr |
| Gln | Arg | Pro | Pro | Gly | Arg | Leu | Gly | Arg | Trp | Ile | Arg | Thr | Val | Ser | Asp |

```
                    995                      1000                     1005
Glu  Asp  Leu  Glu
          1010

( 2 ) INFORMATION FOR SEQ ID NO:13:

( i ) SEQUENCE CHARACTERISTICS:
        ( A ) LENGTH: 3180 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 64..3099

( x i ) SEQUENCE DESCRIPTION: SEQ ID NO:13:

GAATTCCTCC  TTCTACAACG  CTATCATTGA  TGGTTAGTAG  AGATCAGACA  AACGATCGCA              60

GCG  ATG  ACA  AAC  CTG  CAA  GAT  CAA  ACC  CAC  CAG  ATT  GTT  CCG  TTC  ATA     108
     Met  Thr  Asn  Leu  Gln  Asp  Gln  Thr  His  Gln  Ile  Val  Pro  Phe  Ile
          1015                     1020                     1025

CGG  AGC  CTT  CTG  ATG  CCA  ACA  ACC  GGA  CCG  GCG  TCC  ATT  CCG  GAC  GAC     156
Arg  Ser  Leu  Leu  Met  Pro  Thr  Thr  Gly  Pro  Ala  Ser  Ile  Pro  Asp  Asp
          1030                     1035                     1040

ACC  CTG  GAG  AAG  CAC  ACT  CTC  AGG  TCA  GAG  ACC  TCG  ACC  TAC  AAT  TTG     204
Thr  Leu  Glu  Lys  His  Thr  Leu  Arg  Ser  Glu  Thr  Ser  Thr  Tyr  Asn  Leu
          1045                     1050                     1055

ACT  GTG  GGG  GAC  ACA  GGG  TCA  GGG  CTA  ATT  GTC  TTT  TTC  CCT  GGA  TTC     252
Thr  Val  Gly  Asp  Thr  Gly  Ser  Gly  Leu  Ile  Val  Phe  Phe  Pro  Gly  Phe
1060                     1065                     1070                     1075

CCT  GGC  TCA  ATT  GTG  GGT  GCT  CAC  TAC  ACA  CTG  CAG  AGC  AGT  GGG  AAC     300
Pro  Gly  Ser  Ile  Val  Gly  Ala  His  Tyr  Thr  Leu  Gln  Ser  Ser  Gly  Asn
                         1080                     1085                     1090

TAC  AAG  TTC  GAT  CAG  ATG  CTC  CTG  ACT  GCC  CAG  AAC  CTA  CCG  GCC  AGC     348
Tyr  Lys  Phe  Asp  Gln  Met  Leu  Leu  Thr  Ala  Gln  Asn  Leu  Pro  Ala  Ser
               1095                     1100                     1105

TAC  AAC  TAC  TGC  AGG  CTA  GTG  AGT  CGG  AGT  CTC  ACA  GTA  AGG  TCA  AGC     396
Tyr  Asn  Tyr  Cys  Arg  Leu  Val  Ser  Arg  Ser  Leu  Thr  Val  Arg  Ser  Ser
     1110                     1115                     1120

ACA  CTC  CCT  GGT  GGC  GTT  TAT  GCA  CTA  AAC  GGC  ACC  ATA  AAC  GCC  GTG     444
Thr  Leu  Pro  Gly  Gly  Val  Tyr  Ala  Leu  Asn  Gly  Thr  Ile  Asn  Ala  Val
     1125                     1130                     1135

ACC  TTC  CAA  GGA  AGC  CTG  AGT  GAA  CTG  ACA  GAT  GTT  AGC  TAC  AAC  GGG     492
Thr  Phe  Gln  Gly  Ser  Leu  Ser  Glu  Leu  Thr  Asp  Val  Ser  Tyr  Asn  Gly
1140                     1145                     1150                     1155

TTG  ATG  TCT  GCA  ACA  GCC  AAC  ATC  AAC  GAC  AAA  ATT  GGG  AAC  GTC  CTA     540
Leu  Met  Ser  Ala  Thr  Ala  Asn  Ile  Asn  Asp  Lys  Ile  Gly  Asn  Val  Leu
                         1160                     1165                     1170

GTA  GGG  GAA  GGG  GTA  ACC  GTC  CTC  AGC  TTA  CCC  ACA  TCA  TAT  GAT  CTT     588
Val  Gly  Glu  Gly  Val  Thr  Val  Leu  Ser  Leu  Pro  Thr  Ser  Tyr  Asp  Leu
               1175                     1180                     1185

GGG  TAT  GTG  AGG  CTT  GGT  GAC  CCC  ATA  CCC  GCT  ATA  GGG  CTT  GAC  CCA     636
Gly  Tyr  Val  Arg  Leu  Gly  Asp  Pro  Ile  Pro  Ala  Ile  Gly  Leu  Asp  Pro
     1190                     1195                     1200

AAA  ATG  GTA  GCA  ACA  TGT  GAC  AGC  AGT  GAC  AGG  CCC  AGA  GTC  TAC  ACC     684
Lys  Met  Val  Ala  Thr  Cys  Asp  Ser  Ser  Asp  Arg  Pro  Arg  Val  Tyr  Thr
     1205                     1210                     1215

ATA  ACT  GCA  GCC  GAT  AAT  TAC  CAA  TTC  TCA  TCA  CAG  TAC  CAA  ACA  GGT     732
Ile  Thr  Ala  Ala  Asp  Asn  Tyr  Gln  Phe  Ser  Ser  Gln  Tyr  Gln  Thr  Gly
1220                     1225                     1230                     1235
```

| | | | | | | | | | | | | | | | | |
|---|---|---|---|---|---|---|---|---|---|---|---|---|---|---|---|---|
| GGG | GTA | ACA | ATC | ACA | CTG | TTC | TCA | GCC | AAC | ATT | GAT | GCC | ATC | ACA | AGT | 780 |
| Gly | Val | Thr | Ile | Thr | Leu | Phe | Ser | Ala | Asn | Ile | Asp | Ala | Ile | Thr | Ser | |
| | | | 1240 | | | | 1245 | | | | | 1250 | | | | |
| CTC | AGC | GTT | GGG | GGA | GAG | CTC | GTG | TTC | AAA | ACA | AGC | GTC | CAA | AGC | CTT | 828 |
| Leu | Ser | Val | Gly | Gly | Glu | Leu | Val | Phe | Lys | Thr | Ser | Val | Gln | Ser | Leu | |
| | | | 1255 | | | | 1260 | | | | | 1265 | | | | |
| GTA | CTG | GGC | GCC | ACC | ATC | TAC | CTT | ATA | GGC | TTT | GAT | GGG | ACT | GCG | GTA | 876 |
| Val | Leu | Gly | Ala | Thr | Ile | Tyr | Leu | Ile | Gly | Phe | Asp | Gly | Thr | Ala | Val | |
| | | | 1270 | | | | 1275 | | | | | 1280 | | | | |
| ATC | ACC | AGA | GCT | GTG | GCC | GCA | AAC | AAT | GGG | CTG | ACG | GCC | GGC | ATC | GAC | 924 |
| Ile | Thr | Arg | Ala | Val | Ala | Ala | Asn | Asn | Gly | Leu | Thr | Ala | Gly | Ile | Asp | |
| | | | 1285 | | | | 1290 | | | | | 1295 | | | | |
| AAT | CTT | ATG | CCA | TTC | AAT | CTT | GTG | ATT | CCA | ACC | AAT | GAG | ATA | ACC | CAG | 972 |
| Asn | Leu | Met | Pro | Phe | Asn | Leu | Val | Ile | Pro | Thr | Asn | Glu | Ile | Thr | Gln | |
| 1300 | | | | | 1305 | | | | | 1310 | | | | | 1315 | |
| CCA | ATC | ACA | TCC | ATC | ATA | CTG | GAG | ATA | GTG | ACC | TCC | AAA | AGT | GAT | GGT | 1020 |
| Pro | Ile | Thr | Ser | Ile | Ile | Leu | Glu | Ile | Val | Thr | Ser | Lys | Ser | Asp | Gly | |
| | | | 1320 | | | | 1325 | | | | | 1330 | | | | |
| CAG | GCA | GGG | GAA | CAG | ATG | TCA | TGG | TCG | GCA | AGT | GGG | AGC | CTA | GCA | GTG | 1068 |
| Gln | Ala | Gly | Glu | Gln | Met | Ser | Trp | Ser | Ala | Ser | Gly | Ser | Leu | Ala | Val | |
| | | | 1335 | | | | 1340 | | | | | 1345 | | | | |
| ACG | ATC | CAT | GGT | GGC | AAC | TAT | CCA | GGA | GCC | CTC | CGT | CCC | GTC | ACA | CTA | 1116 |
| Thr | Ile | His | Gly | Gly | Asn | Tyr | Pro | Gly | Ala | Leu | Arg | Pro | Val | Thr | Leu | |
| | | | 1350 | | | | 1355 | | | | | 1360 | | | | |
| GTG | GCC | TAC | GAA | AGA | GTG | GCA | ACA | GGA | TCT | GTC | GTT | ACG | GTC | GCT | GGG | 1164 |
| Val | Ala | Tyr | Glu | Arg | Val | Ala | Thr | Gly | Ser | Val | Val | Thr | Val | Ala | Gly | |
| | | | 1365 | | | | 1370 | | | | | 1375 | | | | |
| GTG | AGC | AAC | TTC | GAG | CTG | ATC | CCA | AAT | CCT | GAA | CTA | GCA | AAG | AAC | CTG | 1212 |
| Val | Ser | Asn | Phe | Glu | Leu | Ile | Pro | Asn | Pro | Glu | Leu | Ala | Lys | Asn | Leu | |
| 1380 | | | | | 1385 | | | | | 1390 | | | | | 1395 | |
| GTT | ACA | GAA | TAC | GGC | CGA | TTT | GAC | CCA | GGA | GCC | ATG | AAC | TAC | ACG | AAA | 1260 |
| Val | Thr | Glu | Tyr | Gly | Arg | Phe | Asp | Pro | Gly | Ala | Met | Asn | Tyr | Thr | Lys | |
| | | | 1400 | | | | 1405 | | | | | 1410 | | | | |
| TTG | ATA | CTG | AGT | GAG | AGG | GAC | CAC | CTT | GGC | ATC | AAG | ACC | GTC | TGG | CCA | 1308 |
| Leu | Ile | Leu | Ser | Glu | Arg | Asp | His | Leu | Gly | Ile | Lys | Thr | Val | Trp | Pro | |
| | | | 1415 | | | | 1420 | | | | | 1425 | | | | |
| ACA | AGG | GAG | TAC | ACT | GAC | TTT | CGT | GAG | TAC | TTC | ATG | GAG | GTG | GCC | GAC | 1356 |
| Thr | Arg | Glu | Tyr | Thr | Asp | Phe | Arg | Glu | Tyr | Phe | Met | Glu | Val | Ala | Asp | |
| | | | 1430 | | | | 1435 | | | | | 1440 | | | | |
| CTC | AAC | TCT | CCC | CTG | AAG | ATT | GCA | GGA | GCA | TTT | GGC | TTC | AAA | GAC | ATA | 1404 |
| Leu | Asn | Ser | Pro | Leu | Lys | Ile | Ala | Gly | Ala | Phe | Gly | Phe | Lys | Asp | Ile | |
| | | | 1445 | | | | 1450 | | | | | 1455 | | | | |
| ATC | CGG | GCC | ATA | AGG | AGG | ATA | GCT | GTA | CCG | GTG | GTC | TCT | ACA | TTG | TTC | 1452 |
| Ile | Arg | Ala | Ile | Arg | Arg | Ile | Ala | Val | Pro | Val | Val | Ser | Thr | Leu | Phe | |
| 1460 | | | | | 1465 | | | | | 1470 | | | | | 1475 | |
| CCA | CCT | GCC | GCT | CCT | CTA | GCC | CAT | GCA | ATT | GGG | GAA | GGT | GTA | GAC | TAC | 1500 |
| Pro | Pro | Ala | Ala | Pro | Leu | Ala | His | Ala | Ile | Gly | Glu | Gly | Val | Asp | Tyr | |
| | | | 1480 | | | | 1485 | | | | | 1490 | | | | |
| CTA | CTG | GGC | GAT | GAG | GCA | CAG | GCT | GCT | TCA | GGA | ACC | GCT | CGA | GCC | GCG | 1548 |
| Leu | Leu | Gly | Asp | Glu | Ala | Gln | Ala | Ala | Ser | Gly | Thr | Ala | Arg | Ala | Ala | |
| | | | 1495 | | | | 1500 | | | | | 1505 | | | | |
| TCA | GGA | AAA | GCA | AGG | GCT | GCC | TCA | GGC | CGC | ATA | AGG | CAG | CTG | ACT | CTC | 1596 |
| Ser | Gly | Lys | Ala | Arg | Ala | Ala | Ser | Gly | Arg | Ile | Arg | Gln | Leu | Thr | Leu | |
| | | | 1510 | | | | 1515 | | | | | 1520 | | | | |
| GCC | GCC | GAC | AAG | GGG | TAC | GAG | GTA | GTC | GCG | AAT | CTA | TTC | CAG | GTG | CCC | 1644 |
| Ala | Ala | Asp | Lys | Gly | Tyr | Glu | Val | Val | Ala | Asn | Leu | Phe | Gln | Val | Pro | |
| | | | 1525 | | | | 1530 | | | | | 1535 | | | | |
| CAG | AAT | CCC | GTA | GTC | GAC | GGG | ATT | CTT | GCT | TCA | CCC | GGG | ATA | CTT | CGC | 1692 |
| Gln | Asn | Pro | Val | Val | Asp | Gly | Ile | Leu | Ala | Ser | Pro | Gly | Ile | Leu | Arg | |
| 1540 | | | | | 1545 | | | | | 1550 | | | | | 1555 | |

```
GGT GCA CAC AAC CTC GAC TGC GTG CTA AGA GAG GGT GCC ACG CTA TTC     1740
Gly Ala His Asn Leu Asp Cys Val Leu Arg Glu Gly Ala Thr Leu Phe
            1560            1565                1570

CCT GTG GTC ATT ACG ACA GTG GAA GAC GCC ATG ACA CCC AAA GCA CTG     1788
Pro Val Val Ile Thr Thr Val Glu Asp Ala Met Thr Pro Lys Ala Leu
        1575                1580                1585

AAC AGC AAA ATG TTT GCT GTC ATT GAA GGC GTG CGA GAA GAC CTC CAA     1836
Asn Ser Lys Met Phe Ala Val Ile Glu Gly Val Arg Glu Asp Leu Gln
            1590                1595                1600

CCT CCA TCT CAA AGA GGA TCC TTC ATA CGA ACT CTC TCC GGA CAC AGA     1884
Pro Pro Ser Gln Arg Gly Ser Phe Ile Arg Thr Leu Ser Gly His Arg
            1605            1610                1615

GTC TAT GGA TAT GCT CCA GAT GGG GTA CTT CCA CTG GAG ACT GGG AGA     1932
Val Tyr Gly Tyr Ala Pro Asp Gly Val Leu Pro Leu Glu Thr Gly Arg
1620                1625                1630                1635

GAC TAC ACC GTT GTC CCA ATA GAT GAT GTC TGG GAC GAC AGC ATT ATG     1980
Asp Tyr Thr Val Val Pro Ile Asp Asp Val Trp Asp Asp Ser Ile Met
                1640                1645                1650

CTG TCC AAG GAC CCC ATA CCT CCT ATT GTG GGA AAC AGT GGA AAC CTA     2028
Leu Ser Lys Asp Pro Ile Pro Pro Ile Val Gly Asn Ser Gly Asn Leu
            1655                1660                1665

GCC ATA GCT TAC ATG GAT GTG TTT CGA CCC AAA GTC CCC ATC CAT GTG     2076
Ala Ile Ala Tyr Met Asp Val Phe Arg Pro Lys Val Pro Ile His Val
            1670                1675                1680

GCC ATG ACG GGA GCC CTC AAC GCT TGT GGC GAG ATT GAG AAA ATA AGC     2124
Ala Met Thr Gly Ala Leu Asn Ala Cys Gly Glu Ile Glu Lys Ile Ser
        1685                1690                1695

TTC AGA AGC ACC AAG CTC GCC ACC GCA CAC CGG CTT GGC CTC AAG TTG     2172
Phe Arg Ser Thr Lys Leu Ala Thr Ala His Arg Leu Gly Leu Lys Leu
1700                1705                1710                1715

GCT GGT CCC GGA GCA TTC GAT GTA AAC ACC GGG CCC AAC TGG GCA ACG     2220
Ala Gly Pro Gly Ala Phe Asp Val Asn Thr Gly Pro Asn Trp Ala Thr
                1720                1725                1730

TTC ATC AAA CGT TTC CCT CAC AAT CCA CGC GAC TGG GAC AGG CTC CCC     2268
Phe Ile Lys Arg Phe Pro His Asn Pro Arg Asp Trp Asp Arg Leu Pro
            1735                1740                1745

TAC CTC AAC CTT CCA TAC CTT CCA CCC AAT GCA GGA CGC CAG TAC CAC     2316
Tyr Leu Asn Leu Pro Tyr Leu Pro Pro Asn Ala Gly Arg Gln Tyr His
            1750                1755                1760

CTT GCC ATG GCT GCA TCA GAG TTT AAA GAG ACC CCT GAA CTC GAG AGC     2364
Leu Ala Met Ala Ala Ser Glu Phe Lys Glu Thr Pro Glu Leu Glu Ser
    1765                1770                1775

GCC GTC AGA GCC ATG GAA GCA GCA GCC AAT GTG GAC CCA CTG TTC CAA     2412
Ala Val Arg Ala Met Glu Ala Ala Ala Asn Val Asp Pro Leu Phe Gln
1780                1785                1790                1795

TCT GCA CTC AGT GTG TTC ATG TGG CTG GAA GAG AAT GGG ATT GTG GCT     2460
Ser Ala Leu Ser Val Phe Met Trp Leu Glu Glu Asn Gly Ile Val Ala
                1800                1805                1810

GAC ATG GCC AAT TTC GCA CTC AGC GAC CCG AAC GCC CAT CGG ATG CGA     2508
Asp Met Ala Asn Phe Ala Leu Ser Asp Pro Asn Ala His Arg Met Arg
            1815                1820                1825

AAT TTT CTT GCA AAC GCA CCA CAA GCA GGC AGC AAG TCG CAA AGG GCC     2556
Asn Phe Leu Ala Asn Ala Pro Gln Ala Gly Ser Lys Ser Gln Arg Ala
        1830                1835                1840

AAG TAC GGG ACA GCA GGC TAC GGA GTG GAG GCC CGG GGC CCC ACA CCA     2604
Lys Tyr Gly Thr Ala Gly Tyr Gly Val Glu Ala Arg Gly Pro Thr Pro
    1845                1850                1855

GAG GAA GCA CAG AGG GAA AAA GAC ACA CGG ATC TCA AAG AAG ATG GAG     2652
Glu Glu Ala Gln Arg Glu Lys Asp Thr Arg Ile Ser Lys Lys Met Glu
1860                1865                1870                1875
```

```
ACC ATG GGC ATC TAC TTT GCA ACA CCA GAA TGG GTA GCA CTC AAT GGG         2700
Thr Met Gly Ile Tyr Phe Ala Thr Pro Glu Trp Val Ala Leu Asn Gly
        1880                    1885                    1890

CAC CGA GGG CCA AGC CCC GGC CAG CTA AAG TAC TGG CAG AAC ACA CGA         2748
His Arg Gly Pro Ser Pro Gly Gln Leu Lys Tyr Trp Gln Asn Thr Arg
        1895                    1900                    1905

GAA ATA CCG GAC CCA AAC GAG GAC TAT CTA GAC TAC GTG CAT GCA GAG         2796
Glu Ile Pro Asp Pro Asn Glu Asp Tyr Leu Asp Tyr Val His Ala Glu
        1910                    1915                    1920

AAG AGC CGG TTG GCA TCA GAA GAA CAA ATC CTA AAG GCA GCT ACG TCG         2844
Lys Ser Arg Leu Ala Ser Glu Glu Gln Ile Leu Lys Ala Ala Thr Ser
        1925                    1930                    1935

ATC TAC GGG GCT CCA GGA CAG GCA GAG CCA CCC CAA GCT TTC ATA GAC         2892
Ile Tyr Gly Ala Pro Gly Gln Ala Glu Pro Pro Gln Ala Phe Ile Asp
1940                    1945                    1950                1955

GAA GTT GCC AAA GTC TAT GAA ATC AAC CAT GGA CGT GGC CCT AAC CAA         2940
Glu Val Ala Lys Val Tyr Glu Ile Asn His Gly Arg Gly Pro Asn Gln
        1960                    1965                    1970

GAA CAG ATG AAA GAT CTG CTC TTG ACT GCA ATG GAG ATG AAG CAT CGC         2988
Glu Gln Met Lys Asp Leu Leu Leu Thr Ala Met Glu Met Lys His Arg
        1975                    1980                    1985

AAC CCC AGG CGG GCT CCA CCA AAG CCC AAG CCA AAA CCC AAT GCT CCA         3036
Asn Pro Arg Arg Ala Pro Pro Lys Pro Lys Pro Lys Pro Asn Ala Pro
        1990                    1995                    2000

ACA CAG AGA CCC CCT GGT CGG CTG GGC CGC TGG ATC AGG ACC GTC TCT         3084
Thr Gln Arg Pro Pro Gly Arg Leu Gly Arg Trp Ile Arg Thr Val Ser
        2005                    2010                    2015

GAT GAG GAC CTT GAG TGAGGCCCCT GGGGGTCTCC CGACACCACC CGCGCAGGCG         3139
Asp Glu Asp Leu Glu
2020

TGGACACCAA TTCGGCCTTA CAACATCCCA AATTGGATCC G                           3180
```

( 2 ) INFORMATION FOR SEQ ID NO:14:

( i ) SEQUENCE CHARACTERISTICS:
        ( A ) LENGTH: 1012 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Thr Asn Leu Gln Asp Gln Thr His Gln Ile Val Pro Phe Ile Arg
 1               5                  10                      15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
            35                  40                      45

Val Gly Asp Thr Gly Ser Gly Leu Ile Val Phe Phe Pro Gly Phe Pro
        50              55                  60

Gly Ser Ile Val Gly Ala His Tyr Thr Leu Gln Ser Ser Gly Asn Tyr
 65                      70                  75                 80

Lys Phe Asp Gln Met Leu Leu Thr Ala Gln Asn Leu Pro Ala Ser Tyr
                85                  90                      95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                     135                 140
```

| Met | Ser | Ala | Thr | Ala | Asn | Ile | Asn | Asp | Lys | Ile | Gly | Asn | Val | Leu | Val |
| 145 | | | | | 150 | | | | | 155 | | | | | 160 |

| Gly | Glu | Gly | Val | Thr | Val | Leu | Ser | Leu | Pro | Thr | Ser | Tyr | Asp | Leu | Gly |
| | | | | 165 | | | | | 170 | | | | | 175 | |

| Tyr | Val | Arg | Leu | Gly | Asp | Pro | Ile | Pro | Ala | Ile | Gly | Leu | Asp | Pro | Lys |
| | | | 180 | | | | | 185 | | | | | 190 | | |

| Met | Val | Ala | Thr | Cys | Asp | Ser | Ser | Asp | Arg | Pro | Arg | Val | Tyr | Thr | Ile |
| | | | 195 | | | | 200 | | | | | 205 | | | |

| Thr | Ala | Ala | Asp | Asn | Tyr | Gln | Phe | Ser | Ser | Gln | Tyr | Gln | Thr | Gly | Gly |
| | 210 | | | | | 215 | | | | | 220 | | | | |

| Val | Thr | Ile | Thr | Leu | Phe | Ser | Ala | Asn | Ile | Asp | Ala | Ile | Thr | Ser | Leu |
| 225 | | | | | 230 | | | | | 235 | | | | | 240 |

| Ser | Val | Gly | Gly | Glu | Leu | Val | Phe | Lys | Thr | Ser | Val | Gln | Ser | Leu | Val |
| | | | | 245 | | | | | 250 | | | | | 255 | |

| Leu | Gly | Ala | Thr | Ile | Tyr | Leu | Ile | Gly | Phe | Asp | Gly | Thr | Ala | Val | Ile |
| | | | 260 | | | | | 265 | | | | | 270 | | |

| Thr | Arg | Ala | Val | Ala | Ala | Asn | Asn | Gly | Leu | Thr | Ala | Gly | Ile | Asp | Asn |
| | | 275 | | | | | 280 | | | | | 285 | | | |

| Leu | Met | Pro | Phe | Asn | Leu | Val | Ile | Pro | Thr | Asn | Glu | Ile | Thr | Gln | Pro |
| | 290 | | | | | 295 | | | | | 300 | | | | |

| Ile | Thr | Ser | Ile | Ile | Leu | Glu | Ile | Val | Thr | Ser | Lys | Ser | Asp | Gly | Gln |
| 305 | | | | | 310 | | | | | 315 | | | | | 320 |

| Ala | Gly | Glu | Gln | Met | Ser | Trp | Ser | Ala | Ser | Gly | Ser | Leu | Ala | Val | Thr |
| | | | | 325 | | | | | 330 | | | | | 335 | |

| Ile | His | Gly | Gly | Asn | Tyr | Pro | Gly | Ala | Leu | Arg | Pro | Val | Thr | Leu | Val |
| | | | 340 | | | | | 345 | | | | | 350 | | |

| Ala | Tyr | Glu | Arg | Val | Ala | Thr | Gly | Ser | Val | Val | Thr | Val | Ala | Gly | Val |
| | | 355 | | | | | 360 | | | | | 365 | | | |

| Ser | Asn | Phe | Glu | Leu | Ile | Pro | Asn | Pro | Glu | Leu | Ala | Lys | Asn | Leu | Val |
| | 370 | | | | | 375 | | | | | 380 | | | | |

| Thr | Glu | Tyr | Gly | Arg | Phe | Asp | Pro | Gly | Ala | Met | Asn | Tyr | Thr | Lys | Leu |
| 385 | | | | | 390 | | | | | 395 | | | | | 400 |

| Ile | Leu | Ser | Glu | Arg | Asp | His | Leu | Gly | Ile | Lys | Thr | Val | Trp | Pro | Thr |
| | | | | 405 | | | | | 410 | | | | | 415 | |

| Arg | Glu | Tyr | Thr | Asp | Phe | Arg | Glu | Tyr | Phe | Met | Glu | Val | Ala | Asp | Leu |
| | | | 420 | | | | | 425 | | | | | 430 | | |

| Asn | Ser | Pro | Leu | Lys | Ile | Ala | Gly | Ala | Phe | Gly | Phe | Lys | Asp | Ile | Ile |
| | | 435 | | | | | 440 | | | | | 445 | | | |

| Arg | Ala | Ile | Arg | Arg | Ile | Ala | Val | Pro | Val | Val | Ser | Thr | Leu | Phe | Pro |
| | 450 | | | | | 455 | | | | | 460 | | | | |

| Pro | Ala | Ala | Pro | Leu | Ala | His | Ala | Ile | Gly | Glu | Gly | Val | Asp | Tyr | Leu |
| 465 | | | | | 470 | | | | | 475 | | | | | 480 |

| Leu | Gly | Asp | Glu | Ala | Gln | Ala | Ala | Ser | Gly | Thr | Ala | Arg | Ala | Ala | Ser |
| | | | | 485 | | | | | 490 | | | | | 495 | |

| Gly | Lys | Ala | Arg | Ala | Ala | Ser | Gly | Arg | Ile | Arg | Gln | Leu | Thr | Leu | Ala |
| | | | 500 | | | | | 505 | | | | | 510 | | |

| Ala | Asp | Lys | Gly | Tyr | Glu | Val | Val | Ala | Asn | Leu | Phe | Gln | Val | Pro | Gln |
| | | 515 | | | | | 520 | | | | | 525 | | | |

| Asn | Pro | Val | Val | Asp | Gly | Ile | Leu | Ala | Ser | Pro | Gly | Ile | Leu | Arg | Gly |
| | 530 | | | | | 535 | | | | | 540 | | | | |

| Ala | His | Asn | Leu | Asp | Cys | Val | Leu | Arg | Glu | Gly | Ala | Thr | Leu | Phe | Pro |
| 545 | | | | | 550 | | | | | 555 | | | | | 560 |

| Val | Val | Ile | Thr | Thr | Val | Glu | Asp | Ala | Met | Thr | Pro | Lys | Ala | Leu | Asn |

-continued

|  |  |  |  | 565 |  |  |  | 570 |  |  |  | 575 |  |
|---|---|---|---|---|---|---|---|---|---|---|---|---|---|

Ser Lys Met Phe Ala Val Ile Glu Gly Val Arg Glu Asp Leu Gln Pro
              580                   585                   590

Pro Ser Gln Arg Gly Ser Phe Ile Arg Thr Leu Ser Gly His Arg Val
            595                   600                   605

Tyr Gly Tyr Ala Pro Asp Gly Val Leu Pro Leu Glu Thr Gly Arg Asp
        610                   615                   620

Tyr Thr Val Val Pro Ile Asp Asp Val Trp Asp Asp Ser Ile Met Leu
625                       630                   635                   640

Ser Lys Asp Pro Ile Pro Pro Ile Val Gly Asn Ser Gly Asn Leu Ala
                645                   650                   655

Ile Ala Tyr Met Asp Val Phe Arg Pro Lys Val Pro Ile His Val Ala
            660                   665                   670

Met Thr Gly Ala Leu Asn Ala Cys Gly Glu Ile Glu Lys Ile Ser Phe
        675                   680                   685

Arg Ser Thr Lys Leu Ala Thr Ala His Arg Leu Gly Leu Lys Leu Ala
    690                   695                   700

Gly Pro Gly Ala Phe Asp Val Asn Thr Gly Pro Asn Trp Ala Thr Phe
705                   710                   715                   720

Ile Lys Arg Phe Pro His Asn Pro Arg Asp Trp Asp Arg Leu Pro Tyr
                725                   730                   735

Leu Asn Leu Pro Tyr Leu Pro Pro Asn Ala Gly Arg Gln Tyr His Leu
            740                   745                   750

Ala Met Ala Ala Ser Glu Phe Lys Glu Thr Pro Glu Leu Glu Ser Ala
        755                   760                   765

Val Arg Ala Met Glu Ala Ala Asn Val Asp Pro Leu Phe Gln Ser
    770                   775                   780

Ala Leu Ser Val Phe Met Trp Leu Glu Glu Asn Gly Ile Val Ala Asp
785                   790                   795                   800

Met Ala Asn Phe Ala Leu Ser Asp Pro Asn Ala His Arg Met Arg Asn
                805                   810                   815

Phe Leu Ala Asn Ala Pro Gln Ala Gly Ser Lys Ser Gln Arg Ala Lys
            820                   825                   830

Tyr Gly Thr Ala Gly Tyr Gly Val Glu Ala Arg Gly Pro Thr Pro Glu
        835                   840                   845

Glu Ala Gln Arg Glu Lys Asp Thr Arg Ile Ser Lys Lys Met Glu Thr
    850                   855                   860

Met Gly Ile Tyr Phe Ala Thr Pro Glu Trp Val Ala Leu Asn Gly His
865                   870                   875                   880

Arg Gly Pro Ser Pro Gly Gln Leu Lys Tyr Trp Gln Asn Thr Arg Glu
                885                   890                   895

Ile Pro Asp Pro Asn Glu Asp Tyr Leu Asp Tyr Val His Ala Glu Lys
            900                   905                   910

Ser Arg Leu Ala Ser Glu Glu Gln Ile Leu Lys Ala Ala Thr Ser Ile
    915                   920                   925

Tyr Gly Ala Pro Gly Gln Ala Glu Pro Pro Gln Ala Phe Ile Asp Glu
    930                   935                   940

Val Ala Lys Val Tyr Glu Ile Asn His Gly Arg Gly Pro Asn Gln Glu
945                   950                   955                   960

Gln Met Lys Asp Leu Leu Leu Thr Ala Met Glu Met Lys His Arg Asn
                965                   970                   975

Pro Arg Arg Ala Pro Pro Lys Pro Lys Pro Lys Pro Asn Ala Pro Thr
            980                   985                   990

```
Gln  Arg  Pro  Pro  Gly  Arg  Leu  Gly  Arg  Trp  Ile  Arg  Thr  Val  Ser  Asp
          995                      1000                     1005
Glu  Asp  Leu  Glu
     1010
```

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:15:

```
Ser  Trp  Ser  Ala  Ser  Gly  Ser
 1                   5
```

CHIMERIC INFECTIOUS BURSAL DISEASE VIRUS CDNA CLONES, EXPRESSION PRODUCTS AND VACCINES BASED THEREON

BACKGROUND OF THE INVENTION

1. Field of the Invention

The present invention provides chimeric IBDV immunogens which actively protect against virulent and lethal challenge by Classic and variant IBDV strains, and methods for obtaining vaccines containing these chimeric immunogens and vaccines.

2. Discussion of the Background

Infectious bursal disease virus (IBDV) is responsible for a highly contagious immunosuppressive disease in young chickens which causes significant losses to the poultry industry worldwide (reviewed in Kibenge (1988) "J. Gen. Virol.", 69:1757–1775). Infection of susceptible chickens with virulent IBDV strains can lead to a highly contagious immunosuppressive condition known as infectious bursal disease (IBD). Damage caused to the lymphoid follicles of the bursa of Fabricius and spleen can exacerbate infections caused by other agents and reduce a chicken's ability to respond to vaccination as well (Cosgrove (1962) "Avian Dis.", 6:385–3894).

There are two serotypes of IBDV (McFerran et al (1980) "Avian Path.", 9:395–404). Serotype 1 viruses are pathogenic to chickens and differ markedly in their virulence (Winterfield et al (1978) "Avian Dis.", 5:253–260), whereas serotype 2 viruses, isolated from turkeys, are avirulent for chickens (Ismail et al (1988) "Avian Dis.", 32:757–759; Kibenge (1991) "Virology", 184:437–440).

IBDV is a member of the Birnaviridae family and its genome consists of two segments of double-stranded RNA (Dobos et al (1979) "J. Virol.", 32:593–605). The smaller segment B (~2800 bp) encodes VP1, the dsRNA polymerase. The larger genomic segment A (~3000 bp) encodes a 110 kDa precursor polyprotein in a single open reading frame (ORF) that is processed into mature VP2, VP3 and VP4 (Azad et al (1985) "Virology", 143:35–44). From a small ORF partly overlapping with the polyprotein ORF, segment A can also encode VP5, a 17 kDa protein of unknown function (Kibenge et al (1991) "J. Gen. Virol.", 71:569–577).

While VP2 and VP3 are the major structural proteins of the virion, VP2 is the major host-protective immunogen and causes induction of neutralizing antibodies (Becht et al (1988) "J. Gen. Virol.", 69:631–640; Fahey et al (1989) "J. Gen. Virol.", 70:1473–1481). VP3 is considered to be a group-specific antigen because it is recognized by monoclonal antibodies (Mabs) directed against VP3 from strains of both serotype 1 and 2 (Becht et al (1988) "J. Gen. Virol.", 69:631–640). VP4 is a virus-coded protease and is involved in the processing of the precursor protein (Jagadish et al (1988) "J. Virol.", 62:1084–1087).

In the past, control of IBDV infection in young chickens has been achieved by live vaccination with avirulent strains, or principally by the transfer of maternal antibody induced by the administration of live and killed IBDV vaccines to breeder hens. Unfortunately, in recent years, virulent variant strains of IBDV have been isolated from vaccinated flocks in the United States (Snyder et al (1988b) "Avian Dis.", 32:535–539; Van der Marel et al (1990) "Dtsch. Tierarztl. Wschr.", 97:81–83). The use of a select panel of Mabs, raised against various strains of IBDV, has led to the identification of naturally occurring GLS, DS326, RS593 and Delaware variant viruses in the United States. Substantial economic losses have been sustained due to the emergence of these antigenic variants (Delaware and GLS) in the field (Snyder et al (1992) "Arch. Virol.", 127:89–101, copending U.S. patent application Ser. No. 08/216,841, filed Mar. 24, 1994, Attorney Docket No. 2747-053-27, Snyder, copending herewith). These variant strains are antigenically different from the Classic strains of IBDV most typically isolated before 1985, and lack epitope(s) defined by neutralizing monoclonal antibodies (Mabs) B69 and R63 (Snyder et al (1988a) "Avian Dis.", 32:527–534; Snyder et al (1998b) "Avian Dis.", 32:535–539; Snyder et al (1992) "Arch. Virol.", 127:89–101). Since the appearance of these variant strains in the field, many commercially available live and killed vaccines for IBDV have been reformulated in an attempt to better match the greater antigenic spectrum of viruses recognized to be circulating in the field.

Efforts to develop a recombinant vaccine for IBDV have been made, and the genome of IBDV has been cloned (Azad et al (1985) "Virology", 143:35–44). The VP2 gene of IBDV has been cloned and expressed in yeast (Macreadie et al (1990) "Vaccine", 8:549–552), as well as in a recombinant fowlpox virus (Bayliss et al (1991) "Arch. Virol.", 120:193–205). When chickens were immunized with the VP2 antigen expressed from yeast, antisera afforded passive protection in chickens against IBDV infection. When used in active immunization studies, the fowlpox virus-vectored VP2 antigen afforded protection against mortality, but not against damage to the bursa of Fabricius.

Recently, the synthesis of VP2, VP3 and VP4 structural proteins of the variant GLS IBDV strain in a *baculovirus* expression system has been described (Vakharia et al (1993) "J. Gen. Virol.", 74:1201–1206). In an initial two dose active immunity study in SPF chickens, *baculovirus* expressed GLS proteins were able to confer 79% protection against virulent GLS challenge (Vakharia et al (1993) "J. Gen. Virol.", 74:1201–1206). In a subsequent extended study of active cross-immunity, by increasing the antigenic mass of the *baculovirus* expressed GLS protein, complete protection against the variant GLS and E/Del strains was obtained with a single dose, but only partial protection was afforded against the Classic STC strain unless two doses were administered.

In recent years, the complete, nucleotide sequences of the large segment A of five serotype 1 IBDV strains; 002-73 (Hudson et al (1986) "Nucleic Acids Res.", 14:001–5012), Cu-1, PBG98, 52/70 (Bayliss et al (1990) "J. Gen. Virol.", 71:1303–1312), STC (Kibenge (1990) "J. Gen. Virol.", 71:569–577), and serotype 2 OH strain (Kibenge (1991) "Virology", 184:437–440) have been determined. In addition, the VP2 gene of virulent Japanese IBDV strains (Lin et al (1993) "Avian Dis.", 37:315–323) and Delaware variants A and E (Lana et al (1992) "Virus Genes", 6:247–259; Heine et al (1991) "J. Gen. Virol.", 22:1835–1843) have been sequenced. However, noone has completely cloned and characterized the entire long segment of any United States IBDV variant.

SUMMARY OF THE INVENTION

The inventors have now identified the region of the IBDV genome which is responsible for antigenic variation. A DNA sequence containing the central variable region of VP2 protein, as well as a plasmid incorporating the same, have been constructed. This DNA sequence can be manipulated to generate desired virus neutralizing epitopes or immunogenic polypeptides of any IBDV strain. In turn, these immunogenic segments can be incorporated into new recombinant IBDV vaccines.

BRIEF DESCRIPTION OF THE DRAWINGS

FIG. 5 reflects the DNA (SEQ ID NO:11) and amino acid sequence (SEQ ID NO:12) for the GLS virus structural protein fragment VP2/VP4/VP3. A vertical line indicates the start/stop points for the VP2, VP4 and VP3 regions.

FIG. 6 reflects the DNA (SEQ ID NO:13) and amino acid sequence (SEQ ID NO:14) for the E/Del 22 virus structural protein fragment VP2/VP4/VP3.

FIG. 7 is a table of the amino acid identities for key locations (epitopic determinants) of eight different IBDV.

DEFINITIONS

IBD—infectious bursal disease as described above.

IBDV—infectious bursal disease virus, a virus capable of, at a minimum, inducing lesions in the bursa of Fabricius in infected poultry.

Epitopic Determinants—amino acids or amino acid sequences which correspond to epitopes recognized by one or more monoclonal antibodies. Presence of the amino acid or amino acid sequence at the proper ORF location causes the polypeptide to exhibit the corresponding epitope. An epitopic determinant is identified by amino acid(s) identity and sequence location.

Genetic Epitopic Determinants—nucleotide sequences of the ORF which encode epitopic determinants.

Conformational Epitopes—epitopes induced, in part or in whole, by the quaternary (three-dimensional) structure of an IBDV polypeptide. Conformational epitopes may strengthen binding between an IBDV and a monoclonal antibody, or induce binding whereas the same sequence, lacking the conformational epitope, would not induce binding between the antibody and the IBDV polypeptide at all.

Virus-Like Particles—three-dimensional particles of natural or recombinant amino acid sequences mimicking the three-dimensional structure of IBDV (encoded by the large genome segment A) but lacking viral RNA. Virus-like particles exhibit conformational epitopes exhibited by native viruses of similar sequence. Virus-like particles are created by the proper expression of DNA encoding VP2, VP4, VP3 structural proteins in a proper ORF.

Epitopic Determinant Region—Limited region of amino acid sequence of VP2 of IBDV that is replete with epitopic determinants, variation among amino acids of this limited region giving rise to a high number of epitopes recognized by different monoclonal antibodies.

DETAILED DESCRIPTION OF THE PREFERRED EMBODIMENTS

Figure 1A:
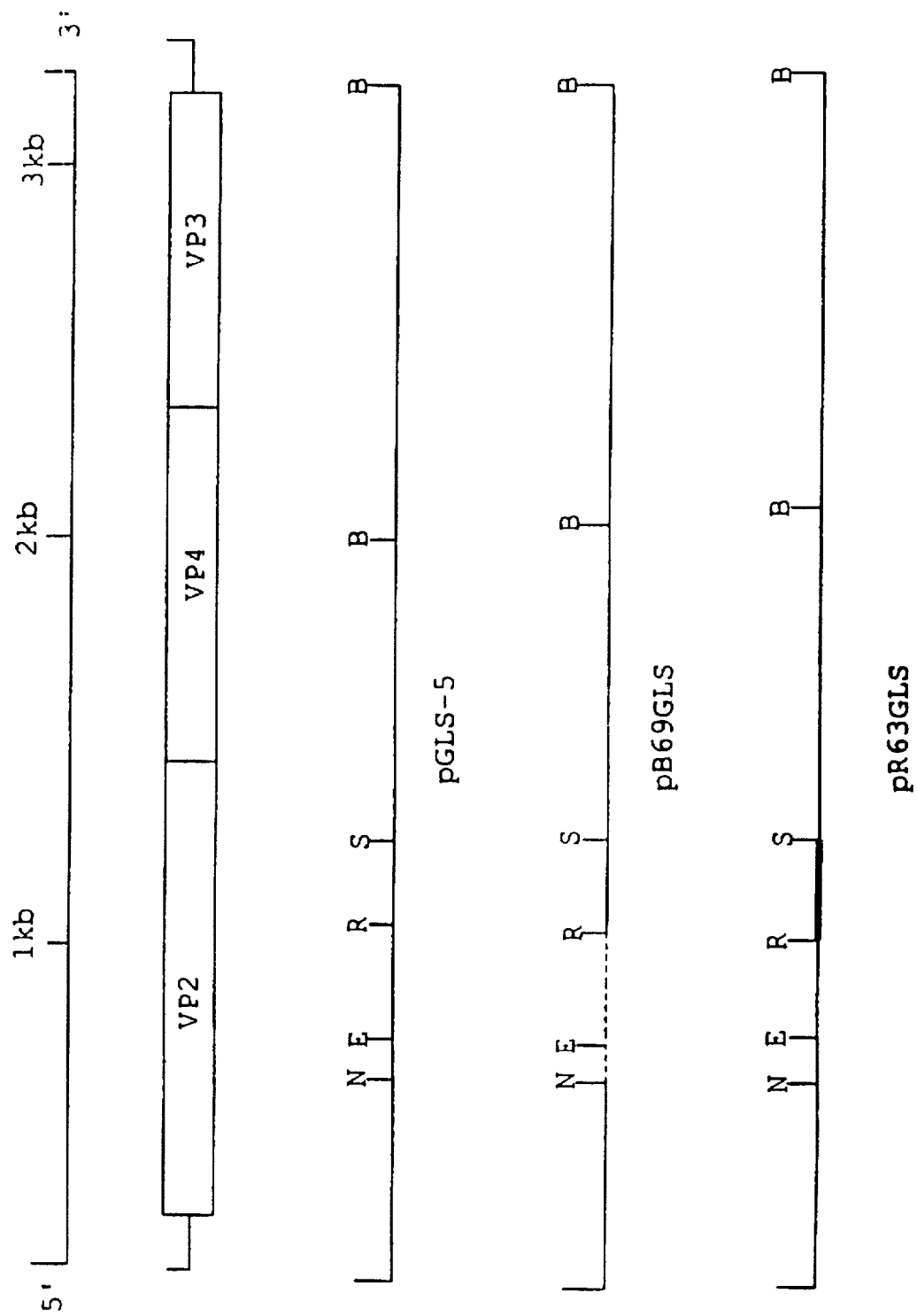
FIG. 1 illustrates the construction of various chimeric plasmids encoding IBDV-specific polyproteins. A map of the IBDV genome with its coding regions is shown at the top of the Figure. Selected restriction sites are incorporated in the Figure: B, BamHI; E, BstEII; N, NdeI; R, NarI; S, SpeI. Dashes indicate the substitution of the D78 sequence (NdeI-NarI fragment) into the GLS sequence to restore the B69 epitope region. Solid line and dotted line indicate the substitution of the E/Del-22 and DS326 sequences, respectively, into the GLS sequence to restore the B63 epitope region or to delete the 179 epitope region, respectively.

Recombinant, immunogenic polypeptides exhibiting the epitopes of two or more native IBDV, as well as recombinant virus-like particles exhibiting the epitopes of two or more native IBDV and conformational epitopes are effective immunogens for vaccines which can be used to confer protection against a wide variety of IBDV challenge in inoculated poultry. The recombinant polypeptides and virus-like particles are obtained by the expression of chimeric DNA prepared by the insertion, in the VP2 region of a base IBDV, of epitopic determinants for at least a second IBDV. This is most easily done by substitution of the genetic epitopic determinants for the amino acids identities and locations reflected in FIG. 7. Thus, where the epitopic determinant of the second IBDV differs from that of the base IBDV, the genetic epitopic determinant for the differing second IBDV is inserted in place of the genetic epitopic determinant at that location of the base IBDV. An example, combining epitopic determinants from the D78, E/Del 22 and DS326 IBDV into the base GLS IBDV is set forth in FIG. 1. Thus, one DNA sequence can be prepared with genetic epitopic determinants for a plurality of native IBDV. These recombinant plasmids can be inserted into a variety of packaging/expression vector, including *baculovirus*, fowlpox virus, Herpes virus of turkeys, adenovirus and similar transfection vectors. The vectors can be used to infect conventional expression cells, such as SF9 cells, chicken embryo fibroblast cell lines, chicken embryo kidney cells, vero cells and similar expression vehicles. Methods of transfection, and methods of expression, as well as plasmid insertion into transfection vehicles, are well known and do not constitute an aspect of the invention, per se.

The expression of the chimeric cDNA of the invention generate immunogenic polypeptides which reflect epitopes of a plurality of native IBDV, and the expression of a recombinant VP2, VP4, VP3 cDNA segment, with the VP2 region again comprising genetic epitopic determinants for at least two native IBDV give rise to immunogenic virus-like particles.

The immunogenic polypeptides and virus-like particles can be harvested using conventional techniques (Dobos et al, "J. Virol.", 32:593–605 (1979)). The polypeptides and virus-like particles can be used to prepare vaccines which will confer protection on inoculated poultry, in particular, chickens, and in a preferred embodiment, broiler chickens, protection against challenge from each IBDV bearing an epitope reflected in the plurality of epitopic determinants present in the inoculum. Thus, a single immunogen gives rise to immunity against a variety of IBDV, each IBDV whose genetic epitopic determinant has been incorporated in the chimeric cDNA.

The administration of the vaccines can be effectively done according to well-established procedures. In U.S. Pat. No. 5,064,646, which is incorporated herein by reference, methods are described for the effective inoculation of chicks based on the then novel isolation of GLS IBDV. Similar administration and dosage regimens can be employed herein. Since the polypeptides and virus-like particles lack viral RNA, they are avirulent. The vaccines may therefor be prepared by simple incorporation of the immunogenic polypeptides and virus-like particles in a pharmaceutical carrier, typically a suspension or mixture. Appropriate dosage values are best determined through routine trial and error techniques, given the different antibody titers induced and/or the quantity of different epitopes present which will induce complete cross-immunity to virulent challenge. In general, pharmacologically acceptable carriers such as a phosphate buffered saline, cell culture medium, Marek's virus vaccine diluent oil adjuvants and other adjuvants, etc., can be used. Administration is preferably done to hens entering egg laying periods which provides induction of antibody which is passively transferred through the egg to the chick to prevent early invention by virulent field strength IBDV. Conversely, the recombinant vaccine may be delivered in a replicating vector at any time in a chicken's life span, preferably at one day of age. Experience has demonstrated that, generally, that the level of protection may be improved by a second in oculation.

This invention may be further understood by reference to the specific examples set forth below.

EXAMPLES

Background Methodology

To determine the molecular basis of antigenic variation in IBDV, the genomic segment A of four IBDV strains: GLS, DS326, Delaware variant E (E/Del) and D78 was cloned and characterized by sequencing. By comparing the deduced amino acid sequences of these strains with other serotype 1 and 2 sequences published previously, the putative amino acid residues involved in the binding with various neutralizing Mabs were identified, and the phylogenetic relationship of IBDV structural proteins was examined.

GLS, DS326 and STC strains of IBDV were propagated in the bursa of specific-pathogen-free chickens (SPAFAS, Inc., Norwich, Conn., U.S.A.). Tissue culture adapted E/Del-22, D78 and OH (serotype 2) strains of IBDV were propagated in primary chicken embryo fibroblast cells derived from 10-day-old embryonated eggs (SPAFAS, Inc.) and purified as described (Snyder et al (1988a) "Avian Dis.", 32:527–534). The Mabs against various strains of IBDV were produced and characterized using protocols previously outlined (Snyder et al (1988a) "Avian Dis.", 32:527–534; Snyder et al (1988b) "Avian Dis.", 32:535–539). Mabs B69 and R63 were prepared against D78 strain, whereas Mabs 8, 10, 57 and 179 were prepared against GLS strain. In addition, a new Mab 67 was prepared which was neutralizing and specific for the E/Del strain. Identification of IBDV antigens by modified antigen capture ELISA (AC-ELISA) was carried out as described (Snyder et al (1992) "Arch. Virol.", 127:89–101).

Various strains of IBDV were characterized by their reactivities with a panel of neutralizing Mabs, as shown in Table 1.

TABLE 1

Antigenic characterization of various IBDV strains by their reactivites with a panel of neutralizing MAbs

| Virus Strains | Classification | Reactivities with MAbs | | | | | | |
|---|---|---|---|---|---|---|---|---|
| | | B69 | R63 | 179 | 8 | 10 | 57 | 67 |
| D78 | Classic | + | + | + | + | + | − | − |
| PBG98 | Classic | − | + | + | + | + | − | − |
| STC | Classic | + | + | + | + | + | − | − |
| 52/70 | Classic | + | + | + | + | − | − | − |
| OH(serotype 2) | Classic | + | + | + | + | − | − | − |
| E/Del | Variant | − | + | + | + | − | − | + |
| GLS | Variant | − | − | + | + | + | + | − |
| DS326 | Variant | − | − | − | + | + | + | − |

All standard serotype 1 viruses reacted with Mabs B69, R63, 179 and 8, except PBG98 (a British vaccine strain, Intervet, U. K.) which did not react with Mab B69. In contrast, all the U.S. variant viruses lack the virus-neutralizing B69 epitope. In addition, GLS and DS326 variants lack an R63 epitope but share a common epitope defined by the Mab 57. Thus, on the basis of the reactivities with various Mabs, these viruses were antigenically grouped as classic, GLS, DS326 and E/Del variants.

Complementary DNA clones, containing the entire coding region of the large RNA segment of various IBDV strains, were prepared using standard cloning procedures and methods previously described (Vakharia et al (1992) "Avian Dis.", 36:736–742; Vakharia et al (1993) "J. Gen. Virol.", 74:1201–1206). The complete nucleotide sequence of these cDNA clones was determined by the dideoxy method using a Sequenase DNA sequencing kit (U.S. Biochem. Corp., Columbus, Ohio). DNA sequences and deduced amino acid sequences were analyzed by a PC/GENE software package (Intelligenetics, Inc.), these are reflected in FIGS. 5 and 6. The nucleotide sequence data of the GLS strain has been deposited with GenBank Data Libraries and has been assigned an accession number M97346.

Figure 3A:
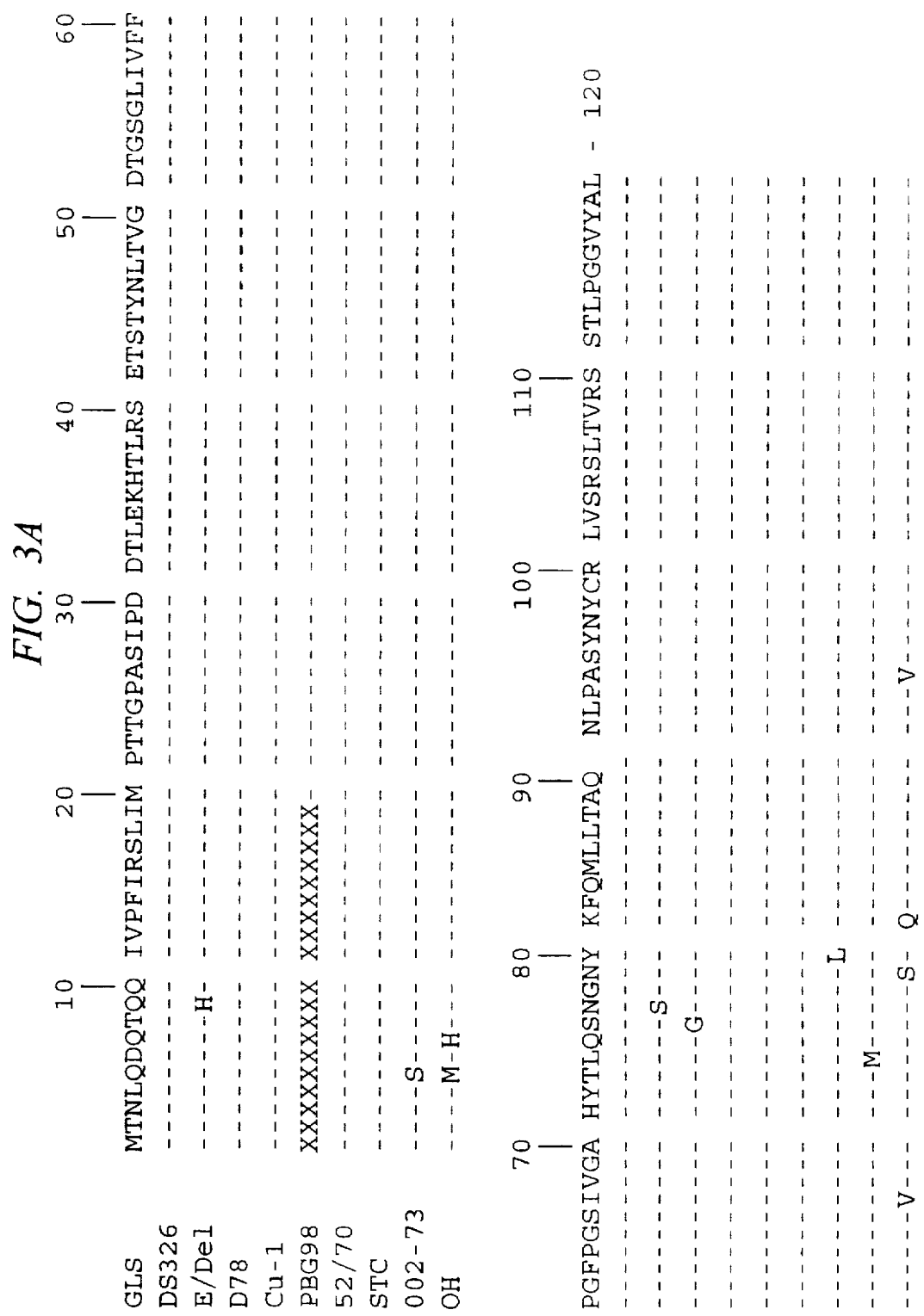
FIG. 3 is a comparison of the deduced amino acid sequences of the structural proteins (VP2, VP3 and VP4) of ten IBDV strains. (SEQ ID NOS:1–10) Dashes (—) indicate amino acid identity and crosses (x) denote a region where the sequence was not determined. Filled bar (■) indicates a gap in the sequence and vertical arrowheads (↓) mark the possible cleavage sites of VP2/VP4 and VP4/VP3. The two hydrophilic peaks in the variable region are overlined.
Figure 31:
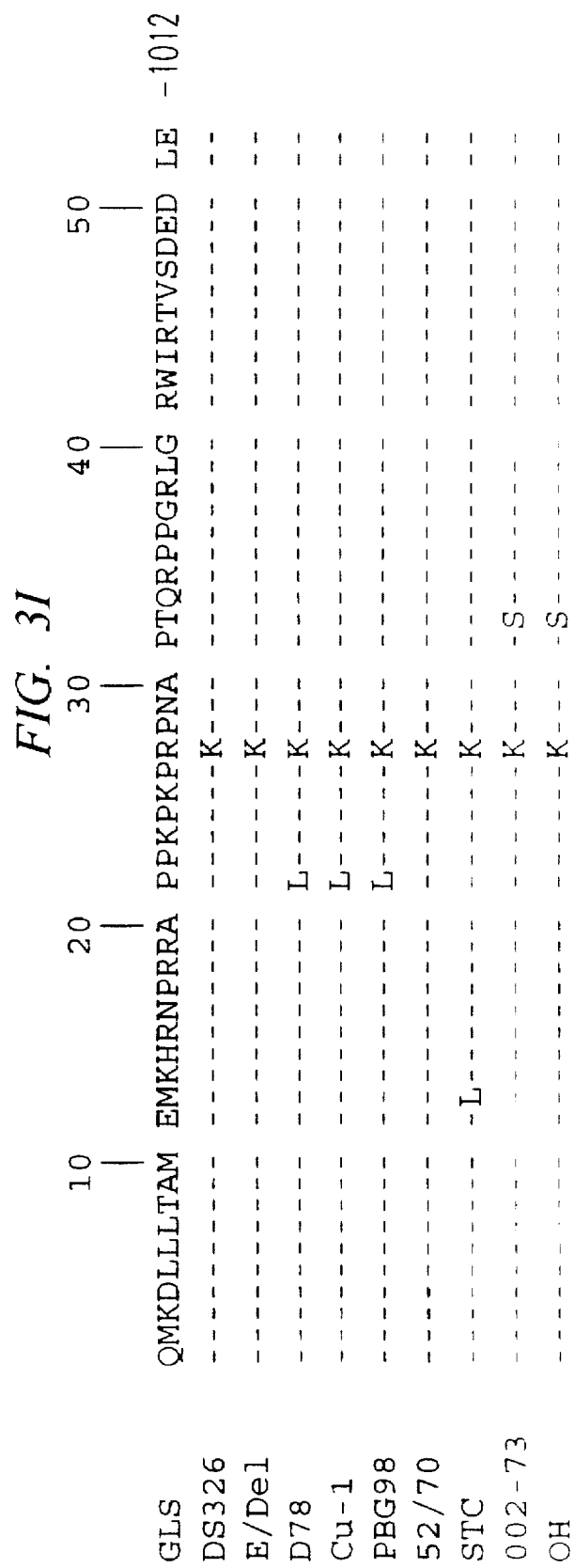

Comparisons of the nucleotide sequence of GLS strain (3230 bp long) with eight serotype 1 and one serotype 2 IBDV strains exhibit ≧92% and ≧82% sequence homology, respectively; indicating that these viruses are closely related. It is interesting to find that there are only six to nine base substitutions between D78, PBG98, and Cu1 strains which corresponds to a difference of about 0.2% to 0.3% (results not shown). FIG. 3 and Table 2 show a comparison of the deduced amino acid sequences and percent homology of the large ORF of segment A of the ten IBDV strains, including four IBDV strains used in this study.

TABLE 2

Percent amino acid sequence homology of large ORF of segment A of ten IBDV strains

| Strain | GLS | DS326 | E./Del | D78 | Cu-1 | PBG98 | 52/70 | STC | 002-73 | OH |
|---|---|---|---|---|---|---|---|---|---|---|
| GLS | | | | | | | | | | |
| DS326 | 98.7 | | | | | | | | | |
| E./Del | 98.4 | 98.3 | | | | | | | | |
| D78 | 98.5 | 98.1 | 97.9 | | | | | | | |
| Cu-1 | 98.6 | 98.2 | 98.0 | 99.6 | | | | | | |
| PBG98 | 98.5 | 98.1 | 97.9 | 99.5 | 99.5 | | | | | |
| 52/70 | 98.1 | 98.1 | 97.9 | 98.4 | 98.5 | 98.3 | | | | |
| STC | 97.7 | 98.0 | 97.5 | 98.4 | 98.5 | 98.3 | 98.3 | | | |
| 002-73 | 97.0 | 97.1 | 96.7 | 97.6 | 97.7 | 97.6 | 97.3 | 97.4 | | |
| OH | 90.0 | 90.0 | 89.7 | 90.2 | 90.3 | 90.2 | 89.8 | 90.3 | 90.1 | |

These comparisons show that the proteins are highly conserved. The degree of difference in the amino acid sequence ranges from 0.4% for the D78 versus Cu-1 comparison and 10.3% for the serotype 1 (E/Del) versus serotype 2 (OH) comparison (Table 2).

In FIG. 3, alignments of the deduced amino acid sequences of the large ORF (1012 residues) of ten IBDV strains (including four used in this study) show that most of the amino acid changes occur in the central variable region between residues 213 and 332 of VP2 protein, as shown earlier by Bayliss et al (1990) "J. Gen. Virol.", 71:1303–1312. It is interesting to note that all the U.S. variants (GLS, DS326 and E/Del) differ from the other strains in the two hydrophilic regions which are overlined in FIG. 3 (residues 212 to 223 and residues 314 to 324). These two hydrophilic regions have been shown to be important in the binding of neutralizing Mabs and hence may be involved in the formation of a virus-neutralizing epitope (Heine et al (1991) "J. Gen. Virol.", 22:1835–1843). Recently, we demonstrated that the conformation dependent Mabs B69, R63, 8, 179, 10, and 57 (see Table 2) immunoprecipitate VP2 protein (Snyder et al (1992) "Arch. Virol.", 127:89–101). In addition, E/Del specific Mab 67 also binds to VP2 protein. Therefore, to identify the amino acids involved in the formation of virus-neutralizing epitopes, and hence the antigenic variation, we compared the amino acid sequences of VP2 protein of classic and variant viruses.

Comparison of the D78 sequence with the PBG98 sequence shows only four amino acid substitutions at positions 76, 249, 280 and 326. However, STC and 52/70 strains also differ from the D78 sequence at positions 76, 280 and 326 but these viruses do bind to Mab B69. This implies that Gln at position 249 (Gln249) may be involved in the binding with Mab B69. It should be noted that all U.S. variant viruses have a Gln→Lys substitution at this position and hence escape the binding with neutralizing Mab B69. Similarly, comparison of the GLS sequence with the DS326 sequence in the variable region shows six amino acid substitutions at positions 222, 253, 269, 274, 311 and 320. However, other strains of IBDV that do bind to Mab 179 have amino acid substitutions at positions 222, 253, 269 and 274 that are conservative in nature. Therefore, this suggests that Glu311 and Gln320 may be involved in the binding with Mab 179. Again, comparison of GLS and DS326 sequences with all other IBDV sequences shows a unique Ala→Glu substitution at position 321, suggesting the contribution of this residue in the binding with Mab 57. Since Mab 57 does not compete with Mab R63, it is conceivable that Ala321 may contribute to the binding with Mab R63. Similarly, comparison of E/Del sequence with other sequences shows five unique substitutions at positions 213, 286, 309, 318 and 323. However, comparison of this E/Del sequence (from tissue culture derived virus) with previously published VP2 A/Del and E/Del sequences (bursa derived virus) suggests the involvement of Ile286, Asp318 and Glu323 in the binding with Mab 67 since residues at positions 213 and 309 are not substituted in A/Del and E/Del sequences, respectively (Heine et al (1991) "J. Gen. Virol.", 22:1835–1843; Lana et al (1992) "Virus Genes", 6:247–259; Vakharia et al (1992) "Avian Dis.", 36:736–742).

Comparisons of the amino acid sequence also show a striking difference between serotype 1 and serotype 2 sequences. In serotype 2 OH strain, there is an insertion of an amino acid residue at position 249 (serine) and a deletion of a residue at position 680. Previously, it has been shown that serotype 2 viruses are naturally avirulent and do not cause any pathological lesions in chickens (Ismail et al (1988) "Avian Dis.", 32:757–759). Thus, these subtle changes in the structural proteins of serotype 2 OH strain may play an important role in the pathogenicity of the virus. Moreover, it has been hypothesized that an amino acid sequence motif, S-W-S-A-S-G-S, (residues 326 to 332 SEQ ID NO:15) is conserved only in virulent strains and could be involved in virulence (Heine et al (1991) "J. Gen. Virol.", 22:1835–1843). This sequence motif was also conserved in various pathogenic strains of IBDV isolated in Japan (Lin et al (1993) "Avian Dis.", 37:315–323). Comparison of the amino acid sequences in this heptapeptide region reveals that nonpathogenic serotype 2 OH strain has three substitutions, whereas mildly pathogenic strains of serotype 1 (D78, Cu-1, PBG98 and 002-73) have one or two substitutions in this region. Moreover, comparison of the hydrophilicity plots of the variable region (amino acids 213 to 332) of variant serotype 1 strains and serotype 2 OH strain indicates a drastic reduction in the second hydrophilic peak region (amino acid residues 314 to 324) for serotype 2 (results not shown). Since most of the amino acid residues causing antigenic variation reside in this region, these residues may play an important role in the formation of virus-neutralizing epitopes, as well as serotype specificity.

Figure 4:
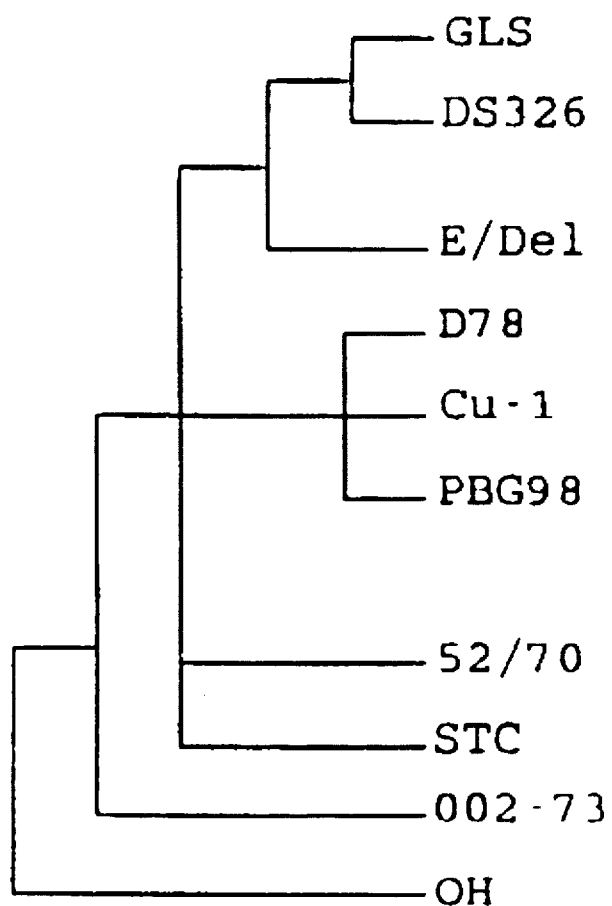
FIG. 4 is a phylogenetic tree for the IBDV structural proteins using the PAUP (phylogenetic analysis using parsimony) version 3.0 program (Illinois Natural History Survey, Champaign, Ill.).

To evaluate the antigenic relatedness of structural proteins of various IBDV strains, a phylogenetic tree was constructed, based on the large ORF sequences of ten IBDV strains, including the U.S. variant strains examined in this study (FIG. 4). Three distinguishable lineages were formed. The first one, which is most distant from the others, is serotype 2 OH strain, and the second one is the geographically distant Australian serotype 1 strain (002-73). The third lineage consists of four distinct groups. The first and second group include highly pathogenic strains, namely, standard challenge (STC) strain from U.S. and the British field strain (52/70). The third group comprises all the European strains:

the vaccine strains D78 (Holland), PBG98 (U.K.), and mildly pathogenic strain Cu-1 (Germany). The fourth group consists of the U.S. variant strains in which E/Del forms a different subgroup. The groups formed by the phylogenetic analysis correlate very well with the Mabs reactivity patterns (see Table 1). As shown in FIG. 4, all the U.S. variant viruses which lack the B69 epitope form a distinct group, whereas all the classic viruses containing a B69 epitope form another group (except PBG98). In addition, closely related GLS and DS326 strains containing a common Mab 57 epitope and lacking an R63 epitope could be separated from the other variant E/Del strain.

Based on this information, a recombinant vaccine was constructed as follows:

Construction of Recombinant *baculovirus* Clones Containing Chimeric IBDV Genes A recombinant *baculovirus* which expresses a chimeric VP2, VP3 and VP4 structural proteins of the GLS strain was constructed and assessed. The recombinant *baculovirus* expressed a chimeric VP2 protein incorporating all Mab defined GLS neutralization sites, as well as one neutralization site (B69) which is specific for Classic strains of IBDV in the form of a VP2-VP4-VP3 segment.

Complementary DNA clones, containing the entire coding region of the large RNA segment of the GLS and D78 IBDV strains, were prepared using standard cloning procedures and methods previously described (Vakharia et al (1992) "Avian Dis.", 36:736–742; Vakharia et al (1993) "J. Gen. Virol.", 74:1201–1206). To insert the gene sequence encoding the B69 epitope of the D78 IBDV strain, plasmid pB69GLS was constructed as follows (see FIG. 1). Full-length cDNA clones of D78 and GLS (plasmids pD78 and pGLS-5) were digested with NdeI-NarI and NarI-SpeI enzymes to release a NdeI-NarI (0.26 kb) and a NarI-SpeI (0.28 kb) fragments, respectively. These two fragments were then ligated into the NdeI-SpeI cut plasmid pGLS-5 to obtain a chimeric plasmid pB69GLS. As a result of this insertion, three amino acids were substituted in the GLS VP2 protein. These substitutions were at positions 222 (Thr-Pro), 249 (Lys-Gln) and 254 (Ser-Gly) in the variable region of the VP2 protein (Vakharia et al (1992) "Avian Dis.", 36:736–742). To insert the chimeric IBDV structural genes in the Baculovirus genome, plasmid pB69GLS was completely digested with BstEII enzyme and partially with the BamHI enzyme, combined with the NheI-BstEII fragment (derived from plasmid pGLSBacI, see Vakharia et al (1993) "J. Gen. Virol.", 74:1201–1206) and then ligated to the NheI-BamHI cut transfer vector pBlueBacII (Invitrogen Corp., San Diego, Calif.). Finally, recombinant *baculovirus* I-7 was obtained using previously described procedures (Vakharia et al (1993) "J. Gen. Virol.", 74:1201–1206). See Table 3.

Preparation of an Inoculum for Immunization

*Spodoptera frugiperda* SF9 cells, infected at a multiplicity of 5 PFU per cell with the I-7 recombinant *baculovirus*, were propagated as suspension cultures in one liter flasks containing Hink's TNM-FH medium (JHR Biosciences, Lenxa, Kans.) supplemented with 10% fetal calf serum at 28° C. for 3 to 4 days. The infected cells were recovered by low speed centrifugation, washed two times with PBS, and resuspended in a minimum volume of PBS. The cell slurry was sonicated on and ice bath three times for 1 min, with 2 min intervals and clarified by low speed centrifugation. An aliquot of each cell lysate was tested with anti-IBDV Mabs by AC-ELISA to estimate the antigenic mass present (Snyder et al (1998b) "Avian Dis.", 32:535–539). Preparations having the highest antigenic mass were pooled and comparatively titrated in AC-ELISA against the V-IBDV-7-1 recombinant *baculovirus* IBDV vaccine used in a previous study (Vakharia et al (1993) "J. Gen. Virol.", 74:1201–1206). The antigenic mass of the I-7 recombinant preparation, as determined by AC-ELISA with group specific neutralizing Mab 8, was adjusted by dilution to be the same as the V-IBDV-7-1 vaccine, and then it was emulsified with an equal volume of Freund's incomplete adjuvant and used for inoculation.

Viruses

The challenge viruses: Classic strains IM and STC, and variant strains E/Del and GLS-5 were obtained from previously acknowledged sources (Snyder et al (1988a) "Avian Dis.", 32:527–534; Snyder et al (1992) "Arch. Virol.", 127:89–101). After intraocular instillation, challenge viruses were titrated in the bursae of specific-pathogen-free (SPF) chickens (SPAFAS, Inc., Storrs, Conn.). For strains STC, E/Del and GLS-5, a 100 chick infective fifty percent dose (100 CID$_{50}$) was determined based on bursa to body weight measurements. One hundred lethal doses (100 LD) of the IM strain were calculated based on mortality at 8 days post-inoculation (PI).

Chicken Inoculations and IBDV Challenge

White leghorn SPF chickens were hatched and reared in HEPA filtered isolation units (Monair Anderson, Peachtree City, Ga.). Eight-week old chickens were prebled, individually wing banded, divided among 10 groups of 15 chicks each and treated as follows. Chickens of groups I–V received no inoculations and served as either negative or positive challenge controls. Chickens of group V–X were inoculated intramuscularly with 0.5 ml of the 1–7 inoculum prepared above from recombinant Baculovirus infected cell lysates. At 3 weeks PI, all chickens were bled and chickens of groups II–IX were challenged with the appropriate IBDV challenge strain by ocular instillation. Four days post-challenge, 5 chickens from each group were humanely sacrificed and their cloacal bursa were removed. Each bursa was processed and subsequently evaluated for the presence of IBDV antigen by AC-ELISA as described (Snyder et al (1998b) "Avian Dis.", 32:535–539). In addition, chickens in the IM challenged groups were scored as dead, and humanely sacrificed when they became obviously moribund due to IM challenge. Eight days post-infection, the remaining chickens in all groups were sacrificed and weighed. The bursa of Fabricius from each chicken was carefully excised and also weighed. Bursa weight to body weight ratio was calculated for each chicken as described by Lucio and Hitchner (Lucio et al (1979) "Avian Dis.", 23:466–478). Any value for individually challenged chickens falling plus or minus two standard deviation units from the mean of the corresponding control group was scored as a positive indicator of IBDV infection. Opened bursae were fixed by immersion in 10% neutral buffered formalin. Transverse portions of bursae were processed through graded alcohols and xylene, embedded into paraffin, sectioned, stained with hematoxylin-eosin, and examined with a light microscope. Protection against challenge was defined as the absence of any IBDV-induced lesions in the bursa of Fabricius.

Serological Evaluation

The Classic D78 strain, as well as the cell culture adapted variant GLS strain of IBDV were grown in primary chicken embryo fibroblast cells and used in virus neutralization (VN) tests to test sera from the vaccine trial essentially as described (Snyder et al (1988a) "Avian Dis.", 32:527–534). Serum from the trials was also tested for the presence of anti-IBDV antibody using a commercially available IBDV antibody ELISA kit (Kirkegaard and Perry, Gaithersburg, Md.).

Evaluation of Vaccines and Challenge Viruses

The antigenic content of the I-7 GLS chimeric IBDV vaccine was assessed in AC-ELISA with a panel of VP2 and VP3 specific Mabs. The relative antigenic mass of each epitope expressed in the I-7 vaccine was compared to previously tested lots of Baculovirus expressed unmodified GLS subunit vaccines (Vakharia et al (1993) "J. Gen. Virol.", 74:1201–1206). The status of each Mab defined epitope on the I-7 chimeric vaccine was also compared to the status of those Mab defined epitopes occurring on wild type IBDV challenge viruses used to evaluate the efficacy of the I-7 vaccine. Table 3 shows that antigenic mass levels at the 8, 57, and B29 epitopes for the current I-7 chimeric vaccine were similar to a recently tested unmodified V-IBDV-7-1 GLS subunit vaccine, but approximately 4-fold higher than the original unmodified V-IBDV-7 vaccine.

A major difference in the unmodified and chimeric vaccines was the appearance of the Classic B69 epitope in the chimeric GLS product. The level of the B69 epitope was arbitrarily set at 9 since no comparisons could be made to the unmodified GLS subunit vaccines. By comparing the status of Mab defined epitopes on the challenge viruses with the unmodified and chimeric GLS subunit vaccines (Table 3), it could be seen that while the chimeric product had expressed the B69 epitope found on the Classic STC and IM challenge viruses, that it also retained all of the homologous GLS epitopes.

Active-cross Protection

Table 4 shows the results of a cross-protection trial and serological results obtained prior to challenge.

TABLE 3

Comparative levels of IBDV, VP2, and VP3 monoclonal antibody (Mao) defined epitopes on recombinant baculovirus expresing IBDV proteins and status of Mab defined epitopes on challenge viruses used.

| Vaccine | Relative level of Mab epitope[A] | | | | | Challenge Virus | Status of Mab epitope[B] | | | | |
|---|---|---|---|---|---|---|---|---|---|---|---|
| | 8 | 57 | B69 | 67 | B29 | | 8[C] | 57[C] | B69[C] | 67[C] | B29[D] |
| V-IBD-7[E] | 1 | 1 | 0 | 0 | 1 | GLS | + | + | − | − | + |
| V-IBD-7-1[E] | 3 | 3 | 0 | 0 | 2 | STC | + | − | + | − | + |
| I-7[F] | 3 | 3 | 9 | 0 | 2 | IM | + | − | + | − | + |
| | | | | | | E./Del | + | − | − | + | + |

[A]The relative level of each Mab epitope was determined by AC-ELISA, and the level of each Mab epitope was set to 1 for the V-IBD-7 vaccine previously used (15). Maximum level is 9. Each 1.0 increment represents approximately twice the amount of the epitope present in the original V-IBD-7 vaccine. The V-IBD-7-1 vaccine was also previously reported (16).
[B]The status of Mab epitopes was determined by AC-ELISA and is presented as present (+) or absent (−).
[C]Neutralizing Mab epitope resides on VP2 of IBDV.
[D]Non-neutralizing Mab epitope resides on VP3 of IBDV.
[E]Recombinant baculovirus vaccines incorporating unmodified large segment A GLS proteins.
[F]Current recombinant baculovirus vaccine incorporating modified chimeric large segment A GLS proteins.

TABLE 4

Active cross-protection Induced 2-weeks post Immunization with baculovirus expressed chimeric I-7 IBDV antigens and associates prechallenge serology.

| Group No. | Vaccination[A] | Challenge[B] | Number Protected | | | Mean VN Titer [3]Log | | |
|---|---|---|---|---|---|---|---|---|
| | | | AC-ELISA[C] | Histo[D] | BBWR[D] | D78 | GLS | ELISA |
| I | None | None | NA | NA | NA | ≦4 | ≦4 | 0 |
| II | None | STC | 0/5 | 0/10 | 0/10 | ≦4 | ≦4 | 0 |
| III | None | IM | 0/5 | 0/5[E] | 5/5[E] | ≦4 | ≦4 | 0 |
| IV | None | E./Del | 0/5 | 0/10 | 0/10 | ≦4 | ≦4 | 0 |
| V | None | GLS-5 | 0/5 | 0/10 | 0/10 | ≦4 | ≦4 | 0 |
| VI | I-7 | STC | 5/5 | 10/10 | 10/10 | 10.7(1.8)[F] | 10.4(1.4)[F] | 1235(312)[F] |

TABLE 4-continued

Active cross-protection Induced 2-weeks post Immnuization with baculovirus expressed chimeric I-7 IBDV antigens and associates prechallenge serology.

| Group No. | Vaccination[A] | Challenge[B] | Number Protected | | | Mean VN Titer $^3$Log | | |
|---|---|---|---|---|---|---|---|---|
| | | | AC-ELISA[C] | Histo[D] | BBWR[D] | D78 | GLS | ELISA |
| VII | I-7 | IM | 5/5 | 10/10 | 10/10 | 10.0(1.4) | 10.4(2.1) | 1201(791) |
| VIII | I-7 | E./Del | 5/5 | 10/10 | 10/10 | 11.4(1.2) | 10.6(1.9) | 1089(409) |
| IX | I-7 | GLS-5 | 5/5 | 10/10 | 10/10 | 11.0(1.5) | 12.0(2.0) | 1220(339) |
| X | I-7 | None | 5/5 | NA | NA | 9.9(1.4) | 9.3(1.4) | 1140(473) |

[A]Vaccination was given at 8 weeks of age.
[B]Challenge virus was given by intraocular instillation 3-weeks post immunization or at 11-weeks of age for controls.
[C]Protection was determined by AC-ELISA examination of ½ of each group 4-days post-challenge.
[D]Protection was determined histologically and by bursa to body weight ratios at 8-days.
[E]Five chickens were scored as dead due to IM challenge prior to 8-days post-challenge.
[F]One standard deviation.

Groups II–V served as challenge controls and as indicated by AC-ELISA, bursa to body weight and histological assessments, all non-vaccinated chickens were fully susceptible to virulent IBDV challenge with all strains used. The IM challenge produced lethal disease in one-third of the control group chicks. In contrast, 8-week old chickens comprising Groups VI–IX were vaccinated once with the GLS chimeric vaccine, and 3-weeks PI all vaccinated chickens were completely protected from challenge by all challenge viruses, including lethal disease produced in controls by the IM strain. Serologically, titers from reciprocal-cross VN tests conducted on prechallenge sera with the D78 and GLS tissue culture viruses were essentially within 2-fold of one another. Mean ELISA titers were relatively low, but were also uniform between the vaccinated groups.

Characterization of Vaccines

In initial studies with Baculovirus expressed subunit GLS vaccines, after administration of two doses, the V-IBDV-7 GLS vaccine (Table 3) could only induce active antibody levels capable of providing 79% protection against homologous GLS challenge (Vakharia et al (1993) "J. Gen. Virol.", 74:1201–1206). In a subsequent study, the antigenic mass of the original V-IBDV-7 vaccine was increased approximately 4-fold (calculated at the group specific Mab 8 site) and initiated one dose and two dose vaccination cross-challenge trials with the unmodified GLS subunit vaccine designated as V-IBDV-7-1 (Table 3). In those trials, two doses of the vaccine yielded complete cross-protection against virulent STC, E/DEL and GLS challenge. However, in the one vaccine dose trial, while complete protection was attained against challenge with variant E/DEL and GLS viruses, only 44% protection was achieved against the more distantly related Classic STC virus. Those studies could mean that simply by increasing the antigenic mass and/or doses of the vaccine that better cross-protection could be obtained. However, it was also evident in the absence of homologous vaccination that lower levels of antibody, induced by one dose of the GLS V-IBDV-7-1 subunit vaccine, were not sufficiently cross-protective against Classic IBDV challenge. This could mean that in even lower levels of antibody, such as in cases of waning maternal antibody, that cross-protection would likely be even more reduced. Indeed, although not challenged with the STC virus, in some passive maternal antibody studies conducted using another dosage of the V-IBDV-7 vaccine, while homologous GLS protection was afforded, progeny of vaccinated hens were only 57% protected against a more closely related E/DEL challenge.

In a single-dose vaccination cross-challenge trial, the chimeric GLS I-7 vaccine, which incorporated the Classic B69 neutralization epitope, was evaluated. In order to make the current trial comparable to previous trials, the I-7 vaccine was formulated such that by AC-ELISA the relative antigenic mass of the I-7 chimeric subunit vaccine was nearly identical to the unmodified V-IBDV-7-1 vaccine previously used (Table 3). Table 4 shows the results of the cross-challenge after a single dose of the I-7 vaccine was administered. Results were similar to those obtained with the unmodified V-IBDV-7-1 vaccine previously used in that protection against the GLS and E/DEL strains was complete. However, the I-7 vaccine yielded complete protection against pathogenic and lethal challenge by the Classic STC and IM strains respectively. Since the antigenic mass of the GLS and group common epitopes on V-IBDV-7 and I-7 vaccines were carefully equilibrated and equal, it is reasonable to conclude that the comparative increase in efficacy of the I-7 vaccine against challenge with Classic IBDV strains was due solely to the incorporation of the Classic IBDV B69 neutralization epitope in the GLS VP2 protein sequence.

Virus-like Particles

As noted above, the recombinant CDNA and immunogens expressed thereby, of this invention may be confined to the VP2 immunogenic region. In other words, it may be sufficient to prepare a cDNA clone encoding epitopic determinants for a base IBDV, e.g., GLS, as well as a second IBDV epitopic determinant, such as D78. Other epitopic determinants, all in the VP2 epitopic determinant region may be incorporated, cloned and expressed as discussed above.

Figure 2A:
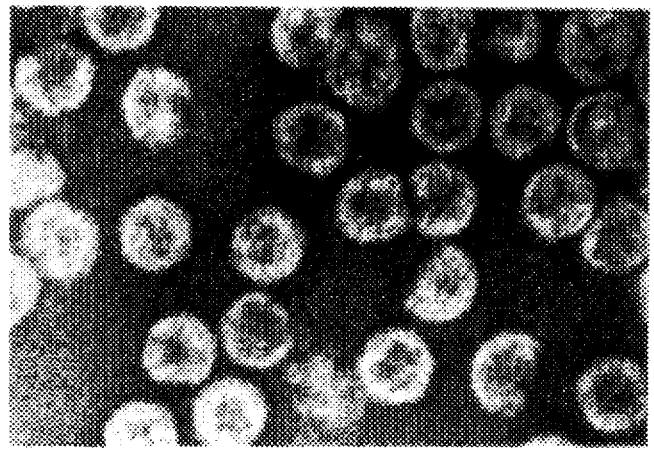
FIG. 2 is electron micrographs of IBDV virus-like particles (⊢⊣=100nm). A. Actual empty particles (without RNA) from purified virus. B. Virus-like particles (empty capsids) derived from a recombinant *baculovirus* expressing the large genome segment of IBDV in insect cells.
Figure 2B:
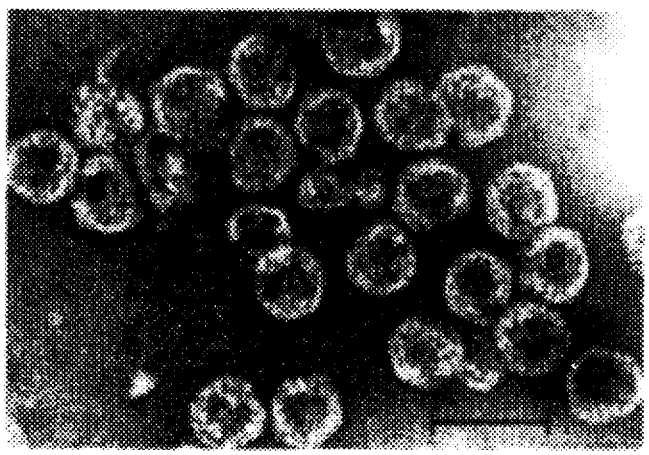

As reflected in FIG. 2, virus-like particles are generated by the expression of DNA encoding the VP2-VP4-VP3 structural protein sequences. These virus-like particle immunogens can be separated from the corresponding VP2 only immunogens, both in terms of monoclonal antibody and by conventional separation measures, such as electrophoresis and chromatography. The difference in reactivity with monoclonal antibody strongly indicates, however, that epitopes present in the VP2-VP4-VP3 structural protein sequence-induced virus-like particles are present that are not present in immunogens expressed by the identical VP2 only region. These epitopes are "both linear and conformational" epitopes. Conformational epitopes differ from linear epitopes and are reflected in the conformation, not only in amino acid sequence of the actual virus. As a result, inoculation of poultry with a recombinant virus-like particle may provide even superior protection against field challenge from IBDV than inoculation with the immunogens of the VP2 region only. This is due to the spontaneous assembly of all the structural elements of the virus.

Applicants have discovered that the expression of the VP2 region as part of the VP2-VP4-VP3 structural protein single segment generates virus-like particles such as those of FIG. 2. These particles have been demonstrated to react with antibodies which do not react similarly with the identical recombinant VP2 immunogen. Thus, the virus-like particles may give rise to higher antibody titers, and/or subtly different (broader) protection when a poultry host is inoculated therewith.

The invention herein therefore embraces (1) recombinant VP2 immunogens comprising epitopic determinants of at least two different IBDV strains and (2) virus-like particles of VP2-VP4-VP3 segments wherein the VP2 region again comprises epitopic determinants of at least two different IBDV strain, as well as the nucleotide sequences encoding both 1 and 2, and vaccines embracing the same.

Recombinant Epitopic Determinant Combinations

As reflected in the examples set forth above, genetic epitopic determinants for an IBDV strain can be inserted in the VP2 region of a different, base IBDV genetic sequence, and subsequently used to express an immunogen exhibiting epitopes for both IBDV. Indeed, the examples above demonstrate the combination of at least three different IBDV epitopic determinants. More can be combined. The resulting vaccine includes an active agent, the expressed immunogen, which provides challenge protection against a broad spectrum of IBDV, rather than prior art virus-based vaccines which give protection against a single strain, or a single family of strains.

FIG. 7 reflects the amino acid identities for the epitopic determinant region for seven different IBDV. These are not intended to be limiting, but are representative. Desirable recombinant immunogens, both VP2 only and virus-like particle VP2-VP4-VP3 immunogens are made by substituting the genetic epitopic determinants for the varying amino acids at the identified locations in FIG. 7 (locations not identified are conserved throughout the IBDV strains). This induces the expression of the inventive immunogens. Clearly, the possible combinations, while large in number, are limited, and may be investigated with routine skill. Representative combinations will tend to reflect combinations of epitopic determinants for dominant IBDV.

A E/Del/GLS recombinant may include changes in the E/Del epitopic determinant region at position 213, Asn-Asp, 253 Gln-His and 169 Thr Ser.

A DS326/D78 recombinant may include the amino acid, and corresponding nucleotide substitutions at 76Ser-Gly, 249 Lys-Gln, 253 Gln-His and 270 Ala-Thr substitutions.

Obviously, a wide variety of combinations are possible and will occur to those of skill in the art. The epitopic determinant region, roughly including the region from amino acid 5-433 of the VP2 region, thus constitutes a recombinant "cassette" which may be tailored by site-specific mutagenesis to achieve amino acid insertion and/or deletion to provide desired recombinant cDNA clones, polypeptides, virus-like particles and vaccines with improved protection against a wide variety of IBDV.

Lethal IBDV, Monoclonal Antibody and Vaccine Therefore

As noted, typically, IBDV infection creates an immunosuppressive condition, and is reflected in lesions in the bursa of Fabricius. This is typical of IBDV countered in the United States. There exist, however, lethal IBDV, that is, IBDV infections which results in chicken mortality directly as a result of IBDV infection. While vaccines have been developed on the basis of isolation of these IBDV, the resulting vaccines are "hot", that is, they themselves create or induce an immunosuppressive condition, and the inoculated chick must be bolstered with antibodies to other infectious agents. This method of protection is so undesirable as to have been discontinued in most commercial poultry houses in Europe. No adequate safe vaccine against the lethal IBDV is currently available.

The inventors have developed a monoclonal antibody, Mab 21, deposited under Budapest Treaty conditions at the American Type Culture Collection, Deposit Accession No. ATCC HB 11566. This monoclonal antibody is specific and neutralizing for lethal IBDV strains. The specificity is reflected in Table 5, which confirms that unlike other monoclonal antibody, Mab 21 is specific for an epitope exhibited only by IBDV strains having lethal potential.

TABLE 5

| Source | IBDV Strain | Comment | B29 | 8 | 179 | 10 | 63 | 69 | 21 | 67 | 57 | 58 |
|--------|-------------|---------|-----|---|-----|----|----|----|----|----|----|----|
| | Lethal Potential | | | | | | | | | | | |
| | IM+ | | + | + | + | + | + | + | + | − | − | − |
| Sharma | IM | | + | + | + | + | + | + | + | − | − | − |
| USDA | STC | | + | + | + | + | + | + | + | − | − | − |
| Spatas | 2512 (Winterfield) | | + | + | + | + | + | + | + | − | − | − |
| Edgar | Edgar Pathogenic Virus | (vaccine hot) | + | + | + | + | + | + | + | − | − | − |
| Sterwin | Birses Vac Vaccine Vinis | (vaccine hot) | + | + | + | + | + | + | + | − | − | − |
| ASL | Univax-BD | (St 14) | + | + | + | + | + | + | − | − | − | − |
| Select | Bursal Disease Vaccine | (Luk) | + | + | + | + | + | + | − | − | − | − |
| Select | | (STD + VAR) | + | + | + | + | + | + | − | − | − | − |
| | | | + | + | + | + | + | + | − | − | − | − |
| Key Vet | Bio-Burs I | (D78) | + | + | + | + | + | + | − | − | − | − |
| Key Vet | Bio-Burs W | (Luk) | + | + | + | + | + | + | − | − | − | − |
| Key Vet | Key-Burs | (D78) | + | + | + | + | + | + | − | − | − | − |
| MBL | Maryland | (Master seed) | + | + | + | + | + | + | − | − | − | − |

TABLE 5-continued

| Source | IBDV Strain | Comment | B29 | 8 | 179 | 10 | 63 | 69 | 21 | 67 | 57 | 58 |
|---|---|---|---|---|---|---|---|---|---|---|---|---|
| Sterwin | BVM | (Baxendale) | + | + | + | + | + | +/− | − | − | − | − |
| Sterwin | 1048-E | | + | + | + | + | + | +/− | − | − | − | − |
| Lukert | BVM | (Lab Strain) | + | + | + | + | + | +/− | − | − | − | − |
| CEVA | Bursa Blend | (2512) | + | + | + | + | + | + | − | − | − | − |
| InterVet | D78 | | + | + | + | + | + | + | − | − | − | − |
| InterVet | Prime Vac | | + | + | + | + | + | + | − | + | + | − |
| InterVet | 8903 | | + | + | + | − | + | − | − | + | − | − |
| Solvay | Bursine | (Luk) | + | + | + | + | + | + | − | − | − | − |
| Solvay | Bursine II Lab Virus | (Luk+) | + | + | + | + | + | + | − | − | − | − |
| JKR | E/Del | | + | + | + | − | + | − | − | + | − | − |
| JKR | A/Del | | + | + | + | − | + | − | − | + | − | − |
| KKR | D/Del | | + | + | + | − | + | − | − | + | − | − |
| DBS | GLS | | + | + | + | + | − | − | − | − | + | − |
| DBS | DS326 | | + | + | − | + | − | − | − | − | + | + |
| *Skeels | S977 | | + | + | + | + | + | + | − | − | − | − |
| OH | | (Serotype II) | + | + | + | + | + | + | − | − | − | − |

*Field Strains: All classic filed strains tested to date which were isolated in the U.S. have the 21 marker
NOTE:
1 Lukert and STC are Edgar derivatives.
2 Univax is a Bursa Vac derivative.
3. Bursa Blend is a 2512 Winterfield derivative It should be noted that throughout this application, reference is made to a variety of monoclonal antibody which are used to confirm the presence of epitopes of different IBDV in the inventive recombinant chimeric immunogens of the application. These monoclonal antibody have also been deposited under Budapest Treaty conditions and are freely available. They are not, however, necessary for the practice of this invention, and do not constitute an aspect thereof. This should be contrasted with Mab 21.

Like other Mab developed by the inventors herein for IBDV, passive immunization against IBDV lethal strains, particularly designed to achieve immunization in a uniform, standardized level, and to augment any maternally derived levels against lethal IBDV field infection can be obtained by vaccinating one-day old chicks with a vaccine comprising a pharmacologically acceptable carrier such as those described above, in which is present an amount of Mab 21 effective to provide enhanced protection for the inoculated chicks.

The necessary level of protection can be conferred to by a single dose of the vaccine administered in ova or to a day-old chick having a Mab 21 concentration of between 1 microgram and 1 milligram, or repeated vaccinations having a smaller effective dose, but carried out over time. If repeated vaccinations are used, the dosage levels should range between 1 microgram and 1 milligram. The concentration level needed to vaccinate older chickens increases with the weight of the bird and can be determined empirically.

Further investigation of the amino acid sequences of the lethal strains in the epitopic determinant region reflects the highly conserved 279 identity Asn at position 279 of VP2, in non-lethal strains, with a conserved Asp identity at the same position in lethal strains. Accordingly, the lethal strain epitopic determinant recognized by Mab 21, unique to the lethal strains, empirically differs from non-lethal IBDV by the substitution 279 Asp-Asn. According to the methods set forth above, a chimeric, recombinant immunogen conferring effective protection against lethal IBDV, something not possible previously with any type of vaccine without inducing an immunosuppressive condition, may be prepared by inserting the genetic epitopic determinant for 279 Asp in a non-lethal base IBDV, such as GLS. This will confer protection against the base IBDV, the lethal IBDV, as well as all other IBDV whose genetic epitopic determinants are inserted. Vaccines prepared from these immunogens, whether VP2 only, or in the form of virus-like particles of VP2-VP-VP3 segments, are used in the same fashion as discussed above.

What is claimed is:

1. A chimeric polypeptide immunogen comprising the VP2 amino acid sequence of a first infectious bursal disease virus (IBDV) except for at least one amino acid X, wherein X is an epitopic determinant from a second IBDV strain wherein said IBDV strains are selected from the group consisting of GLS, E/Del, D78, DS326, RS593, Cu-1, PBG98, 52/70, STC and 002-73, and wherein said immunogen comprises the amino acid sequence, in order, for IBDV structural proteins VP2-VP4-VP3.

2. The immunogen of claim 1, wherein said VP2 amino acid sequence comprises a plurality of a different epitopic determinant X.

3. The immunogen of claim 2, wherein said plurality of epitopic determinants X are from at least two different IBDV strains.

4. The immunogen of claim 1, wherein said immunogen is in the form mimicking the three-dimensional structure of IBDV.

5. The immunogen of claim 6, wherein said immunogen exhibits at least one IBDV conformational epitope.

6. The immunogen of claim 1, wherein said amino acid sequence includes an epitopic determinant X of a lethal IBDV strain.

7. The immunogen of claim 6, wherein said epitopic determinant of lethal IBDV strains comprises the amino acid Asp at position 279 of the VP2 sequence.

8. A preparation sufficient to provide poultry inoculated therewith resistance to IBDV challenge from at least two different IBDV strains, comprising, as an active agent, an effective amount of the immunogen of claim 1, and a pharmacologically acceptable carrier.

9. The chimeric polypeptide immunogen of claim 1 wherein said immunogen is an avirulent immunogen which confirms on poultry inoculated therewith protection against challenge from IBDV lethal strains, said immunogen comprising the VP2 amino acid sequence of an IBDV, wherein position 279 of said VP2 amino acid is Asp.

10. The immunogen of claim 9, in the form mimicking the three-dimensional structure of IBDV.

\* \* \* \* \*